US009428575B2

(12) United States Patent
Lai et al.

(10) Patent No.: US 9,428,575 B2
(45) Date of Patent: Aug. 30, 2016

(54) ANTI-GRANULYSIN ANTIBODIES AND METHODS OF USE THEREOF

(71) Applicants: Development Center for Biotechnology, New Taipei (TW); DCB-USA LLC, Wilmington, New Castle, DE (US)

(72) Inventors: Jiann-Shiun Lai, New Taipei (TW); Hung-Ling Wang, New Taipei (TW); Chao-Yang Huang, New Taipei (TW); Ying-Yung Lok, New Taipei (TW); Yuan-Tsong Chen, New Taipei (TW); Woan-Eng Chan, New Taipei (TW); Chih-Yung Hu, New Taipei (TW)

(73) Assignees: Development Center for Biotechnology, New Taipei (TW); DCB-USA LLC, Wilmington, DE (US); Academia Sinica, Taipei (TW)

( * ) Notice: Subject to any disclaimer, the term of this patent is extended or adjusted under 35 U.S.C. 154(b) by 0 days.

(21) Appl. No.: 14/145,583

(22) Filed: Dec. 31, 2013

(65) Prior Publication Data

US 2014/0186352 A1    Jul. 3, 2014

Related U.S. Application Data

(60) Provisional application No. 61/747,800, filed on Dec. 31, 2012.

(51) Int. Cl.
*C07K 16/18* (2006.01)

(52) U.S. Cl.
CPC .......... *C07K 16/18* (2013.01); *C07K 2317/55* (2013.01); *C07K 2317/565* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 7,718,378 B2 * | 5/2010 | Chen ................... G01N 33/564 435/7.1 |
| 8,377,436 B2 * | 2/2013 | Chen ................... G01N 33/564 424/130.1 |
| 2005/0239699 A1 * | 10/2005 | Okada et al. .................... 514/12 |
| 2011/0014215 A1 * | 1/2011 | Chen et al. ................. 424/173.1 |

FOREIGN PATENT DOCUMENTS

EP          1484066 A1    12/2004

OTHER PUBLICATIONS

Janeway et al., Immunology, 3rd edition, Garland Publishing Inc., New York, 1997, pp. 3:1-3:11.*
Rudikoff et al., Proc Natl Acad Sci U S A. Mar. 1982;79(6):1979-83.*
Paul W.E., Fundamental Immunology, Raven Press, New York, 1993, p. 242.*
Portolano et al., J Immunol. Feb. 1, 1993;150(3):880-7.*
International Search Report issued in corresponding International Application No. PCT/US2013/078441 mailed Apr. 22, 2014 (6 pages).
Written Opnion issued in corresponding International Application No. PCT/US2013/078441 mailed Apr. 22, 2014 (6 pages).
NCBI, Genbank accesion No. EAW99484.1 mailed Feb. 4, 2010 (2 pages).
NCBI, Genbank accesion No. ADM44545.1 mailed Aug. 31, 2010 (1 page).
Chung, Wen-Hung et al., "Granulysin is a key mediator for disseminated keratinocyte death stevens-johnson syndrome and toxic epidermal necrolysis", Nature Medicine, vol. 14, No. 12, pp. 1343-1350, mailed Nov. 23, 2008 (8 pages).
Fujita, Yasuyuki et al., "Rapid immunochromoatographic test for serum granulysis is useful for the prediction of stevens-johnson syndrome and toxic epidermal necrolysis", Journal of American Academy of Dermatology, vol. 65, No. 1, pp. 65-68, mailed Jul. 2011 (4 pages).
Chung, Wen-Huang et al., "Genetic markers and danger signals in stevens-johnson syndrome and toxic epidermal necrolysis", Allergology International, vol. 59, No. 4, pp. 325-332, 2010 (8 pages).
PCT Notification Concerning Transmittal of International Preliminary Report on Patentability dated Jul. 9, 2015, with the International Preliminary Report on Patentability and Written Opinion issued Jun. 30, 2015, by the International Bureau in related International Application No. PCT/US2013/078441 (8 pages).
Patent Examination Report No. 1, issued Dec. 17, 2015, by the Australian Patent Office in related Australian Patent Application No. AU-2013370009 (5 pages).
Patent Examination Report No. 2 dated Jun. 10, 2016, issued by the Australian Patent Office in related Australian Patent Application No. 2013370009 (2 pages).

(Continued)

*Primary Examiner* — Michael Szperka
(74) *Attorney, Agent, or Firm* — Osha Liang LLP

(57) ABSTRACT

An anti-granulysin antibody, or an scFv or Fab fragment thereof, capable of binding to an epitope region from R64 to R113 of granulysin and capable of neutralizing an activity of granulysin. The antibody may contain a sequence selected from the sequences of SEQ ID NO:82 to SEQ ID NO:195, or the antibody may contain a sequence selected from the sequences of SEQ ID NO:39 to SEQ ID NO:76. The antibody may be a monoclonal antibody. A method for treating or preventing an unwanted immune response disorder includes administering to a subject in need thereof an effective amount of an anti-granulysin antibody capable of neutralizing the activity of granulysin. The unwanted immune response disorder may be SJS, TEN, or GVHD.

13 Claims, 22 Drawing Sheets

(56) References Cited

OTHER PUBLICATIONS

EPO Communication pursuant to Rule 164(1) EPC dated Jul. 12, 2016 (2 pages), and partial Supplementary European Search Report dated Jun. 29, 2016, issued in related European Patent Application No. EP-13 86 8770 (8 pages).
Farouk, Salah E., et al., "gd T cells inhibit in vitro growth of the asexual blood stages of Plasmodium falciparum by a granule exocytosis-dependent cytotoxic pathway that requires granulysin"; European Journal of Immunology, vol. 34, No. 8, Aug. 2004; XP009190723, ISSN: 0014-2980; pp. 2248-2256.
Peña, Susan V., et al., "Processing, Subcellular Localization, and Function of 519 (Granulysin), a Human Late T Cell 4ctivation Molecule with Homology to Small, Lytic, Granule Proterns1"; The Journal of Immunology, The American 4ssociation of Immunologists, U.S., vol. 158, No. 6, Mar. 15, 1997; XP002920631, ISSN: 0022-1767; pp. 2680-2688.
Jun, Ju, et al., "The purification of recombinated granulysin and the preparation of its monoclonal antibody"; Chinese Journal of Cellular and Molecular Immunology, vol. 26, No. 6, Jun. 2010; XP009190727, ISSN: 1007-8738; pp. 563-565.
Chung, Wen-Hung, et al., "Recent advances in the genetics and immunology of Stevens-Johnson syndrome and toxic epidermal necrosis"; Journal of Dermatological Science, Elsevier Science Publishers, vol. 66, No. 3, Apr. 9, 2012; XP028507063, ISSN: 0923-1811, DOI: 10.1016/J.JDERMSC12012.04.002 [retrieved on Apr. 11, 2012]; pp. 190-196.
Pichler, Werner J., MD, et al., "Immune pathomechanism of drug hypersensitivity reactions"; Journal of Allergy and clinical Immunology, Elsevier, Amsterdam, NL, vol. 127, No. 3, Nov. 12, 2010; XP028182678, ISSN: 0091-6749, DOI: 10.1016/J.JACI.2010.11.048 [retrieved on Dec. 20, 2010]; pp. S74-S81.

\* cited by examiner

| Clone name | Type | Select method | CDRH1 (SEQ ID NO) | CDRH2 (SEQ ID NO) | CDRH3 (SEQ ID NO) | CDRL1 (SEQ ID NO) | CDRL2 (SEQ NO) | CDRL3 (SEQ ID NO) |
|---|---|---|---|---|---|---|---|---|
| GP42-15 (BGF42-15) | scFv | Plate | GYTFSNYDIN (82) | WIDPGNGRTKYNEKFEG (83) | -VGDDYD-GGFDY (84) | KASQS-VDYDGDSYMN (85) | RASNLES (86) | QQSNEYPYT (87) |
| GP42-56 | scFv | Plate | GYTFSNYDIN (88) | WIDPGNGRTKYNEKFEG (89) | -VGDDYD-GGFDY (90) | RASES-VDSYGNSFMH (91) | RTSNLES (92) | QQSYEEPYT (93) |
| GP42-10 | scFv | Plate | GYTFSNYDIN (94) | WIDPGNGRTKYNEKFED (95) | -VGDDYD-GDFDY (96) | RASES-VDSYGNSFMH (97) | RASNLES (98) | QQSNEYPYT (99) |
| GP31-52 | scFv | Plate | GYSFTNYDIN (100) | WIDPGNGRTKYNEKFTG (101) | -VGDDYD-GGFDY (102) | SASSS-VSSSYLH-- (103) | RTSNLAS (104) | FQGSGYPYT (105) |
| GP42-58 | scFv | Plate | GYTFTSYDIN (106) | WIDPGDGRTKYNEKFEG (107) | -VGDDYD-GGFDY (108) | SASES-VDSYGNSFMN (109) | RASNLES (110) | QQSNEYPYT (111) |
| BGF32-42 | Fab | Bead | GYTFTSFDIN (112) | WIDPGNGRTKYNEKFEG (113) | -VGDDYD-GGFDY (114) | KASQS-VDYDGDSYMN (115) | LASNLES (116) | QQSYEEPYT (117) |
| BGF32-48 | Fab | Bead | GYPFASYDLN (118) | WIDPGNGRTKYNEKFEG (119) | -VGDDYD-GGFDY (120) | RASES-VDSYGDRFMN (121) | RVSNRFS (122) | QQDYEEPYT (123) |
| GP42-27 | scFv | Plate | GYTFTNYDIN (124) | WIDPGDGRTKYNENFKD (125) | -VGDDYD-GGFDY (126) | RASES-VDSYGNSFMH (127) | AASNQES (128) | QQSYEDPYT (129) |
| GP42-42 | scFv | Plate | GYTFTNYDIN (130) | WIDPGDGSTKYNEKFKG (131) | -VGNDYD-GGFDF (132) | RASES-VDSYGDSFMY (133) | RTSNLES (134) | QQSNEYPYT (135) |
| BGF33-19 | Fab | Bead | GYAFTNYLIE (136) | VINPGSSGGTNVNEKFKG (137) | EGEKHSYY-FDY (138) | RASES-VDSYGDSFMH (139) | LASNLES (140) | QQNNEDPPT (141) |
| BGF31-71 | Fab | Bead | GYTFTDHAIH (142) | YISPGNGDVWYNEKFKG (143) | -WNY-GYFDV (144) | RSSQSLVHSNGNTYLH (145) | KVSNRFS (146) | SQSTHVPWT (147) |
| GP42-79 | scFv | Plate | GFNIKDYYMH (148) | WIDPENGDTEYAPKFQG (149) | -SDY-AMDY (150) | SASSS-VS---YMY (151) | DTSNLAS (152) | QQWSSYPLT (153) |
| GP42-09 | scFv | Plate | GFNIKDYYMH (154) | WIDPENKGNTIYDPKFQG (155) | -VGDDYD-GDFDY (156) | RASES-VDSYGDSFMH (157) | RASNLES (158) | QQSYEEPYT (159) |
| GP31-31 (BGF32-11) | scFv | Plate | GYTFTKYTMH (160) | FINPNSGYTDYNQKFKA (161) | YPIYSDYGPYAMDY (162) | RASES-VDSYGDSFMH (163) | RASNLES (164) | QQSHGDPYT (165) |
| BGF31-41 | Fab | Bead | GYTFSRYTMH (166) | FENPNSGYTDYNQKFKD (167) | HPWSDYGPYAMDY (168) | RASES-VDSYGNSFMH (169) | LASNLES (170) | QQNNEDPWT (171) |
| BGF2A-92 | Fab | Bead | GFTFSDYYMAV (172) | TISDGGSYTYYPDSVKG (173) | -EGDYY-GPFAY (174) | KASQN-VGTAVA-- (175) | SASYRYS (176) | QQYNSYPT (177) |
| M34-22 | Hybr | Hybr | SGYIFTDYSIH (178) | WIGVISSYYGDARHNQKFKG (179) | DGYYGYAMDY (180) | RSTQSLVHSNGNTYLH (181) | KVSYRFSGVPDRFS (182) | SQSTHVPFTF (183) |
| M16.7 | Hybr | Hybr | SGYIFTDYNM (184) | WIGDINPNVGDTYNQKFKG (185) | SDDNYSWFIY (186) | KASQSVSNDVA (187) | YASNHYT (188) | QQDSSSPLIF (189) |
| M105.17 | Hybr | Hybr | SGYIFTDYNM (190) | WIGDINPNNVGDTYNQNFKD (191) | SDDDYSWFAH (192) | KASQSVSNDVA (193) | YASNRYT (194) | QQDSSSPLIF (195) |

FIG. 7

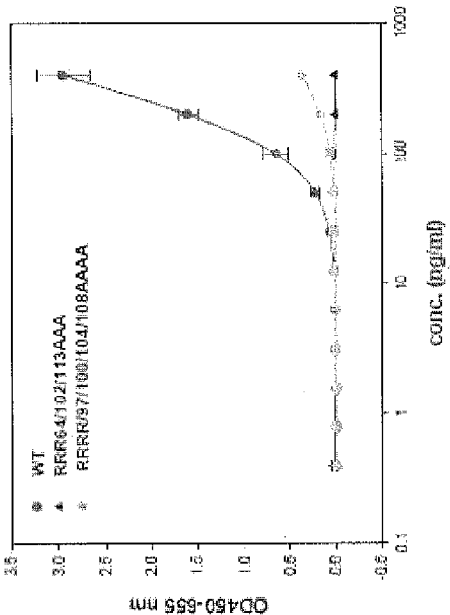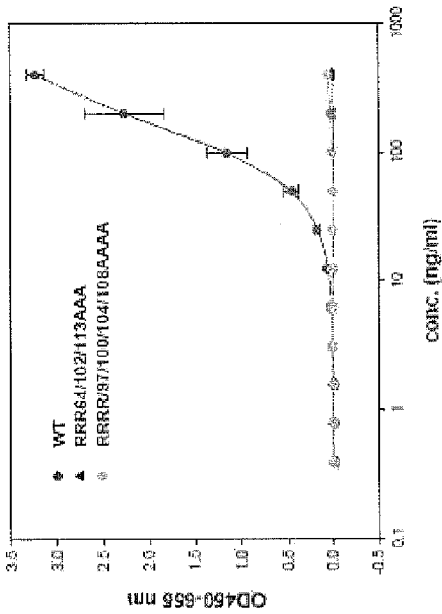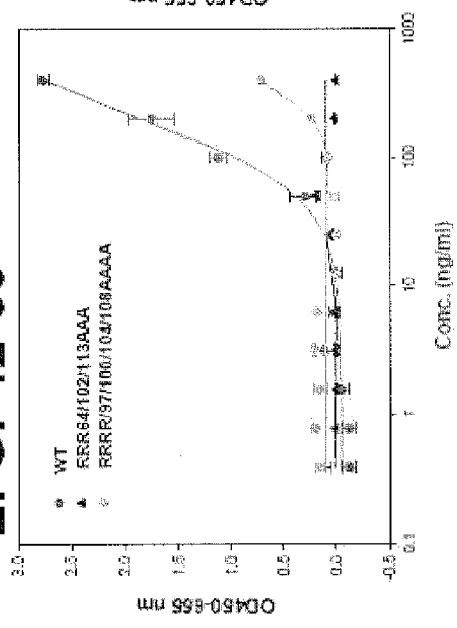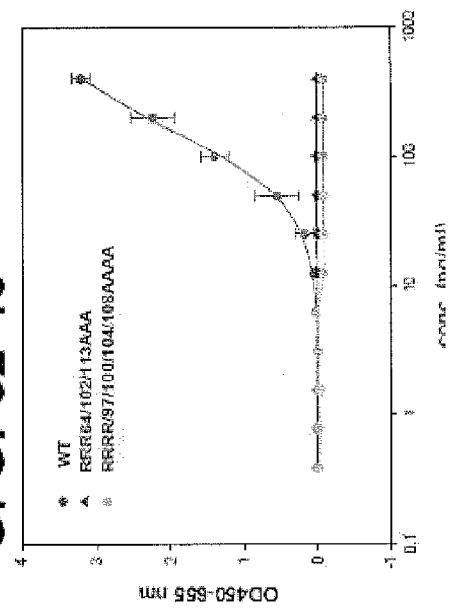
FIG. 13 (Continued)

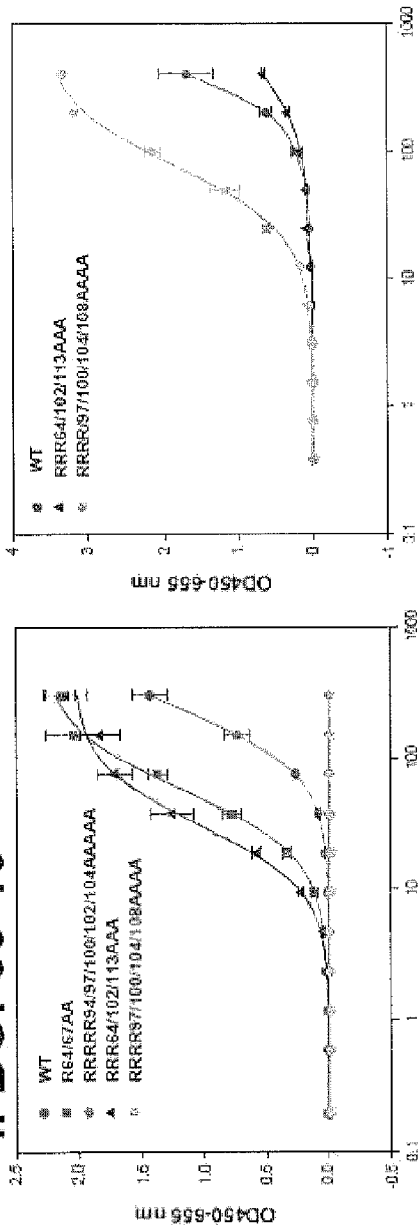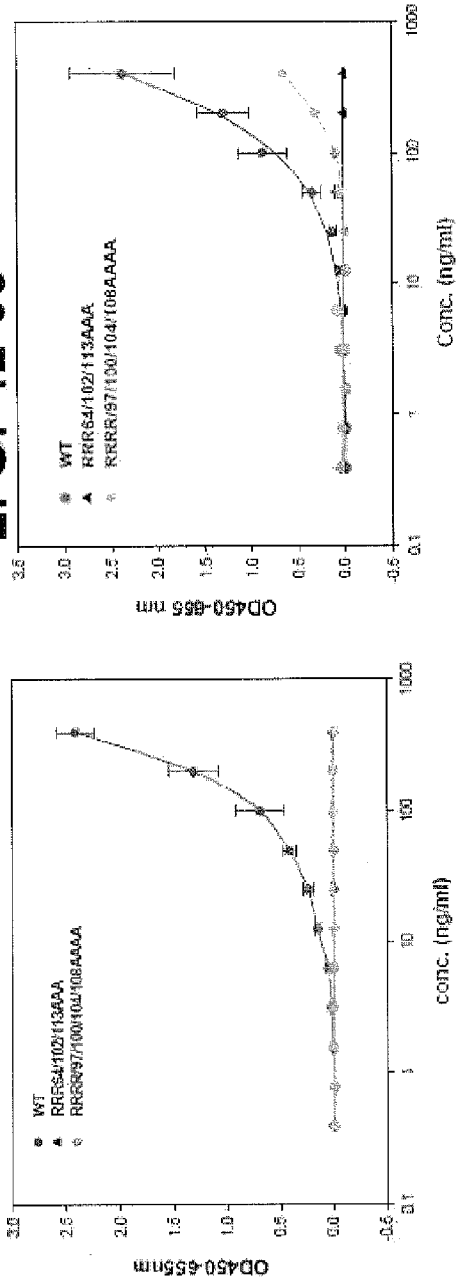
FIG. 13
(Continued)

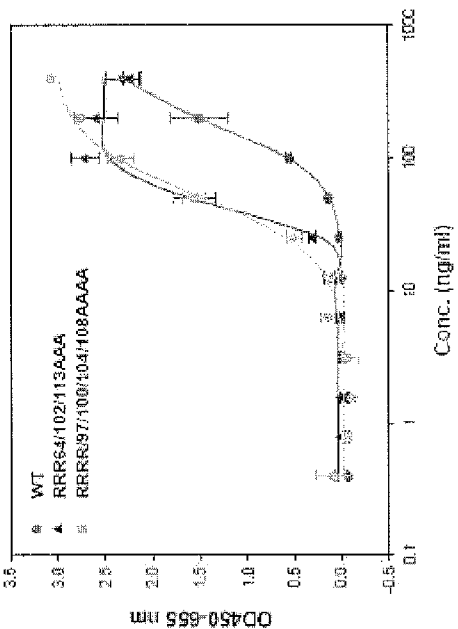
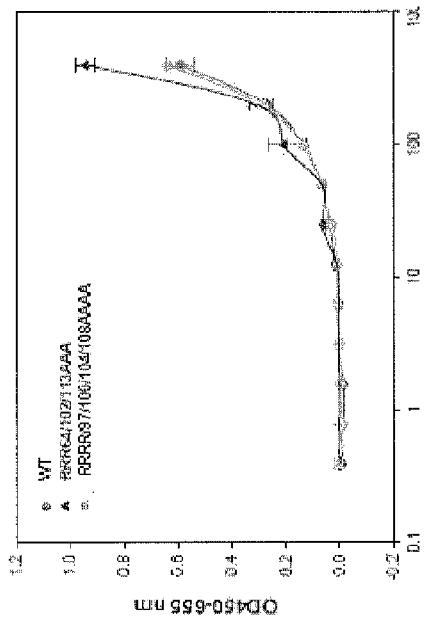
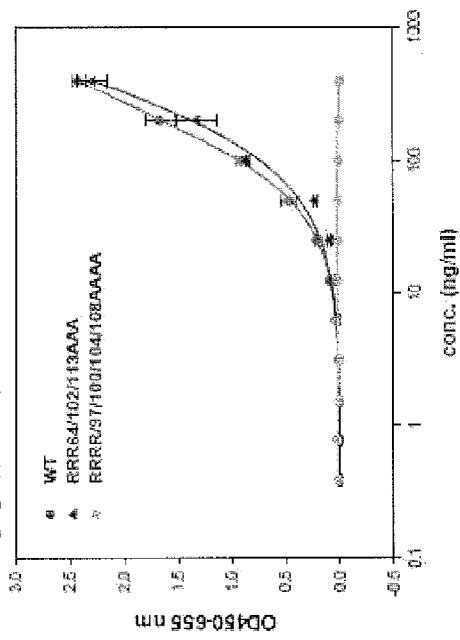
FIG. 13 (Continued)

FIG. 15
Schematic diagrams of granulysin action.
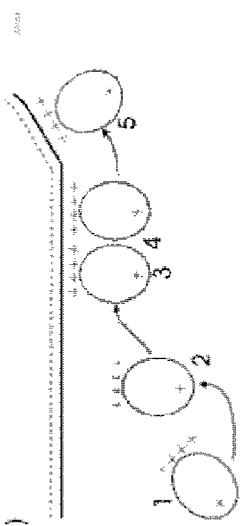
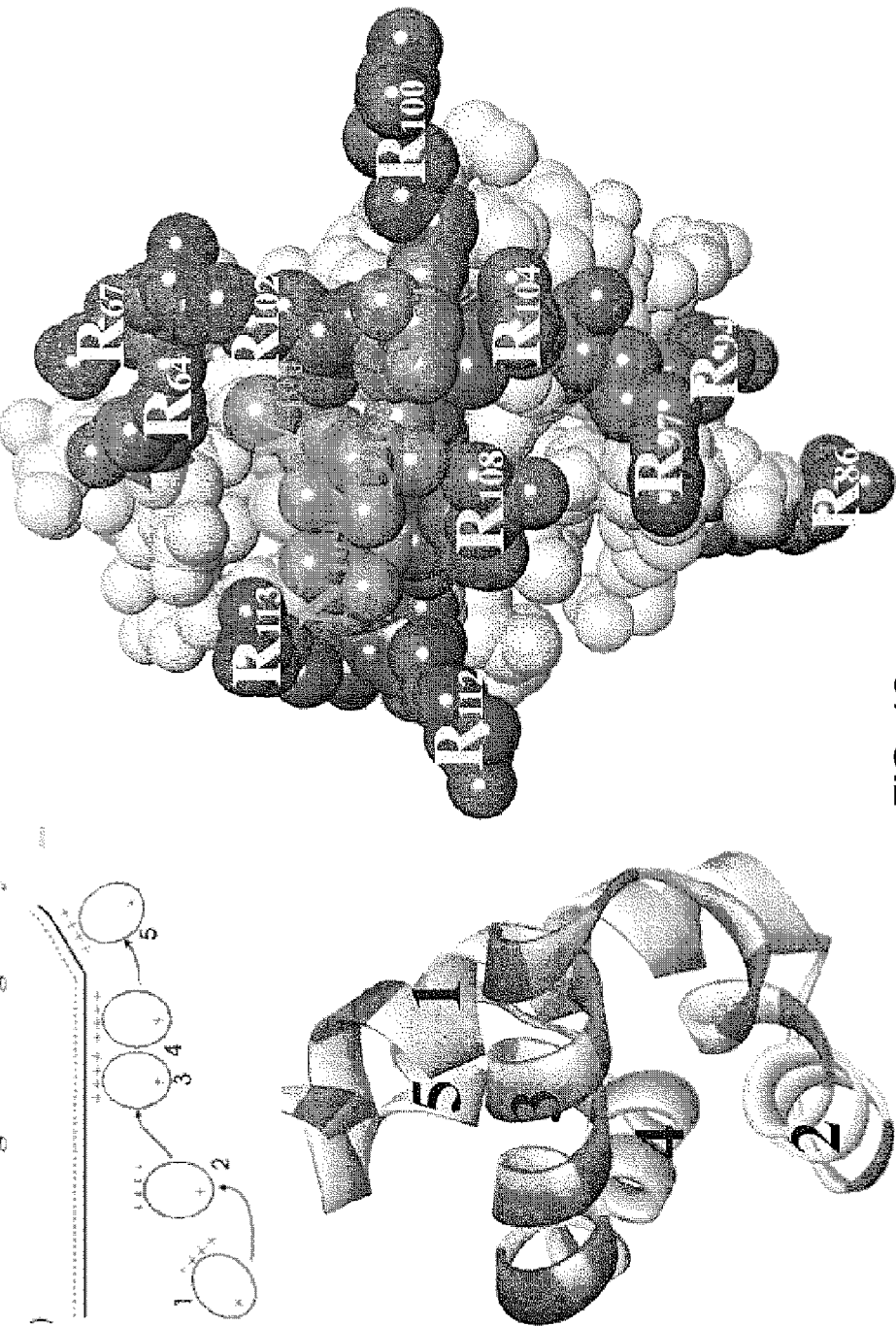
FIG. 16

Summary of the granulysin-neutralizing antibodies

| Analyte | GNLY (Batch) 15K | | GNLY (Batch) 19K | | | Epitope | | |
|---|---|---|---|---|---|---|---|---|
| Antibodies | KD | Reverse antimicrobial activity | KD | Reverse antimicrobial activity | Binding to denatured rhGNLY | N6 | 1st (a.a. 1-8) | R2 (a.a.100, 104, 108) |
| GP42-15 | 2.45E-11 | +++ | 3.31E-10 | +++ | + | +++ | -

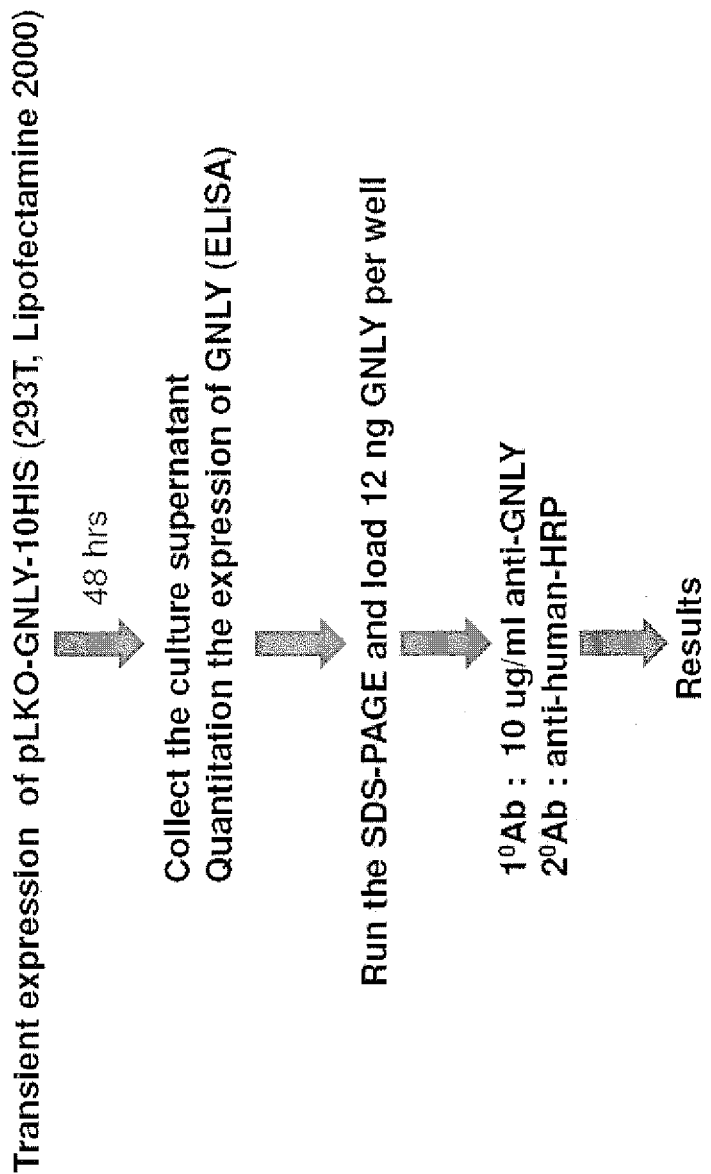

SEQUENCE LISTING

```
<160> NUMBER OF SEQ ID NOS: 195

<210> SEQ ID NO 1
<211> LENGTH: 314
<212> TYPE: DNA
<213> ORGANISM: Mus musculus

<400> SEQUENCE: 1
gtctttagtg aagatatcct gcaaggcttc tggttatacc ttcagtaatt acgatataaa        60
ctgggtgaga cagaggcctg gacgggactt gagtggattg gatggattga tcctggaaat       120
ggtcgtacta agtacaatga gaaattcgag ggcaaggcct cactgactgc agacaaatcc       180
tccagcacag ccttcatgct gctcagcagc tgacttctga caattctgca gtctatttct       240
gtgcaagagt gggggatgat tacgacgggg gttttgacta ctggggccaa gggaccacgg       300
tcaccgtctc ctca                                                          314
```

<210> SEQ ID NO 2
<211> LENGTH: 288
<212> TYPE: DNA
<213> ORGANISM: Mus musculus

<400> SEQUENCE: 2

```
ggcagagggc caccatctcc tgcaaggcca gccaaagtgt tgattatgat ggtgatagtt      60
atatgaactg gtaccaacag aaccaggaca gccacccaaa ctcctcatct atcgtgcatc     120
caacctcgaa tctgggatcc ctgtcaggtt cagtggcagt gggtctcgga cagacttcac     180
cctcaccatt aatcctgtgg aggctgatat gttgcaacct attactgtca gcaaagtaat     240
gaatatccgt atacgttcgg agggggggacc aagctggagc tgaaacgg                  288
```

<210> SEQ ID NO 3
<211> LENGTH: 358
<212> TYPE: DNA
<213> ORGANISM: Mus musculus

<400> SEQUENCE: 3

```
caggtgaagc tgcagcagtc gggacctgac ctggtgaagc ctgggtcttt agtgaagata      60
tcctgcaagg cttctggtta taccttcagt aattacgaca taaactgggt gaaacagagg     120
cctggacggg acttgagtgg attggatgga ttgatcctgg aaatggtcgt actaagtaca     180
atgagaaatt cgagggcaag gcctcactga ctgcagacaa atcctccagc acagccttca     240
tgctgctcag cagctgactt ctgacgactc tgcagtctat ttctgtgcaa gagtggggga     300
tgattacgac gggggttttg actactgggg ccaagggacc acggtcaccg tctcctca      358
```

<210> SEQ ID NO 4
<211> LENGTH: 288
<212> TYPE: DNA
<213> ORGANISM: Mus musculus

<400> SEQUENCE: 4

```
ggcagagggc caccatatcc tgcagagcca gtgaaagtgt tgatagttat ggcaatagtt      60
ttatgcactg gtaccagcag aaccaggaca gtcacccaaa ctcctcatct atcgtacatc     120
caacctagaa tctgggatcc ctgccaggtt cagtggcagt gggtctagga cagacttcac     180
cctcaccatt aatcctgtgg aggctgatat gttgcgacct attactgtca gcaaagttat     240
gaggaaccgt acacgttcgg agggggggacc aagctggagc tgaaacgg                  288
```

<210> SEQ ID NO 5
<211> LENGTH: 269
<212> TYPE: DNA
<213> ORGANISM: Mus musculus

<400> SEQUENCE: 5

```
gtctttagtg aagatatcct gcaaggcttc tggttatacc ttcagtaatt acgatataaa      60
ctgggtgaaa cagaggcctg acgggacttg agtggattg gatggattga tcctggaaat     120
ggtcgtacta agtacaatga gaaattcgag gacaaggcca cactgactgc agacaaatcc     180
tccagcacag cctacatgca gctcagcagc tgacttctga ggactctgca gtctatttct     240
gtgcaagagt gggggatgat tacgacggg                                        269
```

<210> SEQ ID NO 6
<211> LENGTH: 291
<212> TYPE: DNA
<213> ORGANISM: Mus musculus

<400> SEQUENCE: 6

| gggagaaggt caccatgacc tgcagagcca gtgaaagtgt tgatagttat ggcaatagtt | 60 |
| ttatgcactg gtaccagcag aaccaggact gccacccaaa ctcctcatct atcgtgcatc | 120 |
| caacctagaa tctgggatcc ctgccaggtt cagtggtagt gggtctagga cagacttcac | 180 |
| cctcaccatt aatcctgtgg aggctgatat gttgcaacct attactgtca gcaaagtaat | 240 |
| gaatatccgt acacgttcgg agggggggacc aagctggaaa taaaacgggc g | 291 |

<210> SEQ ID NO 7
<211> LENGTH: 358
<212> TYPE: DNA
<213> ORGANISM: Mus musculus

<400> SEQUENCE: 7

| caggtgcagc tgcagcagtc aggacctgac ctggtgaagc ctggggcttt agtgaagata | 60 |
| tcctgcaagg cttctggtta tagcttcaca aactacgata ttaactgggt gaaacagagg | 120 |
| cctggacggg acttgagtgg attggatgga ttgatcctgg aaatggtcgt actaagtaca | 180 |
| atgagaaatt cacgggcaag gcctctctga ctgcagacaa atcctccagc acagcctaca | 240 |
| tggtgctcag cagctgactt ctgaaaactc tgcagtctat ttctgtgcaa gagtggggga | 300 |
| tgattacgac gggggttttg actactgggg ccaagggacc acggtcaccg tctcctca | 358 |

<210> SEQ ID NO 8
<211> LENGTH: 279
<212> TYPE: DNA
<213> ORGANISM: Mus musculus

<400> SEQUENCE: 8

| ggcagaaggt caccatgacc tgcagtgcca gctcaagtgt aagttccagt tacttgcact | 60 |
| ggtaccagca gaagtcaggc gttccccccaa acccttgatt cataggacat ccaatctggc | 120 |
| ttctggagtc cctgctcgct tcagtggcag tgggtctgga aactcttact ctctcacgat | 180 |
| cagcagcatg gaggctgaag atgttgccct tattactgtt ttcaggggag tgggtacccg | 240 |
| tacacgttcg gaggggcac caagctggaa atcaaacgg | 279 |

<210> SEQ ID NO 9
<211> LENGTH: 314
<212> TYPE: DNA
<213> ORGANISM: Mus musculus

<400> SEQUENCE: 9

| ggctttagtg aagatatcct gcaaggcttc tggttatacc ttcacaagtt acgatataaa | 60 |
| ctgggtgaaa cagaggcctg acgggacttg agtggattg gatggattga tcctggagat | 120 |
| ggtcgtacta agtacaatga gaaattcgag gcaaggcct cactgactgc agacaaatcc | 180 |
| tccagcacag cctacatgct actcagcagc tgacttctga caactctgca gtctatttct | 240 |
| gtgcaagagt gggggatgat tacgacgggg gttttgacta ctggggccaa gggaccacgg | 300 |
| tcaccgtctc ctca | 314 |

<210> SEQ ID NO 10
<211> LENGTH: 288
<212> TYPE: DNA
<213> ORGANISM: Mus musculus

<400> SEQUENCE: 10

```
gggagaaggt caccatatcc tgcagtgcca gtgaaagtgt tgatagttat ggcaatagtt      60
ttatgaactg gtaccagcag aaccaggaca gccacccaaa ctcctcatct atcgtgcatc     120
caacctagaa tctgggatcc ctgtcaggtt cagtggcggt gggtctcgga cagacttcac     180
cctcaccatt aatcctgtgg aggctgatat gttgcaacct attactgtca gcaaagtaat     240
gaatatccgt atacgttcgg aggggcacc aagctggaaa tcaaacgg                   288
```

<210> SEQ ID NO 11
<211> LENGTH: 360
<212> TYPE: DNA
<213> ORGANISM: Mus musculus

<400> SEQUENCE: 11

```
vhcaggtcca gctgcagcag tctggagctg aactggtaaa gcctggggct tcagtgaagt      60
tgtcctgcaa ggcttctggc tacaccttca caagctttga tataaactgg gtgaaacaga    120
ggcctggacg ggacttgagt ggattggatg gattgatcct ggaaatggtc gtactaagta    180
caatgagaaa ttcgagggca aggtctcact gactgcagac aaatcctcca gcacagcctt    240
catgctgctc agcagctgac ttctgacaac tctgcagtct atttctgtgc aagagtgggg    300
gatgattacg acggggtttt tgactactgg ggccaaggca ccactctcac agtctcctca    360
```

<210> SEQ ID NO 12
<211> LENGTH: 288
<212> TYPE: DNA
<213> ORGANISM: Mus musculus

<400> SEQUENCE: 12

```
ggcagagggc caccatctcc tgcaaggcca gccaaagtgt tgattatgat ggtgatagtt      60
atatgaactg gtaccaacag aaccaggaca gccacccaaa ctcttcatct ttcttgcatc    120
caacctagaa tctggggtcc ctgccaggtt cagtggcagt gggtctagga cagacttcac    180
cctcaccatt gatcctgtgg aggctgatat gttgcgacct attactgtca gcaaagttat    240
gaggaaccgt acacgttcgg agggggacc aagctggaaa ttaaacgg                  288
```

<210> SEQ ID NO 13
<211> LENGTH: 313
<212> TYPE: DNA
<213> ORGANISM: Mus musculus

<400> SEQUENCE: 13

```
gcttcagtga agatttcctg caaggcttct ggttatccct cgcaagtta cgatttaaat      60 tgggtgaaac agaggcctgg acgggacttg agtggattgg gtggattgat cctggagatg    120
gtcggactaa gtacaatgag aaattcgagg gcaaggcctc actgactgca gacaaatcct    180
ccagcacagc ctacatgctg ctcagcagct gacttctgac agctctgcag tctatttctg    240
tacaagagtg ggggatgatt acgacggggg ttttgactac tggggccaag gcaccactct    300
cacagtctcc tca                                                       313
```

<210> SEQ ID NO 14
<211> LENGTH: 287
<212> TYPE: DNA
<213> ORGANISM: Mus musculus

<400> SEQUENCE: 14

```
gcagagggcc accatatcct gcagagccag tgaaagtgtt gatagttatg gcgatcgttt      60
tatgaactgg taccagcaga accaggacag ccacccaaac tcctcatcca gcgtgtatcc    120
```

```
aacctaagat ctgggatccc tgccaggttc agtggcagtg ggtcaaggac agacttcacc      180
ctcaccatta atcctgtgga ggctgatatg ttgcaaccta ttactgtcag caagattatg      240
aggagccgta cacgttcgga gggggaccaa gctggaaat aatacgg                     287

<210> SEQ ID NO 15
<211> LENGTH: 313
<212> TYPE: DNA
<213> ORGANISM: Mus musculus

<400> SEQUENCE: 15
acttcagtga agatatcctg caaggcttct ggttacacct tcacaaacta cgatataaac       60
tgggtgaaac agaggcctgg acgggacttg agtggattgg atggattgat cctggagatg      120
gtcgtactaa atacaatgag aacttcaagg acaaggcctc actgactgca gacaaatcct      180
ccagcacagc ctacatgcaa ctgagcagct gacatctgag gactctgcag tctattactg      240
tgcaagagtg ggggatgatt acgacggggg ttttgactac tggggccaag gaccacggt       300 caccgtctcc tca                                                         313

<210> SEQ ID NO 16
<211> LENGTH: 334
<212> TYPE: DNA
<213> ORGANISM: Mus musculus

<400> SEQUENCE: 16
gacattgagc tcacccagtc tccagcttct ttggctgtgt ctctaggaca gagggccacc       60
atatcctgca gagccagtga agtgttgat agttatggca atagttttat gcactggtac       120
cagcagaacc agggcagcca cccagactcc tcatctatgc tgcatccaac caagaatctg      180
ggatccctgc caggttcagt ggcagtgggt ctaggacaga cttcaccctc accattaatc      240
ctgtggaggc tgatatgttg cgacctatta ctgtcagcaa agttatgagg atccgtacac      300
gttcggaggg gggaccaagc tggagctgaa acgg                                  334

<210> SEQ ID NO 17
<211> LENGTH: 358
<212> TYPE: DNA
<213> ORGANISM: Mus musculus

<400> SEQUENCE: 17
caggtcaaac tgcaggagtc aggacctgac ctggtgaagc ctggggcttc agtgaagata       60
tcctgcaagg cttctggtta caccttcaca aactacgata aaactgggt gaagcagagg       120 cctggacggg acttgaatgg attggatgga ttgatcctgg agatggtagt actaagtaca      180
atgagaaatt caaggcaag gcctcactga ctgcagacaa atcctccagc acagcctaca      240
tgctgctcaa cagctgactt ctgaggactc tgcagtctat ttctgtgcaa gagtggggaa      300
tgattacgac gggggttttg acttctgggg ccaagggacc acggtcaccg tctcctca       358

<210> SEQ ID NO 18
<211> LENGTH: 334
<212> TYPE: DNA
<213> ORGANISM: Mus musculus

<400> SEQUENCE: 18
gacattgagc tcacccagtc tccaacttct ttggctgtgt ctctagggca gagggccacc       60
atatcctgca gagccagtga agtgttgat agttatggcg atagttttat gtactggtac       120
```

```
caacagaacc aggacaggca cccaaactcc tcatctatcg tacatccaac ctagaatctg    180
ggatccctgc caggttcagt ggcagtgggt ctaggacaga cttcaccctc accataaatc    240
ctgtggaggc tgatatgttg caacctatta ctgtcagcaa agtaatgaat atccgtatac    300
gttcggaggg gggacaaagt tggaaataaa acgg                                334
```

<210> SEQ ID NO 19
<211> LENGTH: 358
<212> TYPE: DNA
<213> ORGANISM: Mus musculus

<400> SEQUENCE: 19

```
caggtccaac tgcagcagtc tggagctgag ctggtaaggc ctgggacttc agtgaaggtg     60
tcctgcaagg cttctggata cgccttcact aattacttga tagagtgggt aaagcagagg    120
cctggacggg ccttgagtgg attggagtga ttaatcctgg aagtggtggt actaactaca    180
atgagaagtt caagggcaag gcaacattga ctgcagacaa atcctccagc actgcctaca    240
tgcagctcag cagctgacat ctgatgactc tgcggtctat ttctgtgcaa gagaggggga    300
aaaacactct tactactttg actactgggg ccaaggcacc actctcacag tctcctca     358
```

<210> SEQ ID NO 20
<211> LENGTH: 334
<212> TYPE: DNA
<213> ORGANISM: Mus musculus

<400> SEQUENCE: 20

```
gacattgtgc tgacccaatc tccagcttct ttggctgtgt ctctagggca gagggccacc     60
atatcctgca gagccagtga agtgttgat agttatggcg atagttttat gcactggtac    120
cagcagaacc aggacagcca cccaaactcc tcatctatct tgcatccaac ctagaatctg    180
gggtccctgc caggttcagt ggcagtgggt ctaggacaga cttcaccctc accattgatc    240
ctgtggaggc tgatatgctg caacctatta ctgtcagcaa aataatgagg atcctccgac    300
gttcggtgga ggcaccaagc tggaaatcaa acgg                                334
```

<210> SEQ ID NO 21
<211> LENGTH: 349
<212> TYPE: DNA
<213> ORGANISM: Mus musculus

<400> SEQUENCE: 21

```
caggttcaac tgcagcagtc tgacgctgag ttggtgaaac ctggggcttc agtgaagata     60
tcctgcaagg cttctggcta caccttcact gaccatgcta ttcactgggt gaagcagaag    120
cctgaacggg cctggaatgg attggatata tttctcccgg aaatggtgat gtttggtaca    180
atgagaagtt caagggcaag gccacactga ctgcagacaa atcctccagc actgcctaca    240
tgcagctcaa cagctgacat ctgaggattc tgcagtgtat ttctgtaaaa gatggaatta    300
tgggtacttc gatgtctggg gcgcagggac cacggtcacc gtctcctca               349
```

<210> SEQ ID NO 22
<211> LENGTH: 337
<212> TYPE: DNA
<213> ORGANISM: Mus musculus

<400> SEQUENCE: 22

```
gacattgtga tgacccaaac tccactctcc ctgcctgtca gtcttggaga tcaagcctcc     60
atctcttgca gatctagtca gagccttgta cacagtaatg gaaacaccta tttacattgg    120
```

```
tacctgcgaa gccaggccag tctccaaagc tcctgatcta caaagtttcc aaccgatttt    180
ctggggtccc agacaggttc agtggcagtg gatcagggac agatttcaca ctcaagatca    240
gcagagtgga ggctaggatc tgggagttta tttctgctct caaagtacac atgttccgtg    300
gacgttcggt ggaggcacca agctggaaat caaacgg                             337
```

<210> SEQ ID NO 23
<211> LENGTH: 346
<212> TYPE: DNA
<213> ORGANISM: Mus musculus

<400> SEQUENCE: 23

```
caggtcaagc tgcaggagtc tggggcagag cttgtgaggt caggggcctc agtcaagttg     60
tcctgcacag cttctggctt caacattaaa gactactata tgcactgggt gaagcagagg    120
cctgaacggg cctggagtgg attggatgga ttgatcctga aatggtgat actgaatatg    180 ccccgaagtt ccagggcaag gccactatga ctgcagacac atcctccaac acagcctacc    240
tgcagctcag cagctgacat ctgaggactc tgcggtctat tactgtacta gctcggacta    300
tgctatggac tactggggcc aagggaccac ggtcaccgtc tcctca                   346
```

<210> SEQ ID NO 24
<211> LENGTH: 319
<212> TYPE: DNA
<213> ORGANISM: Mus musculus

<400> SEQUENCE: 24

```
gacattgagc tcacccagtc tccagcaatc atgtctgcat ctccagggga aaggtcacc     60 atgacctgca gtgccagctc aagtgtaagt tacatgtact ggtaccagca gaagccagga    120
tcctccccag actcctgatt tatgacacat ccaacctggc ttctggagtc cctgttcgct    180
tcagtggcag tgggtctggg acctcttact ctctcacaat cagccgaatg gaggctgaag    240
atgctgccac ttatactgtc aacagtggag tagttaccca ctcacgttcg gctcggggac    300
aaagttggaa ataaaacgg                                                 319
```

<210> SEQ ID NO 25
<211> LENGTH: 358
<212> TYPE: DNA
<213> ORGANISM: Mus musculus

<400> SEQUENCE: 25

```
caggtgaagc tgcagcagtc aggggctgag cttgtgaggc caggggcctt agtcaagttg     60
tcctgcaaag cttctggctt caacattaaa gactactata tgcactgggt gaagcagagg    120
cctgaacggg cctggagtgg attggatgga ttgatcctga aatggtaat actatatatg    180 acccgaagtt ccagggcaag gccagtataa cagcagacac atcctccaac acagcctacc    240
tgcagctcag cagctgacat ctgaggactc tgcagtctat ttctgtgcaa gagtggggga    300
tgattacgac ggggattttg actactgggg ccaagggacc acggtcaccg tctcctca     358
```

<210> SEQ ID NO 26
<211> LENGTH: 334
<212> TYPE: DNA
<213> ORGANISM: Mus musculus

<400> SEQUENCE: 26

```
gacattgagc tcacccagtc tccagcttct ttggctgtgt ctctagggca gagggccacc     60
```

```
atatcctgca gagccagtga aagtgttgat agttatggcg atagttttat gcactggtac    120
cagcagaacc aggacagcca cccaaactcc tcatctatcg tgcatccaac ctagaatctg    180
ggatccctgc caggttcagt ggcagtgggt ctaggacaga cttcacccte accattaatc    240 ctgtggaggc tgatatgttg caacctatta ctgtcagcaa agttatgagg atccgtacac    300
gttcggaggg gggacaaagt tggaaataaa acgg                                334
```

<210> SEQ ID NO 27
<211> LENGTH: 367
<212> TYPE: DNA
<213> ORGANISM: Mus musculus

<400> SEQUENCE: 27

```
caggtgaagc tgcagcagtc aggggctgaa caggcaagac ctggggcctc agtgaagatg    60
tcctgcaagg cttctggcta cacctttact aaatacacga tgcactgggt aaaacagagg    120
cctggacggg tctggaatgg attggattca ttaatcctaa cagtggatat actgactaca    180
atcagaaatt caaggccagg accacattga ctgcagacaa atcctccacc acagcctaca    240
ttcaactgag cagctgacat ctgaggactc tgcggtctat tactgtgcaa gatacccat     300 ctactctgat tacggcccct atgctatgga ctactgggc caagggacca cggtcaccgt     360
ctcctca                                                              367
```

<210> SEQ ID NO 28
<211> LENGTH: 334
<212> TYPE: DNA
<213> ORGANISM: Mus musculus

<400> SEQUENCE: 28

```
gacattgagc tcacccagtc tccagcttct ttggctgtgt ctctagggca gagggccacc    60
atatcctgca gagccagtga aagtgttgat agttatggcg atagttttat gcactggtac    120
cagcagaacc aggacagcca cccaaactcc tcatctatcg tgcatccaac ctagaatctg    180
ggatcccagc caggtttagt ggcagtgggt ctgggacaga cttcacccte aacatccatc    240 ctgtggagga ggagatgctg caacctatta ctgtcagcaa agtcatgggg atccgtacac    300
gttcggaggg gggaccaagc tggagctgaa acgg                                334
```

<210> SEQ ID NO 29
<211> LENGTH: 367
<212> TYPE: DNA
<213> ORGANISM: Mus musculus

<400> SEQUENCE: 29

```
gaggtccagc tgcaacaatc tgcagctgaa ctggcaagac ctggggcctc agtgaagatg    60
tcctgcaagg cttctggcta cacctttagt aggtacacga tgcactgggt aaaacagagg    120
cctggacggg tctggaatgg attggattca ttaatcctaa cagtggatat actgactaca    180
atcagaagtt caaggacagg accacattga ctgcagacaa atcctccagc acagcctaca    240
ttcaactgac cagctgacat ctgaggactc tgcggtctat tactgtgcaa gacacccat     300 ctactctgat tacggcccct atgctatgga ctactgggt caaggaacct cagtcaccgt     360
ctcctca                                                              367
```

<210> SEQ ID NO 30
<211> LENGTH: 334
<212> TYPE: DNA
<213> ORGANISM: Mus musculus

<400> SEQUENCE: 30

```
gatattgtgc taacacagtc tccagcttct ttggctgtgt ctctagggca gagggccacc    60
atatcctgca gagccagtga aagtgttgat agttatggca atagttttat gcactggtac   120
cagcagaacc aggacagcca cccaaactcc tcatctatct tgcatccaac ctagaatctg   180
gggtccctgc caggttcagt ggcagtgggt ctaggacaga cttcacccctc accattgatc   240 ctgtggaggc tgatatgctg caacctatta ctgtcagcaa aataatgagg atccgtggac   300
gttcggtgga ggcaccaagc tggaaatcaa acgg                               334
```

<210> SEQ ID NO 31
<211> LENGTH: 355
<212> TYPE: DNA
<213> ORGANISM: Mus musculus

<400> SEQUENCE: 31

```
gaggtgcaac tggtggaatc tgggggaggc ttagtgcagc ctggagggtc cctgaaactc    60
tcctgtgcag cctctggatt cactttcagt gactattaca tgtattgggt tcgccagact   120
ccggaaagag gctggagtgg gtcgcaacca ttagtgatgg tggtgattac acctactatc   180
ctgacagtgt gaaggggcga ttcaccatct ccagagacaa tgccaagaac aacctgtacc   240
tgcaaatgag cagttgaagt ctgaggacac agccatgtat tactgtgcaa gagagggaga   300
ttactacggc ccgtttgctt actggggcca aggcaccact ctcacagtct cctca        355
```

<210> SEQ ID NO 32
<211> LENGTH: 322
<212> TYPE: DNA
<213> ORGANISM: Mus musculus

<400> SEQUENCE: 32

```
gacattgtga tgacccagtc tcaaaaattc atgtccacat cagtaggaga cagggtcagc    60
atcacctgca aggccagtca gaatgtgggt actgctgtag cctggtatca acagaaacca   120
ggacaattcc taaagcactg atttactcgg catcctaccg gtacagtgga gtccctgatc   180
gcttcacagg cagtggatct gggacagatt tcactctcac catcagcaat gtgcagtctg   240
aagacttggc agagatttct gtcagcaata taacagctat ccgtacacgt tcggaggggg   300
gaccaagctg gaaataaaac gg                                            322
```

<210> SEQ ID NO 33
<211> LENGTH: 355
<212> TYPE: DNA
<213> ORGANISM: Mus musculus

<400> SEQUENCE: 33

```
caggtccagc tgcagcagtc tggggctgag ctggtgaggc ctgggtctc agtgaaaatt     60 tcctgcaagg gttctggcta cacattcact gattattcta tacactgggt gaagcagagt   120
catgcaagag tctagagtgg attggagtta ttagctctta ctatggtgat gctaggcaca   180
accagaagtt caagggcaag gccacaatga ctgtagacaa atcctccagc acagcctata   240
tggaacttgc cagatgacat ctgaggattc tgccatctat tactgtgcaa gagatgggta   300
ctacggctac gctatggact actggggtca aggaacttca gtcaccgtct cctca        355
```

<210> SEQ ID NO 34
<211> LENGTH: 337
<212> TYPE: DNA

<213> ORGANISM: Mus musculus

<400> SEQUENCE: 34

```
gatgttgtga tgacccaaac tccactctcc ctgcctgtca gtcttggaga tcaagcctcc      60
atctcttgca gatctactca gagccttgta cacagtaatg gaaacaccta tttacattgg    120
tacctgcgaa gccaggccag tctccaaagc tcctgatcta caaagtttcc taccgatttt    180
ctggggtccc agacaggttc agtggcagtg gatcagggac agatttcaca ctcaagatca    240
gcagagtgga ggctaggatc tgggagttta tttctgctct caaagtacac atgttccatt    300
cacgttcggc tcggggacaa agttggaaat aaaacgt                             337
```

<210> SEQ ID NO 35
<211> LENGTH: 355
<212> TYPE: DNA
<213> ORGANISM: Mus musculus

<400> SEQUENCE: 35

```
gaggtcctgc tgcaacagtc tggacctgag ctggtgaagc ctggggcttc agtgaagata     60
tcctgcaagg cttctggata cacattcact gactacaaca tggactgggt gaagcagagc    120
catggaagag ccttgagtgg attggggata ttaatcctaa cgttggtgat actatctaca    180
accagaagtt caagggcaag gccacattga ctgttgacaa gtcctccagc acagcctaca    240
tggagctccg cagctgactt ctgaggacac tgcagtctat tactgtgtaa gaagtgatga    300
taactactcc tggttcactt actggggcca agggactctg gtcactgtct ctgca         355
```

<210> SEQ ID NO 36
<211> LENGTH: 322
<212> TYPE: DNA
<213> ORGANISM: Mus musculus

<400> SEQUENCE: 36

```
agtattgtga tgacccagac tcccaaattc ctgcttgtat cagcaggaga cagggttacc     60
ataacctgca aggccagtca gagtgtgagt aatgatgtag cctggtacca acagaagtca    120
gggcagttcc taaattgttg atatattatg catccaatcg ctatactgga gtccctgatc    180
gtttcactgg cagtggatat gggacggatt tcactttcac catcagcact gtgcaggctg    240
aagacctggc agttatttct gtcagcagga ttcgagctct ccgctcacgt tcggtgctgg    300
gaccaagctg gagctgaaaac gt                                            322
```

<210> SEQ ID NO 37
<211> LENGTH: 355
<212> TYPE: DNA
<213> ORGANISM: Mus musculus

<400> SEQUENCE: 37

```
gaggtcctgc tgcaacagtc tggacctgaa ctggtgaagc ctggggcttc agtgaagata     60
ccctgcaagg cttctggata cacattcact gactacaaca tggactgggt gaagcagagc    120
catggaagag ccttgagtgg attggagata ttaatcctaa caatggtgat actatctaca    180
accagaactt caaggacaag gccacattga ctgtcaacaa gtcctccagt acagcctaca    240
tggagctccg cagctgacat ctgaagactc tgcagtctat tactgtgtaa gaagtgatga    300
tgactactcc tggtttgctc actggggcca agggactctg gtcactgtct ctgca         355
```

<210> SEQ ID NO 38
<211> LENGTH: 322

```
<212> TYPE: DNA
<213> ORGANISM: Mus musculus

<400> SEQUENCE: 38
agtattgtga tgacccagac tcccaaattc ctgcttgtat cagcaggaga cagggttacc    60
ataacctgca aggccagtca gagtgtgagt aatgatgtag cctggtacca acagaagtca   120
gggcagttcc taaattgttg atatattatg catccaatcg ctatactgga gtccctgatc   180
gtttcactgg cagtggatat gggacggatt tcactttcac catcagcact gtgcaggctg   240
aagacctggc agttatttct gtcagcagga ttcgagctct ccgctcacgt tcggtgctgg   300
gaccaagctg gagctgaaac gt                                            322

<210> SEQ ID NO 39
<211> LENGTH: 120
<212> TYPE: PRT
<213> ORGANISM: Mus musculus

<400> SEQUENCE: 39
```

Gln Val Gln Leu Gln Gln Ser Gly Pro Asp Leu Val Lys Pro Gly Ser
1               5                   10                  15

Leu Val Lys Ile Ser Cys Lys Ala Ser Gly Tyr Thr Phe Ser Asn Tyr
            20                  25                  30

Asp Ile Asn Trp Val Arg Gln Arg Pro Gly Gln Gly Leu Glu Trp Ile
        35                  40                  45

Gly Trp Ile Asp Pro Gly Asn Gly Arg Thr Lys Tyr Asn Glu Lys Phe
    50                  55                  60

Glu Gly Lys Ala Ser Leu Thr Ala Asp Lys Ser Ser Thr Ala Phe
65                  70                  75                  80

Met Leu Leu Ser Ser Leu Thr Ser Asp Asn Ser Ala Val Tyr Phe Cys
                85                  90                  95

Ala Arg Val Gly Asp Asp Tyr Asp Gly Gly Phe Asp Tyr Trp Gly Gln
            100                 105                 110

Gly Thr Thr Val Thr Val Ser Ser
        115                 120

```
<210> SEQ ID NO 40
<211> LENGTH: 112
<212> TYPE: PRT
<213> ORGANISM: Mus musculus

<400> SEQUENCE: 40
```

Asp Ile Glu Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Arg Ala Ser Asn Leu Glu Ser Gly Ile Pro Val
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Tyr Pro Tyr Thr Phe Gly Gly Gly Thr Lys Leu Glu Leu Lys Arg
            100                 105                 110

<210> SEQ ID NO 41
<211> LENGTH: 120
<212> TYPE: PRT
<213> ORGANISM: Mus musculus

<400> SEQUENCE: 41

Gln Val Lys Leu Gln Gln Ser Gly Pro Asp Leu Val Lys Pro Gly Ser
1               5                   10                  15

Leu Val Lys Ile Ser Cys Lys Ala Ser Gly Tyr Thr Phe Ser Asn Tyr
            20                  25                  30

Asp Ile Asn Trp Val Lys Gln Arg Pro Gly Gln Gly Leu Glu Trp Ile
        35                  40                  45

Gly Trp Ile Asp Pro Gly Asn Gly Arg Thr Lys Tyr Asn Glu Lys Phe
    50                  55                  60

Glu Gly Lys Ala Ser Leu Thr Ala Asp Lys Ser Ser Ser Thr Ala Phe
65                  70                  75                  80

Met Leu Leu Ser Ser Leu Thr Ser Asp Ser Ala Val Tyr Phe Cys
                85                  90                  95

Ala Arg Val Gly Asp Asp Tyr Asp Gly Phe Asp Tyr Trp Gly Gln
            100                 105                 110

Gly Thr Thr Val Thr Val Ser Ser
        115                 120

<210> SEQ ID NO 42
<211> LENGTH: 112
<212> TYPE: PRT
<213> ORGANISM: Mus musculus

<400> SEQUENCE: 42

Asp Ile Glu Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Ser Pro
        35                  40                  45

Lys Leu Leu Ile Tyr Arg Thr Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Tyr
                85                  90                  95

Glu Glu Pro Tyr Thr Phe Gly Gly Thr Lys Leu Glu Leu Lys Arg
            100                 105                 110

<210> SEQ ID NO 43
<211> LENGTH: 120
<212> TYPE: PRT
<213> ORGANISM: Mus musculus

<400> SEQUENCE: 43

Gln Val Lys Leu Gln Gln Ser Gly Pro Asp Leu Val Lys Pro Gly Ser
1               5                   10                  15

Leu Val Lys Ile Ser Cys Lys Ala Ser Gly Tyr Thr Phe Ser Asn Tyr
            20                  25                  30

Asp Ile Asn Trp Val Lys Gln Arg Pro Gly Gln Gly Leu Glu Trp Ile
        35                  40                  45

Gly Trp Ile Asp Pro Gly Asn Gly Arg Thr Lys Tyr Asn Glu Lys Phe
    50                  55                  60

```
Glu Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Gly Asp Asp Tyr Asp Gly Asp Phe Asp Tyr Trp Gly Gln
                100                 105                 110

Gly Thr Thr Val Thr Val Ser Ser
            115                 120

<210> SEQ ID NO 44
<211> LENGTH: 112
<212> TYPE: PRT
<213> ORGANISM: Mus musculus

<400> SEQUENCE: 44

Asp Ile Glu Leu Thr Gln Ser Pro Thr Ile Met Ser Ala Ser Pro Gly
1               5                   10                  15

Glu Lys Val Thr Met Thr Cys Arg Ala Ser Glu Ser Val Asp Ser Tyr
                20                  25                  30

Gly Asn Ser Phe Met His Trp Tyr Gln Gln Lys Pro Gly Leu Pro Pro
            35                  40                  45

Lys Leu Leu Ile Tyr Arg Ala Ser Asn Leu Glu Ser Gly Ile Pro Ala
50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Tyr Pro Tyr Thr Phe Gly Gly Gly Thr Lys Leu Glu Ile Lys Arg
                100                 105                 110

<210> SEQ ID NO 45
<211> LENGTH: 120
<212> TYPE: PRT
<213> ORGANISM: Mus musculus

<400> SEQUENCE: 45

Gln Val Gln Leu Gln Gln Ser Gly Pro Asp Leu Val Lys Pro Gly Ala
1               5                   10                  15

Leu Val Lys Ile Ser Cys Lys Ala Ser Gly Tyr Ser Phe Thr Asn Tyr
                20                  25                  30

Asp Ile Asn Trp Val Lys Gln Arg Pro Gly Gln Gly Leu Glu Trp Ile
            35                  40                  45

Gly Trp Ile Asp Pro Gly Asn Gly Arg Thr Lys Tyr Asn Glu Lys Phe
50                  55                  60

Thr Gly Lys Ala Ser Leu Thr Ala Asp Lys Ser Ser Thr Ala Tyr
65                  70                  75                  80

Met Val Leu Ser Ser Leu Thr Ser Glu Asn Ser Ala Val Tyr Phe Cys
                85                  90                  95

Ala Arg Val Gly Asp Asp Tyr Asp Gly Gly Phe Asp Tyr Trp Gly Gln
                100                 105                 110

Gly Thr Thr Val Thr Val Ser Ser
            115                 120

<210> SEQ ID NO 46
<211> LENGTH: 109
<212> TYPE: PRT
<213> ORGANISM: Mus musculus
```

<400> SEQUENCE: 46

Asp Ile Glu Leu Thr Gln Ser Pro Ser Ile Met Ala Ala Ser Leu Gly
1               5                   10                  15

Gln Lys Val Thr Met Thr Cys Ser Ala Ser Ser Ser Val Ser Ser Ser
            20                  25                  30

Tyr Leu His Trp Tyr Gln Gln Lys Ser Gly Ala Ser Pro Lys Pro Leu
        35                  40                  45

Ile His Arg Thr Ser Asn Leu Ala Ser Gly Val Pro Ala Arg Phe Ser
    50                  55                  60

Gly Ser Gly Ser Gly Asn Ser Tyr Ser Leu Thr Ile Ser Ser Met Glu
65                  70                  75                  80

Ala Glu Asp Val Ala Thr Tyr Tyr Cys Phe Gln Gly Ser Gly Tyr Pro
                85                  90                  95

Tyr Thr Phe Gly Gly Gly Thr Lys Leu Glu Ile Lys Arg
            100                 105

<210> SEQ ID NO 47
<211> LENGTH: 120
<212> TYPE: PRT
<213> ORGANISM: Mus musculus

<400> SEQUENCE: 47

Gln Val Lys Leu Gln Gln Ser Gly Pro Asp Leu Val Lys Pro Gly Ala
1               5                   10                  15

Leu Val Lys Ile Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Asp Pro Gly Asp Gly Arg Thr Lys Tyr Asn Glu Lys Phe
    50                  55                  60

Glu Gly Lys Ala Ser Leu Thr Ala Asp Lys Ser Ser Ser Thr Ala Tyr
65                  70                  75                  80

Met Leu Leu Ser Ser Leu Thr Ser Asp Asn Ser Ala Val Tyr Phe Cys
                85                  90                  95

Ala Arg Val Gly Asp Asp Tyr Asp Gly Phe Asp Tyr Trp Gly Gln
            100                 105                 110

Gly Thr Thr Val Thr Val Ser Ser
            115                 120

<210> SEQ ID NO 48
<211> LENGTH: 112
<212> TYPE: PRT
<213> ORGANISM: Mus musculus

<400> SEQUENCE: 48

Asp Ile Glu Leu Thr Gln Ser Pro Ala Ile Met Ser Ala Ser Pro Gly
1               5                   10                  15

Glu Lys Val Thr Ile Ser Cys Ser Ala Ser Glu Ser Val Asp Ser Tyr
            20                  25                  30

Gly Asn Ser Phe Met Asn Trp Tyr Gln Gln Lys Pro Gly Gln Pro Pro
        35                  40                  45

Lys Leu Leu Ile Tyr Arg Ala Ser Asn Leu Glu Ser Gly Ile Pro Val
    50                  55                  60

Arg Phe Ser Gly Gly Gly Ser Arg Thr Asp Phe Thr Leu Thr Ile Asn
65                  70                  75                  80

```
Pro Val Glu Ala Asp Asp Val Ala Thr Tyr Tyr Cys Gln Gln Ser Asn
                85                  90                  95

Glu Tyr Pro Tyr Thr Phe Gly Gly Gly Thr Lys Leu Glu Ile Lys Arg
            100                 105                 110
```

<210> SEQ ID NO 49
<211> LENGTH: 120
<212> TYPE: PRT
<213> ORGANISM: Mus musculus

<400> SEQUENCE: 49

```
Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Phe
                20                  25                  30

Asp Ile Asn Trp Val Lys Gln Arg Pro Gly Gln Gly Leu Glu Trp Ile
            35                  40                  45

Gly Trp Ile Asp Pro Gly Asn Gly Arg Thr Lys Tyr Asn Glu Lys Phe
    50                  55                  60

Glu Gly Lys Val Ser Leu Thr Ala Asp Lys Ser Ser Thr Ala Phe
65                  70                  75                  80

Met Leu Leu Ser Ser Leu Thr Ser Asp Asn Ser Ala Val Tyr Phe Cys
                85                  90                  95

Ala Arg Val Gly Asp Asp Tyr Asp Gly Gly Phe Asp Tyr Trp Gly Gln
            100                 105                 110

Gly Thr Thr Leu Thr Val Ser Ser
        115                 120
```

<210> SEQ ID NO 50
<211> LENGTH: 112
<212> TYPE: PRT
<213> ORGANISM: Mus musculus

<400> SEQUENCE: 50

```
Asp Ile Glu Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Tyr Met Asn Trp Tyr Gln Gln Lys Pro Gly Gln Pro Pro
            35                  40                  45

Lys Leu Phe Ile Phe Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Val Ala Thr Tyr Tyr Cys Gln Gln Ser Tyr
                85                  90                  95

Glu Glu Pro Tyr Thr Phe Gly Gly Gly Thr Lys Leu Glu Ile Lys Arg
            100                 105                 110
```

<210> SEQ ID NO 51
<211> LENGTH: 120
<212> TYPE: PRT
<213> ORGANISM: Mus musculus

<400> SEQUENCE: 51

```
Gln Val Gln Leu Gln Gln Ser Gly Pro Asp Leu Val Lys Pro Gly Ala
1               5                   10                  15

Ser Val Lys Ile Ser Cys Lys Ala Ser Gly Tyr Pro Phe Ala Ser Tyr
```

```
                20                  25                  30

Asp Leu Asn Trp Val Lys Gln Arg Pro Gly Gln Gly Leu Glu Trp Ile
            35                  40                  45

Gly Trp Ile Asp Pro Gly Asp Gly Arg Thr Lys Tyr Asn Glu Lys Phe
        50                  55                  60

Glu Gly Lys Ala Ser Leu Thr Ala Asp Lys Ser Ser Ser Thr Ala Tyr
 65                  70                  75                  80

Met Leu Leu Ser Ser Leu Thr Ser Asp Ser Ser Ala Val Tyr Phe Cys
                85                  90                  95

Thr Arg Val Gly Asp Asp Tyr Asp Gly Gly Phe Asp Tyr Trp Gly Gln
            100                 105                 110

Gly Thr Thr Leu Thr Val Ser Ser
            115                 120

<210> SEQ ID NO 52
<211> LENGTH: 112
<212> TYPE: PRT
<213> ORGANISM: Mus musculus

<400> SEQUENCE: 52

Asp Ile Val Met Thr Gln Ser Pro Thr Ser Leu Ala Val Ser Leu Gly
 1               5                  10                  15

Gln Arg Ala Thr Ile Ser Cys Arg Ala Ser Glu Ser Val Asp Ser Tyr
            20                  25                  30

Gly Asp Arg Phe Met Asn Trp Tyr Gln Gln Lys Pro Gly Gln Pro Pro
        35                  40                  45

Lys Leu Leu Ile Gln Arg Val Ser Asn Leu Arg Ser Gly Ile Pro Ala
    50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Asp Tyr
                85                  90                  95

Glu Glu Pro Tyr Thr Phe Gly Gly Gly Thr Lys Leu Glu Ile Ile Arg
            100                 105                 110

<210> SEQ ID NO 53
<211> LENGTH: 120
<212> TYPE: PRT
<213> ORGANISM: Mus musculus

<400> SEQUENCE: 53

Gln Val Lys Leu Gln Glu Ser Gly Ala Glu Leu Val Arg Pro Gly Thr
 1               5                  10                  15

Ser Val Lys Ile Ser Cys Lys Ala Ser Gly Tyr Thr Phe Thr Asn Tyr
            20                  25                  30

Asp Ile Asn Trp Val Lys Gln Arg Pro Gly Gln Gly Leu Glu Trp Ile
        35                  40                  45

Gly Trp Ile Asp Pro Gly Asp Gly Arg Thr Lys Tyr Asn Glu Asn Phe
    50                  55                  60

Lys Asp Lys Ala Ser Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Val Gly Asp Asp Tyr Asp Gly Gly Phe Asp Tyr Trp Gly Gln
            100                 105                 110

Gly Thr Thr Val Thr Val Ser Ser
```

<210> SEQ ID NO 54
<211> LENGTH: 112
<212> TYPE: PRT
<213> ORGANISM: Mus musculus

<400> SEQUENCE: 54

Asp Ile Glu Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Arg Leu Leu Ile Tyr Ala Ala Ser Asn Gln Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Tyr
                85                  90                  95

Glu Asp Pro Tyr Thr Phe Gly Gly Gly Thr Lys Leu Glu Leu Lys Arg
            100                 105                 110

<210> SEQ ID NO 55
<211> LENGTH: 120
<212> TYPE: PRT
<213> ORGANISM: Mus musculus

<400> SEQUENCE: 55

Gln Val Lys Leu Gln Glu Ser Gly Pro Asp Leu Val Lys Pro Gly Ala
1               5                   10                  15

Ser Val Lys Ile Ser Cys Lys Ala Ser Gly Tyr Thr Phe Thr Asn Tyr
            20                  25                  30

Asp Ile Asn Trp Val Lys Gln Arg Pro Gly Gln Gly Leu Glu Trp Ile
        35                  40                  45

Gly Trp Ile Asp Pro Gly Asp Gly Ser Thr Lys Tyr Asn Glu Lys Phe
    50                  55                  60

Lys Gly Lys Ala Ser Leu Thr Ala Asp Lys Ser Ser Ser Thr Ala Tyr
65                  70                  75                  80

Met Leu Leu Asn Ser Leu Thr Ser Glu Asp Ser Ala Val Tyr Phe Cys
                85                  90                  95

Ala Arg Val Gly Asn Asp Tyr Asp Gly Gly Phe Asp Tyr Trp Gly Gln
            100                 105                 110

Gly Thr Thr Val Thr Val Ser Ser
        115                 120

<210> SEQ ID NO 56
<211> LENGTH: 112
<212> TYPE: PRT
<213> ORGANISM: Mus musculus

<400> SEQUENCE: 56

Asp Ile Glu Leu Thr Gln Ser Pro Thr Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asp Ser Phe Met Tyr Trp Tyr Gln Gln Lys Pro Gly Gln Ala Pro
        35                  40                  45

-continued

Lys Leu Leu Ile Tyr Arg Thr Ser Asn Leu Glu Ser Gly Ile Pro Ala
              50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                     85                  90                  95

Glu Tyr Pro Tyr Thr Phe Gly Gly Gly Thr Lys Leu Glu Ile Lys Arg
                100                 105                 110

<210> SEQ ID NO 57
<211> LENGTH: 120
<212> TYPE: PRT
<213> ORGANISM: Mus musculus

<400> SEQUENCE: 57

Gln Val Gln Leu Gln Gln Ser Gly Ala Glu Leu Val Arg Pro Gly Thr
  1               5                  10                  15

Ser Val Lys Val Ser Cys Lys Ala Ser Gly Tyr Ala Phe Thr Asn Tyr
                 20                  25                  30

Leu Ile Glu Trp Val Lys Gln Arg Pro Gly Gln Gly Leu Glu Trp Ile
             35                  40                  45

Gly Val Ile Asn Pro Gly Ser Gly Gly Thr Asn Tyr Asn Glu Lys Phe
 50                  55                  60

Lys Gly Lys Ala Thr Leu Thr Ala Asp Lys Ser Ser Thr Ala Tyr
 65                  70                  75                  80

Met Gln Leu Ser Ser Leu Thr Ser Asp Asp Ser Ala Val Tyr Phe Cys
                 85                  90                  95

Ala Arg Glu Gly Glu Lys His Ser Tyr Tyr Phe Asp Tyr Trp Gly Gln
                100                 105                 110

Gly Thr Thr Leu Thr Val Ser Ser
            115                 120

<210> SEQ ID NO 58
<211> LENGTH: 112
<212> TYPE: PRT
<213> ORGANISM: Mus musculus

<400> SEQUENCE: 58

Asp Ile Val Leu Thr Gln Ser Pro Ala Ser Leu Ala Val Ser Leu Gly
  1               5                  10                  15

Gln Arg Ala Thr Ile Ser Cys Arg Ala Ser Glu Ser Val Asp Ser Tyr
                 20                  25                  30

Gly Asp Ser Phe Met His Trp Tyr Gln Gln Lys Pro Gly Gln Pro Pro
             35                  40                  45

Lys Leu Leu Ile Tyr Leu Ala Ser Asn Leu Glu Ser Gly Val Pro Ala
 50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Asn
                     85                  90                  95

Glu Asp Pro Pro Thr Phe Gly Gly Gly Thr Lys Leu Glu Ile Lys Arg
                100                 105                 110

<210> SEQ ID NO 59
<211> LENGTH: 117
<212> TYPE: PRT
<213> ORGANISM: Mus musculus -continued

<400> SEQUENCE: 59

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Ile Ser Pro Gly Asn Gly Asp Val Trp Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Trp Asn Tyr Gly Tyr Phe Asp Val Trp Gly Ala Gly Thr Thr
            100                 105                 110

Val Thr Val Ser Ser
        115
```

<210> SEQ ID NO 60
<211> LENGTH: 113
<212> TYPE: PRT
<213> ORGANISM: Mus musculus

<400> SEQUENCE: 60

```
Asp Ile Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg
```

<210> SEQ ID NO 61
<211> LENGTH: 116
<212> TYPE: PRT
<213> ORGANISM: Mus musculus

<400> SEQUENCE: 61

```
Gln Val Lys Leu Gln Glu Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Met Thr Ala Asp Thr Ser Ser Asn Thr Ala Tyr
```

```
                65                  70                  75                  80
Leu Gln Leu Ser Ser Leu Thr Ser Glu Asp Ser Ala Val Tyr Tyr Cys
                    85                  90                  95

Thr Ser Ser Asp Tyr Ala Met Asp Tyr Trp Gly Gln Gly Thr Thr Val
                100                 105                 110

Thr Val Ser Ser
        115

<210> SEQ ID NO 62
<211> LENGTH: 107
<212> TYPE: PRT
<213> ORGANISM: Mus musculus

<400> SEQUENCE: 62

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Tyr Trp Tyr Gln Gln Lys Pro Gly Ser Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Leu Thr
                85                  90                  95

Phe Gly Ser Gly Thr Lys Leu Glu Ile Lys Arg
                100                 105

<210> SEQ ID NO 63
<211> LENGTH: 120
<212> TYPE: PRT
<213> ORGANISM: Mus musculus

<400> SEQUENCE: 63

Gln Val Lys Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
                20                  25                  30

Tyr Met His Trp Val Lys Gln Arg Pro Glu Gln Gly Leu Glu Trp Ile
            35                  40                  45

Gly Trp Ile Asp Pro Glu Asn Gly Asn Thr Ile Tyr Asp Pro Lys Phe
        50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Ser Ala Val Tyr Phe Cys
                85                  90                  95

Ala Arg Val Gly Asp Asp Tyr Asp Gly Asp Phe Asp Tyr Trp Gly Gln
                100                 105                 110

Gly Thr Thr Val Thr Val Ser Ser
        115                 120

<210> SEQ ID NO 64
<211> LENGTH: 112
<212> TYPE: PRT
<213> ORGANISM: Mus musculus

<400> SEQUENCE: 64
```

```
Asp Ile Glu Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
                20                  25                  30

Gly Asp Ser Phe Met His Trp Tyr Gln Gln Lys Pro Gly Gln Pro Pro
            35                  40                  45

Lys Leu Leu Ile Tyr Arg Ala Ser Asn Leu Glu Ser Gly Ile Pro Ala
        50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Tyr
                85                  90                  95

Glu Asp Pro Tyr Thr Phe Gly Gly Gly Thr Lys Leu Glu Ile Lys Arg
            100                 105                 110
```

<210> SEQ ID NO 65
<211> LENGTH: 123
<212> TYPE: PRT
<213> ORGANISM: Mus musculus

<400> SEQUENCE: 65

```
Gln Val Lys Leu Gln Gln Ser Gly Ala Glu Ala Arg Pro Gly Ala
1               5                   10                  15

Ser Val Lys Met Ser Cys Lys Ala Ser Gly Tyr Thr Phe Thr Lys Tyr
                20                  25                  30

Thr Met His Trp Val Lys Gln Arg Pro Gly Gln Gly Leu Glu Trp Ile
            35                  40                  45

Gly Phe Ile Asn Pro Asn Ser Gly Tyr Thr Asp Tyr Asn Gln Lys Phe
        50                  55                  60

Lys Ala Arg Thr Thr Leu Thr Ala Asp Lys Ser Ser Thr Thr Ala Tyr
65                  70                  75                  80

Ile Gln Leu Ser Ser Leu Thr Ser Glu Asp Ser Ala Val Tyr Tyr Cys
                85                  90                  95

Ala Arg Tyr Pro Ile Tyr Ser Asp Tyr Gly Pro Tyr Ala Met Asp Tyr
            100                 105                 110

Trp Gly Gln Gly Thr Thr Val Thr Val Ser Ser
        115                 120
```

<210> SEQ ID NO 66
<211> LENGTH: 112
<212> TYPE: PRT
<213> ORGANISM: Mus musculus

<400> SEQUENCE: 66

```
Asp Ile Glu Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
                20                  25                  30

Gly Asp Ser Phe Met His Trp Tyr Gln Gln Lys Pro Gly Gln Pro Pro
            35                  40                  45

Lys Leu Leu Ile Tyr Arg Ala Ser Asn Leu Glu Ser Gly Ile Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser His
                85                  90                  95
```

-continued

Gly Asp Pro Tyr Thr Phe Gly Gly Thr Lys Leu Glu Leu Lys Arg
            100                 105                 110

<210> SEQ ID NO 67
<211> LENGTH: 123
<212> TYPE: PRT
<213> ORGANISM: Mus musculus

<400> SEQUENCE: 67

Glu Val Gln Leu Gln Gln Ser Ala Ala Glu Leu Ala Arg Pro Gly Ala
1               5                   10                  15

Ser Val Lys Met Ser Cys Lys Ala Ser Gly Tyr Thr Phe Ser Arg Tyr
                20                  25                  30

Thr Met His Trp Val Lys Gln Arg Pro Gly Gln Gly Leu Glu Trp Ile
            35                  40                  45

Gly Phe Ile Asn Pro Asn Ser Gly Tyr Thr Asp Tyr Asn Gln Lys Phe
        50                  55                  60

Lys Asp Arg Thr Thr Leu Thr Ala Asp Lys Ser Ser Thr Ala Tyr
65                  70                  75                  80

Ile Gln Leu Thr Ser Leu Thr Ser Glu Asp Ser Ala Val Tyr Tyr Cys
                85                  90                  95

Ala Arg His Pro Ile Tyr Ser Asp Tyr Gly Pro Tyr Ala Met Asp Tyr
            100                 105                 110

Trp Gly Gln Gly Thr Ser Val Thr Val Ser Ser
        115                 120

<210> SEQ ID NO 68
<211> LENGTH: 112
<212> TYPE: PRT
<213> ORGANISM: Mus musculus

<400> SEQUENCE: 68

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
                20                  25                  30

Gly Asn Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Trp Thr Phe Gly Gly Gly Thr Lys Leu Glu Ile Lys Arg
            100                 105                 110

<210> SEQ ID NO 69
<211> LENGTH: 119
<212> TYPE: PRT
<213> ORGANISM: Mus musculus

<400> SEQUENCE: 69

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Tyr
                20                  25                  30

```
Tyr Met Tyr Trp Val Arg Gln Thr Pro Glu Lys Arg Leu Glu Trp Val
             35                  40                  45

Ala Thr Ile Ser Asp Gly Gly Asp Tyr Thr Tyr Tyr Pro Asp Ser Val
 50                      55                  60

Lys Gly Arg Phe Thr Ile Ser Arg Asp Asn Ala Lys Asn Asn Leu Tyr
 65                  70                  75                  80

Leu Gln Met Ser Ser Leu Lys Ser Glu Asp Thr Ala Met Tyr Tyr Cys
                 85                  90                  95

Ala Arg Glu Gly Asp Tyr Tyr Gly Pro Phe Ala Tyr Trp Gly Gln Gly
            100                 105                 110

Thr Thr Leu Thr Val Ser Ser
            115

<210> SEQ ID NO 70
<211> LENGTH: 108
<212> TYPE: PRT
<213> ORGANISM: Mus musculus

<400> SEQUENCE: 70

Asp Ile Val Met Thr Gln Ser Gln Lys Phe Met Ser Thr Ser Val Gly
 1               5                  10                  15

Asp Arg Val Ser Ile Thr Cys Lys Ala Ser Gln Asn Val Gly Thr Ala
                 20                  25                  30

Val Ala Trp Tyr Gln Gln Lys Pro Gly Gln Ser Pro Lys Ala Leu Ile
             35                  40                  45

Tyr Ser Ala Ser Tyr Arg Tyr Ser Gly Val Pro Asp Arg Phe Thr Gly
 50                      55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Tyr
                 85                  90                  95

Thr Phe Gly Gly Gly Thr Lys Leu Glu Ile Lys Arg
            100                 105

<210> SEQ ID NO 71
<211> LENGTH: 119
<212> TYPE: PRT
<213> ORGANISM: Mus musculus

<400> SEQUENCE: 71

Gln Val Gln Leu Gln Gln Ser Gly Ala Glu Leu Val Arg Pro Gly Val
 1               5                  10                  15

Ser Val Lys Ile Ser Cys Lys Gly Ser Gly Tyr Thr Phe Thr Asp Tyr
                 20                  25                  30

Ser Ile His Trp Val Lys Gln Ser His Ala Lys Ser Leu Glu Trp Ile
             35                  40                  45

Gly Val Ile Ser Ser Tyr Tyr Gly Asp Ala Arg His Asn Gln Lys Phe
 50                      55                  60

Lys Gly Lys Ala Thr Met Thr Val Asp Lys Ser Ser Thr Ala Tyr
 65                  70                  75                  80

Met Glu Leu Ala Arg Leu Thr Ser Glu Asp Ser Ala Ile Tyr Tyr Cys
                 85                  90                  95

Ala Arg Asp Gly Tyr Tyr Gly Tyr Ala Met Asp Tyr Trp Gly Gln Gly
            100                 105                 110

Thr Ser Val Thr Val Ser Ser
            115
```

<210> SEQ ID NO 72
<211> LENGTH: 113
<212> TYPE: PRT
<213> ORGANISM: Mus musculus

<400> SEQUENCE: 72

Asp Val Val Met Thr Gln Thr Pro Leu Ser Leu Pro Val Ser Leu Gly
1               5                   10                  15

Asp Gln Ala Ser Ile Ser Cys Arg Ser Thr Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Tyr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

Arg

<210> SEQ ID NO 73
<211> LENGTH: 119
<212> TYPE: PRT
<213> ORGANISM: Mus musculus

<400> SEQUENCE: 73

Glu Val Leu Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Val Gly Asp Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Val Arg Ser Asp Asp Asp Tyr Ser Trp Phe Ala His Trp Gly Gln Gly
            100                 105                 110

Thr Leu Val Thr Val Ser Ala
        115

<210> SEQ ID NO 74
<211> LENGTH: 107
<212> TYPE: PRT
<213> ORGANISM: Mus musculus

<400> SEQUENCE: 74

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Ser Gly Gln Ser Pro Lys Leu Leu Ile
        35                  40                  45

Tyr Tyr Ala Ser Asn Arg Tyr Thr Gly Val Pro Asp Arg Phe Thr Gly
            50                  55                  60

Ser Gly Tyr Gly Thr Asp Phe Thr Phe Thr Ile Ser Thr Val Gln Ala
 65                  70                  75                  80

Glu Leu Ala Val Tyr Phe Cys Gln Gln Asp Ser Ser Ser Pro Leu Thr
                 85                  90                  95

Phe Gly Ala Gly Thr Lys Leu Glu Leu Lys Arg
            100                 105

<210> SEQ ID NO 75
<211> LENGTH: 119
<212> TYPE: PRT
<213> ORGANISM: Mus musculus

<400> SEQUENCE: 75

Glu Val Leu Leu Gln Gln Ser Gly Pro Glu Leu Val Lys Pro Gly Ala
 1               5                  10                  15

Ser Val Lys Ile Pro Cys Lys Ala Ser Gly Tyr Thr Phe Thr Asp Tyr
                20                  25                  30

Asn Met Asp Trp Val Lys Gln Ser His Gly Lys Ser Leu Glu Trp Ile
            35                  40                  45

Gly Asp Ile Asn Pro Asn Asn Gly Asp Thr Ile Tyr Asn Gln Asn Phe
    50                  55                  60

Lys Asp Lys Ala Thr Leu Thr Val Asn Lys Ser Ser Thr Ala Tyr
 65                  70                  75                  80

Met Glu Leu Arg Ser Leu Thr Ser Glu Asp Thr Ala Val Tyr Tyr Cys
                 85                  90                  95

Val Arg Ser Asp Asp Asn Tyr Ser Trp Phe Thr Tyr Trp Gly Gln Gly
                100                 105                 110

Thr Leu Val Thr Val Ser Ala
        115

<210> SEQ ID NO 76
<211> LENGTH: 107
<212> TYPE: PRT
<213> ORGANISM: Mus musculus

<400> SEQUENCE: 76

Ser Ile Val Met Thr Gln Thr Pro Lys Phe Leu Leu Val Ser Ala Gly
 1               5                  10                  15

Asp Arg Val Thr Ile Thr Cys Lys Ala Ser Gln Ser Val Ser Asn Asp
                20                  25                  30

Val Ala Trp Tyr Gln Gln Lys Ser Gly Gln Ser Pro Lys Leu Leu Ile
            35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
 65                  70                  75                  80

Glu Leu Ala Val Tyr Phe Cys Gln Gln Asp Ser Ser Ser Pro Leu Thr
                 85                  90                  95

Phe Gly Ala Gly Thr Lys Leu Glu Leu Lys Arg
            100                 105

<210> SEQ ID NO 77
<211> LENGTH: 74
<212> TYPE: PRT
<213> ORGANISM: Homo sapiens

<400> SEQUENCE: 77

Gly Arg Asp Tyr Arg Thr Cys Leu Thr Ile Val Gln Lys Leu Lys Lys
1               5                   10                  15

Met Val Asp Lys Pro Thr Gln Arg Ser Val Ser Asn Ala Ala Thr Arg
            20                  25                  30

Val Cys Arg Thr Gly Arg Ser Arg Trp Arg Asp Val Cys Arg Asn Phe
        35                  40                  45

Met Arg Arg Tyr Gln Ser Arg Val Thr Gln Gly Leu Val Ala Gly Glu
    50                  55                  60

Thr Ala Gln Gln Ile Cys Glu Asp Leu Arg
65                  70

<210> SEQ ID NO 78
<211> LENGTH: 222
<212> TYPE: DNA
<213> ORGANISM: Homo sapiens

<400> SEQUENCE: 78
ggccgtgact acaggacctg tctgacgata gtccaaaaac tgaagaagat ggtggataag      60
cccacccaga gaagtgtttc caatgctgcg acccgggtgt gtaggacggg gaggtcacga    120
tggcgcgacg tctgcagaaa tttcatgagg aggtatcagt ctagagttac ccagggcctc    180
gtggccggag aaactgccca gcagatctgt gaggacctca gg                       222

<210> SEQ ID NO 79
<211> LENGTH: 145
<212> TYPE: PRT
<213> ORGANISM: Homo sapiens

<400> SEQUENCE: 79

Met Ala Thr Trp Ala Leu Leu Leu Leu Ala Ala Met Leu Leu Gly Asn
1               5                   10                  15

Pro Gly Leu Val Phe Ser Arg Leu Ser Pro Glu Tyr Tyr Asp Leu Ala
            20                  25                  30

Arg Ala His Leu Arg Asp Glu Glu Lys Ser Cys Pro Cys Leu Ala Gln
        35                  40                  45

Glu Gly Pro Gln Gly Asp Leu Leu Thr Lys Thr Gln Glu Leu Gly Arg
    50                  55                  60

Asp Tyr Arg Thr Cys Leu Thr Ile Val Gln Lys Leu Lys Lys Met Val
65                  70                  75                  80

Asp Lys Pro Thr Gln Arg Ser Val Ser Asn Ala Ala Thr Arg Val Cys
                85                  90                  95

Arg Thr Gly Arg Ser Arg Trp Arg Asp Val Cys Arg Asn Phe Met Arg
            100                 105                 110

Arg Tyr Gln Ser Arg Val Thr Gln Gly Leu Val Ala Gly Glu Thr Ala
        115                 120                 125

Gln Gln Ile Cys Glu Asp Leu Arg Leu Cys Ile Pro Ser Thr Gly Pro
    130                 135                 140

Leu
145

<210> SEQ ID NO 80
<211> LENGTH: 438
<212> TYPE: DNA
<213> ORGANISM: Homo sapiens

<400> SEQUENCE: 80

```
atggctacct gggccctcct gctccttgca gccatgctcc tgggcaaccc aggtctggtc    60
ttctctcgtc tgagccctga gtactacgac ctggcaagag cccacctgcg tgatgaggag   120
aaatcctgcc cgtgcctggc ccaggagggc ccccagggtg acctgttgac caaaacacag   180
gagctgggcc gtgactacag gacctgtctg acgatagtcc aaaaactgaa gaagatggtg   240
gataagccca cccagagaag tgtttccaat gctgcgaccc gggtgtgtag gacggggagg   300
tcacgatggc gcgacgtctg cagaaatttc atgaggaggt atcagtctag agttacccag   360
ggcctcgtgg ccggagaaac tgcccagcag atctgtgagg acctcaggtt gtgtatacct   420
tctacaggtc ccctctga                                                 438
```

<210> SEQ ID NO 81
<211> LENGTH: 50
<212> TYPE: PRT
<213> ORGANISM: Homo sapiens

<400> SEQUENCE: 81

Arg Asp Tyr Arg Thr Cys Leu Thr Ile Val Gln Lys Leu Lys Lys Met
1               5                   10                  15
Val Asp Lys Pro Thr Gln Arg Ser Val Ser Asn Ala Ala Thr Arg Val
            20                  25                  30
Cys Arg Thr Gly Arg Ser Arg Trp Arg Asp Val Cys Arg Asn Phe Met
        35                  40                  45
Arg Arg
    50

<210> SEQ ID NO 82
<211> LENGTH: 10
<212> TYPE: PRT
<213> ORGANISM: Mus musculus

<400> SEQUENCE: 82

Gly Tyr Thr Phe Ser Asn Tyr Asp Ile Asn
1               5                   10

<210> SEQ ID NO 83
<211> LENGTH: 17
<212> TYPE: PRT
<213> ORGANISM: Mus musculus

<400> SEQUENCE: 83

Trp Ile Asp Pro Gly Asn Gly Arg Thr Lys Tyr Asn Glu Lys Phe Glu
1               5                   10                  15
Gly

<210> SEQ ID NO 84
<211> LENGTH: 11
<212> TYPE: PRT
<213> ORGANISM: Mus musculus

<400> SEQUENCE: 84

Val Gly Asp Asp Tyr Asp Gly Gly Phe Asp Tyr
1               5                   10

<210> SEQ ID NO 85
<211> LENGTH: 15
<212> TYPE: PRT
<213> ORGANISM: Mus musculus

<400> SEQUENCE: 85

```
Lys Ala Ser Gln Ser Val Asp Tyr Asp Gly Asp Ser Tyr Met Asn
1               5                   10                  15

<210> SEQ ID NO 86
<211> LENGTH: 7
<212> TYPE: PRT
<213> ORGANISM: Mus musculus

<400> SEQUENCE: 86

Arg Ala Ser Asn Leu Glu Ser
1               5

<210> SEQ ID NO 87
<211> LENGTH: 9
<212> TYPE: PRT
<213> ORGANISM: Mus musculus

<400> SEQUENCE: 87

Gln Gln Ser Asn Glu Tyr Pro Tyr Thr
1               5

<210> SEQ ID NO 88
<211> LENGTH: 10
<212> TYPE: PRT
<213> ORGANISM: Mus musculus

<400> SEQUENCE: 88

Gly Tyr Thr Phe Ser Asn Tyr Asp Ile Asn
1               5                   10

<210> SEQ ID NO 89
<211> LENGTH: 17
<212> TYPE: PRT
<213> ORGANISM: Mus musculus

<400> SEQUENCE: 89

Trp Ile Asp Pro Gly Asn Gly Arg Thr Lys Tyr Asn Glu Lys Phe Glu
1               5                   10                  15

Gly

<210> SEQ ID NO 90
<211> LENGTH: 11
<212> TYPE: PRT
<213> ORGANISM: Mus musculus

<400> SEQUENCE: 90

Val Gly Asp Asp Tyr Asp Gly Gly Phe Asp Tyr
1               5                   10

<210> SEQ ID NO 91
<211> LENGTH: 15
<212> TYPE: PRT
<213> ORGANISM: Mus musculus

<400> SEQUENCE: 91

Arg Ala Ser Glu Ser Val Asp Ser Tyr Gly Asn Ser Phe Met His
1               5                   10                  15

<210> SEQ ID NO 92
<211> LENGTH: 7
<212> TYPE: PRT
<213> ORGANISM: Mus musculus

<400> SEQUENCE: 92
```

```
Arg Thr Ser Asn Leu Glu Ser
1               5

<210> SEQ ID NO 93
<211> LENGTH: 9
<212> TYPE: PRT
<213> ORGANISM: Mus musculus

<400> SEQUENCE: 93

Gln Gln Ser Tyr Glu Glu Pro Tyr Thr
1               5

<210> SEQ ID NO 94
<211> LENGTH: 10
<212> TYPE: PRT
<213> ORGANISM: Mus musculus

<400> SEQUENCE: 94

Gly Tyr Thr Phe Ser Asn Tyr Asp Ile Asn
1               5                   10

<210> SEQ ID NO 95
<211> LENGTH: 17
<212> TYPE: PRT
<213> ORGANISM: Mus musculus

<400> SEQUENCE: 95

Trp Ile Asp Pro Gly Asn Gly Arg Thr Lys Tyr Asn Glu Lys Phe Glu
1               5                   10                  15
Asp

<210> SEQ ID NO 96
<211> LENGTH: 11
<212> TYPE: PRT
<213> ORGANISM: Mus musculus

<400> SEQUENCE: 96

Val Gly Asp Asp Tyr Asp Gly Asp Phe Asp Tyr
1               5                   10

<210> SEQ ID NO 97
<211> LENGTH: 15
<212> TYPE: PRT
<213> ORGANISM: Mus musculus

<400> SEQUENCE: 97

Arg Ala Ser Glu Ser Val Asp Ser Tyr Gly Asn Ser Phe Met His
1               5                   10                  15

<210> SEQ ID NO 98
<211> LENGTH: 7
<212> TYPE: PRT
<213> ORGANISM: Mus musculus

<400> SEQUENCE: 98

Arg Ala Ser Asn Leu Glu Ser
1               5

<210> SEQ ID NO 99
<211> LENGTH: 9
<212> TYPE: PRT
<213> ORGANISM: Mus musculus

<400> SEQUENCE: 99
```

```
Gln Gln Ser Asn Glu Tyr Pro Tyr Thr
1               5

<210> SEQ ID NO 100
<211> LENGTH: 10
<212> TYPE: PRT
<213> ORGANISM: Mus musculus

<400> SEQUENCE: 100

Gly Tyr Ser Phe Thr Asn Tyr Asp Ile Asn
1               5                   10

<210> SEQ ID NO 101
<211> LENGTH: 17
<212> TYPE: PRT
<213> ORGANISM: Mus musculus

<400> SEQUENCE: 101

Trp Ile Asp Pro Gly Asn Gly Arg Thr Lys Tyr Asn Glu Lys Phe Thr
1               5                   10                  15

Gly

<210> SEQ ID NO 102
<211> LENGTH: 11
<212> TYPE: PRT
<213> ORGANISM: Mus musculus

<400> SEQUENCE: 102

Val Gly Asp Asp Tyr Asp Gly Gly Phe Asp Tyr
1               5                   10

<210> SEQ ID NO 103
<211> LENGTH: 12
<212> TYPE: PRT
<213> ORGANISM: Mus musculus

<400> SEQUENCE: 103

Ser Ala Ser Ser Ser Val Ser Ser Ser Tyr Leu His
1               5                   10

<210> SEQ ID NO 104
<211> LENGTH: 7
<212> TYPE: PRT
<213> ORGANISM: Mus musculus

<400> SEQUENCE: 104

Arg Thr Ser Asn Leu Ala Ser
1               5

<210> SEQ ID NO 105
<211> LENGTH: 9
<212> TYPE: PRT
<213> ORGANISM: Mus musculus

<400> SEQUENCE: 105

Phe Gln Gly Ser Gly Tyr Pro Tyr Thr
1               5

<210> SEQ ID NO 106
<211> LENGTH: 10
<212> TYPE: PRT
<213> ORGANISM: Mus musculus

<400> SEQUENCE: 106
```

Gly Tyr Thr Phe Thr Ser Tyr Asp Ile Asn
1               5                   10

<210> SEQ ID NO 107
<211> LENGTH: 17
<212> TYPE: PRT
<213> ORGANISM: Mus musculus

<400> SEQUENCE: 107

Trp Ile Asp Pro Gly Asp Gly Arg Thr Lys Tyr Asn Glu Lys Phe Glu
1               5                   10                  15

Gly

<210> SEQ ID NO 108
<211> LENGTH: 11
<212> TYPE: PRT
<213> ORGANISM: Mus musculus

<400> SEQUENCE: 108

Val Gly Asp Asp Tyr Asp Gly Gly Phe Asp Tyr
1               5                   10

<210> SEQ ID NO 109
<211> LENGTH: 15
<212> TYPE: PRT
<213> ORGANISM: Mus musculus

<400> SEQUENCE: 109

Ser Ala Ser Glu Ser Val Asp Ser Tyr Gly Asn Ser Phe Met Asn
1               5                   10                  15

<210> SEQ ID NO 110
<211> LENGTH: 7
<212> TYPE: PRT
<213> ORGANISM: Mus musculus

<400> SEQUENCE: 110

Arg Ala Ser Asn Leu Glu Ser
1               5

<210> SEQ ID NO 111
<211> LENGTH: 9
<212> TYPE: PRT
<213> ORGANISM: Mus musculus

<400> SEQUENCE: 111

Gln Gln Ser Asn Glu Tyr Pro Tyr Thr
1               5

<210> SEQ ID NO 112
<211> LENGTH: 10
<212> TYPE: PRT
<213> ORGANISM: Mus musculus

<400> SEQUENCE: 112

Gly Tyr Thr Phe Thr Ser Phe Asp Ile Asn
1               5                   10

<210> SEQ ID NO 113
<211> LENGTH: 17
<212> TYPE: PRT
<213> ORGANISM: Mus musculus

<400> SEQUENCE: 113

Trp Ile Asp Pro Gly Asn Gly Arg Thr Lys Tyr Asn Glu Lys Phe Glu
1               5                   10                  15

Gly

<210> SEQ ID NO 114
<211> LENGTH: 11
<212> TYPE: PRT
<213> ORGANISM: Mus musculus

<400> SEQUENCE: 114

Val Gly Asp Asp Tyr Asp Gly Gly Phe Asp Tyr
1               5                   10

<210> SEQ ID NO 115
<211> LENGTH: 15
<212> TYPE: PRT
<213> ORGANISM: Mus musculus

<400> SEQUENCE: 115

Lys Ala Ser Gln Ser Val Asp Tyr Asp Gly Asp Ser Tyr Met Asn
1               5                   10                  15

<210> SEQ ID NO 116
<211> LENGTH: 7
<212> TYPE: PRT
<213> ORGANISM: Mus musculus

<400> SEQUENCE: 116

Leu Ala Ser Asn Leu Glu Ser
1               5

<210> SEQ ID NO 117
<211> LENGTH: 9
<212> TYPE: PRT
<213> ORGANISM: Mus musculus

<400> SEQUENCE: 117

Gln Gln Ser Tyr Glu Glu Pro Tyr Thr
1               5

<210> SEQ ID NO 118
<211> LENGTH: 10
<212> TYPE: PRT
<213> ORGANISM: Mus musculus

<400> SEQUENCE: 118

Gly Tyr Pro Phe Ala Ser Tyr Asp Leu Asn
1               5                   10

<210> SEQ ID NO 119
<211> LENGTH: 17
<212> TYPE: PRT
<213> ORGANISM: Mus musculus

<400> SEQUENCE: 119

Trp Ile Asp Pro Gly Asp Gly Arg Thr Lys Tyr Asn Glu Lys Phe Glu
1               5                   10                  15

Gly

<210> SEQ ID NO 120
<211> LENGTH: 11
<212> TYPE: PRT
<213> ORGANISM: Mus musculus

```
<400> SEQUENCE: 120

Val Gly Asp Asp Tyr Asp Gly Gly Phe Asp Tyr
1               5                   10

<210> SEQ ID NO 121
<211> LENGTH: 15
<212> TYPE: PRT
<213> ORGANISM: Mus musculus

<400> SEQUENCE: 121

Arg Ala Ser Glu Ser Val Asp Ser Tyr Gly Asp Arg Phe Met Asn
1               5                   10                  15

<210> SEQ ID NO 122
<211> LENGTH: 7
<212> TYPE: PRT
<213> ORGANISM: Mus musculus

<400> SEQUENCE: 122

Arg Val Ser Asn Leu Arg Ser
1               5

<210> SEQ ID NO 123
<211> LENGTH: 9
<212> TYPE: PRT
<213> ORGANISM: Mus musculus

<400> SEQUENCE: 123

Gln Gln Asp Tyr Glu Glu Pro Tyr Thr
1               5

<210> SEQ ID NO 124
<211> LENGTH: 10
<212> TYPE: PRT
<213> ORGANISM: Mus musculus

<400> SEQUENCE: 124

Gly Tyr Thr Phe Thr Asn Tyr Asp Ile Asn
1               5                   10

<210> SEQ ID NO 125
<211> LENGTH: 17
<212> TYPE: PRT
<213> ORGANISM: Mus musculus

<400> SEQUENCE: 125

Trp Ile Asp Pro Gly Asp Gly Arg Thr Lys Tyr Asn Glu Asn Phe Lys
1               5                   10                  15

Asp

<210> SEQ ID NO 126
<211> LENGTH: 11
<212> TYPE: PRT
<213> ORGANISM: Mus musculus

<400> SEQUENCE: 126

Val Gly Asp Asp Tyr Asp Gly Gly Phe Asp Tyr
1               5                   10

<210> SEQ ID NO 127
<211> LENGTH: 15
<212> TYPE: PRT
<213> ORGANISM: Mus musculus
```

<400> SEQUENCE: 127

Arg Ala Ser Glu Ser Val Asp Ser Tyr Gly Asn Ser Phe Met His
1               5                   10                  15

<210> SEQ ID NO 128
<211> LENGTH: 7
<212> TYPE: PRT
<213> ORGANISM: Mus musculus

<400> SEQUENCE: 128

Ala Ala Ser Asn Gln Glu Ser
1               5

<210> SEQ ID NO 129
<211> LENGTH: 9
<212> TYPE: PRT
<213> ORGANISM: Mus musculus

<400> SEQUENCE: 129

Gln Gln Ser Tyr Glu Asp Pro Tyr Thr
1               5

<210> SEQ ID NO 130
<211> LENGTH: 10
<212> TYPE: PRT
<213> ORGANISM: Mus musculus

<400> SEQUENCE: 130

Gly Tyr Thr Phe Thr Asn Tyr Asp Ile Asn
1               5                   10

<210> SEQ ID NO 131
<211> LENGTH: 17
<212> TYPE: PRT
<213> ORGANISM: Mus musculus

<400> SEQUENCE: 131

Trp Ile Asp Pro Gly Asp Gly Ser Thr Lys Tyr Asn Glu Lys Phe Lys
1               5                   10                  15
Gly

<210> SEQ ID NO 132
<211> LENGTH: 11
<212> TYPE: PRT
<213> ORGANISM: Mus musculus

<400> SEQUENCE: 132

Val Gly Asn Asp Tyr Asp Gly Gly Phe Asp Phe
1               5                   10

<210> SEQ ID NO 133
<211> LENGTH: 15
<212> TYPE: PRT
<213> ORGANISM: Mus musculus

<400> SEQUENCE: 133

Arg Ala Ser Glu Ser Val Asp Ser Tyr Gly Asp Ser Phe Met Tyr
1               5                   10                  15

<210> SEQ ID NO 134
<211> LENGTH: 7
<212> TYPE: PRT
<213> ORGANISM: Mus musculus
<210> SEQ ID NO 135
<211> LENGTH: 9
<212> TYPE: PRT
<213> ORGANISM: Mus musculus

<400> SEQUENCE: 134

Arg Thr Ser Asn Leu Glu Ser
1               5

<210> SEQ ID NO 135
<211> LENGTH: 9
<212> TYPE: PRT
<213> ORGANISM: Mus musculus

<400> SEQUENCE: 135

Gln Gln Ser Asn Glu Tyr Pro Tyr Thr
1               5

<210> SEQ ID NO 136
<211> LENGTH: 10
<212> TYPE: PRT
<213> ORGANISM: Mus musculus

<400> SEQUENCE: 136

Gly Tyr Ala Phe Thr Asn Tyr Leu Ile Glu
1               5                   10

<210> SEQ ID NO 137
<211> LENGTH: 17
<212> TYPE: PRT
<213> ORGANISM: Mus musculus

<400> SEQUENCE: 137

Val Ile Asn Pro Gly Ser Gly Gly Thr Asn Tyr Asn Glu Lys Phe Lys
1               5                   10                  15

Gly

<210> SEQ ID NO 138
<211> LENGTH: 11
<212> TYPE: PRT
<213> ORGANISM: Mus musculus

<400> SEQUENCE: 138

Glu Gly Glu Lys His Ser Tyr Tyr Phe Asp Tyr
1               5                   10

<210> SEQ ID NO 139
<211> LENGTH: 15
<212> TYPE: PRT
<213> ORGANISM: Mus musculus

<400> SEQUENCE: 139

Arg Ala Ser Glu Ser Val Asp Ser Tyr Gly Asp Ser Phe Met His
1               5                   10                  15

<210> SEQ ID NO 140
<211> LENGTH: 7
<212> TYPE: PRT
<213> ORGANISM: Mus musculus

<400> SEQUENCE: 140

Leu Ala Ser Asn Leu Glu Ser
1               5

<210> SEQ ID NO 141
<211> LENGTH: 9
<212> TYPE: PRT
<213> ORGANISM: Mus musculus

<400> SEQUENCE: 141

Gln Gln Asn Asn Glu Asp Pro Pro Thr
1               5

<210> SEQ ID NO 142
<211> LENGTH: 10
<212> TYPE: PRT
<213> ORGANISM: Mus musculus

<400> SEQUENCE: 142

Gly Tyr Thr Phe Thr Asp His Ala Ile His
1               5                   10

<210> SEQ ID NO 143
<211> LENGTH: 17
<212> TYPE: PRT
<213> ORGANISM: Mus musculus

<400> SEQUENCE: 143

Tyr Ile Ser Pro Gly Asn Gly Asp Val Trp Tyr Asn Glu Lys Phe Lys
1               5                   10                  15

Gly

<210> SEQ ID NO 144
<211> LENGTH: 8
<212> TYPE: PRT
<213> ORGANISM: Mus musculus

<400> SEQUENCE: 144

Trp Asn Tyr Gly Tyr Phe Asp Val
1               5

<210> SEQ ID NO 145
<211> LENGTH: 16
<212> TYPE: PRT
<213> ORGANISM: Mus musculus

<400> SEQUENCE: 145

Arg Ser Ser Gln Ser Leu Val His Ser Asn Gly Asn Thr Tyr Leu His
1               5                   10                  15

<210> SEQ ID NO 146
<211> LENGTH: 7
<212> TYPE: PRT
<213> ORGANISM: Mus musculus

<400> SEQUENCE: 146

Lys Val Ser Asn Arg Phe Ser
1               5

<210> SEQ ID NO 147
<211> LENGTH: 9
<212> TYPE: PRT
<213> ORGANISM: Mus musculus

<400> SEQUENCE: 147

Ser Gln Ser Thr His Val Pro Trp Thr
1               5

<210> SEQ ID NO 148
<211> LENGTH: 10
<212> TYPE: PRT
<213> ORGANISM: Mus musculus

<400> SEQUENCE: 148

Gly Phe Asn Ile Lys Asp Tyr Tyr Met His
1               5                   10

<210> SEQ ID NO 149
<211> LENGTH: 17
<212> TYPE: PRT
<213> ORGANISM: Mus musculus

<400> SEQUENCE: 149

Trp Ile Asp Pro Glu Asn Gly Asp Thr Glu Tyr Ala Pro Lys Phe Gln
1               5                   10                  15

Gly

<210> SEQ ID NO 150
<211> LENGTH: 7
<212> TYPE: PRT
<213> ORGANISM: Mus musculus

<400> SEQUENCE: 150

Ser Asp Tyr Ala Met Asp Tyr
1               5

<210> SEQ ID NO 151
<211> LENGTH: 10
<212> TYPE: PRT
<213> ORGANISM: Mus musculus

<400> SEQUENCE: 151

Ser Ala Ser Ser Ser Val Ser Tyr Met Tyr
1               5                   10

<210> SEQ ID NO 152
<211> LENGTH: 7
<212> TYPE: PRT
<213> ORGANISM: Mus musculus

<400> SEQUENCE: 152

Asp Thr Ser Asn Leu Ala Ser
1               5

<210> SEQ ID NO 153
<211> LENGTH: 9
<212> TYPE: PRT
<213> ORGANISM: Mus musculus

<400> SEQUENCE: 153

Gln Gln Trp Ser Ser Tyr Pro Leu Thr
1               5

<210> SEQ ID NO 154
<211> LENGTH: 10
<212> TYPE: PRT
<213> ORGANISM: Mus musculus

<400> SEQUENCE: 154

Gly Phe Asn Ile Lys Asp Tyr Tyr Met His
1               5                   10

<210> SEQ ID NO 155
<211> LENGTH: 17
<212> TYPE: PRT
<213> ORGANISM: Mus musculus

<400> SEQUENCE: 155

Trp Ile Asp Pro Glu Asn Gly Asn Thr Ile Tyr Asp Pro Lys Phe Gln
1               5                   10                  15
Gly

<210> SEQ ID NO 156
<211> LENGTH: 11
<212> TYPE: PRT
<213> ORGANISM: Mus musculus

<400> SEQUENCE: 156

Val Gly Asp Asp Tyr Asp Gly Asp Phe Asp Tyr
1               5                   10

<210> SEQ ID NO 157
<211> LENGTH: 15
<212> TYPE: PRT
<213> ORGANISM: Mus musculus

<400> SEQUENCE: 157

Arg Ala Ser Glu Ser Val Asp Ser Tyr Gly Asp Ser Phe Met His
1               5                   10                  15

<210> SEQ ID NO 158
<211> LENGTH: 7
<212> TYPE: PRT
<213> ORGANISM: Mus musculus

<400> SEQUENCE: 158

Arg Ala Ser Asn Leu Glu Ser
1               5

<210> SEQ ID NO 159
<211> LENGTH: 9
<212> TYPE: PRT
<213> ORGANISM: Mus musculus

<400> SEQUENCE: 159

Gln Gln Ser Tyr Glu Glu Pro Tyr Thr
1               5

<210> SEQ ID NO 160
<211> LENGTH: 10
<212> TYPE: PRT
<213> ORGANISM: Mus musculus

<400> SEQUENCE: 160

Gly Tyr Thr Phe Thr Lys Tyr Thr Met His
1               5                   10

<210> SEQ ID NO 161
<211> LENGTH: 17
<212> TYPE: PRT
<213> ORGANISM: Mus musculus

<400> SEQUENCE: 161

Phe Ile Asn Pro Asn Ser Gly Tyr Thr Asp Tyr Asn Gln Lys Phe Lys
1               5                   10                  15
Ala

<210> SEQ ID NO 162
<211> LENGTH: 14

```
<212> TYPE: PRT
<213> ORGANISM: Mus musculus

<400> SEQUENCE: 162

Tyr Pro Ile Tyr Ser Asp Tyr Gly Pro Tyr Ala Met Asp Tyr
1               5                   10

<210> SEQ ID NO 163
<211> LENGTH: 15
<212> TYPE: PRT
<213> ORGANISM: Mus musculus

<400> SEQUENCE: 163

Arg Ala Ser Glu Ser Val Asp Ser Tyr Gly Asp Ser Phe Met His
1               5                   10                  15

<210> SEQ ID NO 164
<211> LENGTH: 7
<212> TYPE: PRT
<213> ORGANISM: Mus musculus

<400> SEQUENCE: 164

Arg Ala Ser Asn Leu Glu Ser
1               5

<210> SEQ ID NO 165
<211> LENGTH: 9
<212> TYPE: PRT
<213> ORGANISM: Mus musculus

<400> SEQUENCE: 165

Gln Gln Ser His Gly Asp Pro Tyr Thr
1               5

<210> SEQ ID NO 166
<211> LENGTH: 10
<212> TYPE: PRT
<213> ORGANISM: Mus musculus

<400> SEQUENCE: 166

Gly Tyr Thr Phe Ser Arg Tyr Thr Met His
1               5                   10

<210> SEQ ID NO 167
<211> LENGTH: 17
<212> TYPE: PRT
<213> ORGANISM: Mus musculus

<400> SEQUENCE: 167

Phe Ile Asn Pro Asn Ser Gly Tyr Thr Asp Tyr Asn Gln Lys Phe Lys
1               5                   10                  15

Asp

<210> SEQ ID NO 168
<211> LENGTH: 14
<212> TYPE: PRT
<213> ORGANISM: Mus musculus

<400> SEQUENCE: 168

His Pro Ile Tyr Ser Asp Tyr Gly Pro Tyr Ala Met Asp Tyr
1               5                   10

<210> SEQ ID NO 169
<211> LENGTH: 15
```

```
<212> TYPE: PRT
<213> ORGANISM: Mus musculus

<400> SEQUENCE: 169

Arg Ala Ser Glu Ser Val Asp Ser Tyr Gly Asn Ser Phe Met His
1               5                   10                  15

<210> SEQ ID NO 170
<211> LENGTH: 7
<212> TYPE: PRT
<213> ORGANISM: Mus musculus

<400> SEQUENCE: 170

Leu Ala Ser Asn Leu Glu Ser
1               5

<210> SEQ ID NO 171
<211> LENGTH: 9
<212> TYPE: PRT
<213> ORGANISM: Mus musculus

<400> SEQUENCE: 171

Gln Gln Asn Asn Glu Asp Pro Trp Thr
1               5

<210> SEQ ID NO 172
<211> LENGTH: 10
<212> TYPE: PRT
<213> ORGANISM: Mus musculus

<400> SEQUENCE: 172

Gly Phe Thr Phe Ser Asp Tyr Tyr Met Tyr
1               5                   10

<210> SEQ ID NO 173
<211> LENGTH: 17
<212> TYPE: PRT
<213> ORGANISM: Mus musculus

<400> SEQUENCE: 173

Thr Ile Ser Asp Gly Gly Asp Tyr Thr Tyr Tyr Pro Asp Ser Val Lys
1               5                   10                  15
Gly

<210> SEQ ID NO 174
<211> LENGTH: 10
<212> TYPE: PRT
<213> ORGANISM: Mus musculus

<400> SEQUENCE: 174

Glu Gly Asp Tyr Tyr Gly Pro Phe Ala Tyr
1               5                   10

<210> SEQ ID NO 175
<211> LENGTH: 11
<212> TYPE: PRT
<213> ORGANISM: Mus musculus

<400> SEQUENCE: 175

Lys Ala Ser Gln Asn Val Gly Thr Ala Val Ala
1               5                   10

<210> SEQ ID NO 176
<211> LENGTH: 7
```

<212> TYPE: PRT
<213> ORGANISM: Mus musculus

<400> SEQUENCE: 176

Ser Ala Ser Tyr Arg Tyr Ser
1               5

<210> SEQ ID NO 177
<211> LENGTH: 9
<212> TYPE: PRT
<213> ORGANISM: Mus musculus

<400> SEQUENCE: 177

Gln Gln Tyr Asn Ser Tyr Pro Tyr Thr
1               5

<210> SEQ ID NO 178
<211> LENGTH: 11
<212> TYPE: PRT
<213> ORGANISM: Mus musculus

<400> SEQUENCE: 178

Ser Gly Tyr Thr Phe Thr Asp Tyr Ser Ile His
1               5                   10

<210> SEQ ID NO 179
<211> LENGTH: 20
<212> TYPE: PRT
<213> ORGANISM: Mus musculus

<400> SEQUENCE: 179

Trp Ile Gly Val Ile Ser Ser Tyr Tyr Gly Asp Ala Arg His Asn Gln
1               5                   10                  15

Lys Phe Lys Gly
            20

<210> SEQ ID NO 180
<211> LENGTH: 10
<212> TYPE: PRT
<213> ORGANISM: Mus musculus

<400> SEQUENCE: 180

Asp Gly Tyr Tyr Gly Tyr Ala Met Asp Tyr
1               5                   10

<210> SEQ ID NO 181
<211> LENGTH: 16
<212> TYPE: PRT
<213> ORGANISM: Mus musculus

<400> SEQUENCE: 181

Arg Ser Thr Gln Ser Leu Val His Ser Asn Gly Asn Thr Tyr Leu His
1               5                   10                  15

<210> SEQ ID NO 182
<211> LENGTH: 14
<212> TYPE: PRT
<213> ORGANISM: Mus musculus

<400> SEQUENCE: 182

Lys Val Ser Tyr Arg Phe Ser Gly Val Pro Asp Arg Phe Ser
1               5                   10

<210> SEQ ID NO 183

```
<211> LENGTH: 10
<212> TYPE: PRT
<213> ORGANISM: Mus musculus

<400> SEQUENCE: 183

Ser Gln Ser Thr His Val Pro Phe Thr Phe
1               5                   10

<210> SEQ ID NO 184
<211> LENGTH: 10
<212> TYPE: PRT
<213> ORGANISM: Mus musculus

<400> SEQUENCE: 184

Ser Gly Tyr Thr Phe Thr Asp Tyr Asn Met
1               5                   10

<210> SEQ ID NO 185
<211> LENGTH: 20
<212> TYPE: PRT
<213> ORGANISM: Mus musculus

<400> SEQUENCE: 185

Trp Ile Gly Asp Ile Asn Pro Asn Val Gly Asp Thr Ile Tyr Asn Gln
1               5                   10                  15

Lys Phe Lys Gly
            20

<210> SEQ ID NO 186
<211> LENGTH: 10
<212> TYPE: PRT
<213> ORGANISM: Mus musculus

<400> SEQUENCE: 186

Ser Asp Asp Asn Tyr Ser Trp Phe Thr Tyr
1               5                   10

<210> SEQ ID NO 187
<211> LENGTH: 11
<212> TYPE: PRT
<213> ORGANISM: Mus musculus

<400> SEQUENCE: 187

Lys Ala Ser Gln Ser Val Ser Asn Asp Val Ala
1               5                   10

<210> SEQ ID NO 188
<211> LENGTH: 7
<212> TYPE: PRT
<213> ORGANISM: Mus musculus

<400> SEQUENCE: 188

Tyr Ala Ser Asn His Tyr Thr
1               5

<210> SEQ ID NO 189
<211> LENGTH: 10
<212> TYPE: PRT
<213> ORGANISM: Mus musculus

<400> SEQUENCE: 189

Gln Gln Asp Ser Ser Ser Pro Leu Thr Phe
1               5                   10
```

```
<210> SEQ ID NO 190
<211> LENGTH: 10
<212> TYPE: PRT
<213> ORGANISM: Mus musculus

<400> SEQUENCE: 190

Ser Gly Tyr Thr Phe Thr Asp Tyr Asn Met
1               5                   10

<210> SEQ ID NO 191
<211> LENGTH: 20
<212> TYPE: PRT
<213> ORGANISM: Mus musculus

<400> SEQUENCE: 191

Trp Ile Gly Asp Ile Asn Pro Asn Asn Gly Asp Thr Ile Tyr Asn Gln
1               5                   10                  15

Asn Phe Lys Asp
            20

<210> SEQ ID NO 192
<211> LENGTH: 10
<212> TYPE: PRT
<213> ORGANISM: Mus musculus

<400> SEQUENCE: 192

Ser Asp Asp Asp Tyr Ser Trp Phe Ala His
1               5                   10

<210> SEQ ID NO 193
<211> LENGTH: 11
<212> TYPE: PRT
<213> ORGANISM: Mus musculus

<400> SEQUENCE: 193

Lys Ala Ser Gln Ser Val Ser Asn Asp Val Ala
1               5                   10

<210> SEQ ID NO 194
<211> LENGTH: 7
<212> TYPE: PRT
<213> ORGANISM: Mus musculus

<400> SEQUENCE: 194

Tyr Ala Ser Asn Arg Tyr Thr
1               5

<210> SEQ ID NO 195
<211> LENGTH: 10
<212> TYPE: PRT
<213> ORGANISM: Mus musculus

<400> SEQUENCE: 195

Gln Gln Asp Ser Ser Ser Pro Leu Thr Phe
1               5                   10
```

US 9,428,575 B2

ANTI-GRANULYSIN ANTIBODIES AND METHODS OF USE THEREOF

FIELD OF THE INVENTION

This invention relates to anti-granulysin antibodies, particularly uses of such antibodies.

BACKGROUND OF THE INVENTION

Mammalian immune system plays a key role in controlling microbial infection in vivo. T cells play important roles in such immune responses. One class of T cells, the cytolytic T cells (CTL), function by lysing foreign and virally infected cells. The primary mechanism of CTL-mediated cytolysis involves directional release of cytoplasmic granule contents, by which CTL and NK cells initiate the lysis of the target cells.

The contents of the cytoplasmic granules include: a pore-forming protein (perforin), a family of serine proteases (granzymes), and a late T cell activation marker, granulysin. Granulysin is cytolytic against microbes and tumors. When attached to infected body cells, granulysis can create holes in the target cell membranes, leading to destruction of the cells. In addition, granulysin can induce apoptosis in the target cells and also has antimicrobial action. (Janeway, Charles (2005). *Immunobiology: the immune system in health and disease* (6th ed.). New York: Garland Science).

Human granulysin is expressed as proteins of two sizes (9 kDa and 15 kDa) derived from three unique transcripts. (see FIG. 1). Granulysin is saposin-like lipid binding protein. The crystal structure (Anderson et al. (2003) J Mol. Biol. 325 (2):355-65) reveals a five-helix bundle with positive charges distributing in a ring around the molecule and one face without net positive charges (FIG. 2). In addition, granulysin is stabilized by two highly conserved intra-molecule disulfide bonds.

While immune responses are important in the defense against infections, unwanted immune responses may lead to disorders. Examples of disorders associated with unwanted immune responses include adverse drug reactions (ADRs), graft-versus-host diseases (GVHD), inflammatory diseases, autoimmune diseases, transplant rejection, allergic diseases, and T cell-derived cancers.

U.S. Pat. No. 7,718,378, issued to Chen et al., disclosed that granulysin is involved in the pathology of diseases associated with unwanted immunological responses or cytotoxic T cell mediated-disorders, such as SJS (Steven-Johnson syndrome), TEN (toxic epidermal necrolysis), and GVHD.

The pathogenesis of SJS/TEN is not fully understood. However, adverse drug reaction is a major cause of these conditions. In 2007, FDA issued an alert asking doctors to screen patients for human leukocyte antigen (HLA) allele, HLA-B*1502, before carbamazepine therapy because dangerous or even fatal skin reactions (SJS and TEN) can result from carbamazepine therapy with these patients. The manifestations of these serious life-threatening adverse drug reactions are believed to be immune-mediated since rechallenging with the same drug typically shortens the incubation period and results in more severe manifestations (Roujeau et al., Toxicology, 2005 Apr. 15; 209(2):123-9).

In addition, clinical, histopathological, immunocytological, and functional findings in SJS/TEN support the concept that SJS/TEN is a specific drug sensitivity reaction initiated by cytotoxic lymphocytes. Prior in vitro studies suggest that the drug presentation is MHC class I restricted, there is a clonal expansion of CD8+ CTLs, and these cells induce effector cytotoxic responses. The MHC-restricted presentation of a drug or its metabolites for T-cell activation is further supported by the recent findings of strong genetic association between HLA-B alleles and reaction to specific drugs. (Chung et al. Nature, 2004 Apr. 1; 428(6982):486.).

Cytotoxic T-cells are observed to infiltrate the skin lesions of SJS/TEN patients (Nassif et al., Allergy Clin. Immunol. 2004 November; 114(5): 1209-15). The T lymphocytes in the blister fluid and epidermis show a predominance of CD8+ phenotype (Nassif et al., J. Invest. Dermatol. 2002 April; 118(4):728-33). These observations point to a cutaneous recruitment of antigen-primed and cytotoxic T cells in the pathogenesis of SJS/TEN.

Granulysin was found to be a key molecule responsible for the unique clinical manifestation of SJS/TEN. Blister fluids from skin lesions of SJS/TEN patients exhibited cytolytic activity against B-cells and keratinocytes and contain granulysin as the most predominant cytotoxic protein. Furthermore, injection of granulysin into epidermis of mice induced massive skin cell death, mimicking the human pathology of SJS/TEN. Thus, granulysin is a key molecule responsible for the disseminated keratinocyte apoptosis and underlies the missing link of the pathogenic mechanism of SJS/TEN.

FIG. 3 shows a schematic illustrating a possible mechanism for the involvement of granulysin in adverse drug reactions (e.g., carbamazepine adverse reaction). According to this proposed mechanism, binding of the drug molecule (antigen) to MHC I on an antigen presenting cell (e.g., keratinocyte) leads to activation of CD8+ cytotoxic T cells. The drug-MHC I interaction is most significant when the allele is HLA-B*1502 and the drug is carbamazepine. Activation of the T cells leads to the production of granulysin, among other substances. Granulysin then triggers the apoptosis (and cytolysis) of keratinocyte.

In acute GVHD, granulysin was markedly increased in serum, and the levels of granulysin in serum correlated with the severity of GVHD. In addition, it was shown that allospecific T cells released granulysin in an allo-specific manner in vitro, and the granulysin release was correlated with allo-specific cytotoxic activity. These results indicate that granulysin plays an important role in GVHD. (Nagasawa et al. 2006, Am. J. Hematol. 81(5):340-8).

The above observations suggest that granulysin plays an important role in these unwanted immune response disorders. Therefore, granulysin is a useful target for diagnosis and therapy of such unwanted immune response disorders.

SUMMARY OF THE INVENTION

Embodiments of the invention relate to antibodies that are capable of neutralizing the cytotoxicity and antimicrobial activity of granulysin. The antibodies may be polyclonal or monoclonal antibodies.

In one aspect, the invention relates to anti-granulysin antibodies capable of neutralizing an activity of granulysin. An antibody of the invention is capable of binding to an epitope region on granulysin spanning R64 to R113 (SEQ ID NO:81).

In accordance with any embodiment of the invention above, the antibody may comprise a sequence selected from the sequences of SEQ ID NO:82 to SEQ ID NO:195, or from the sequences of SEQ ID NO:39 to SEQ ID NO:76.

In accordance with some embodiments of the invention, the antibody may comprise the sequences of SEQ ID NO:82 through SEQ ID NO:87, or SEQ ID NO:88 through SEQ ID NO:93 or SEQ ID NO:94 through SEQ ID NO:99, or SEQ ID NO:100 through SEQ ID NO:105, or SEQ ID NO:106 through SEQ ID NO:111, or SEQ ID NO:112 through SEQ ID NO:117, or SEQ ID NO:118 through SEQ ID NO:123 or SEQ ID NO:124 through SEQ ID NO:129, or SEQ ID NO:130 through SEQ ID NO:135, or SEQ ID NO:136 through SEQ ID NO:141, or SEQ ID NO:142 through SEQ ID NO:147, or SEQ ID NO:148 through SEQ ID NO:153 or SEQ ID NO:154 through SEQ ID NO:159, or SEQ ID NO:160 through SEQ ID NO:165, or SEQ ID NO:166 through SEQ ID NO:171, or SEQ ID NO:172 through SEQ ID NO:177, or SEQ ID NO:178 through SEQ ID NO:183 or SEQ ID NO:184 through SEQ ID NO:189, or SEQ ID NO:190 through SEQ ID NO:195.

In accordance with some embodiments of the invention, the antibody may comprise the sequences of: SEQ ID NO:39 and SEQ ID NO:40, or SEQ ID NO:41 and SEQ ID NO:42 or SEQ ID NO:43 and SEQ ID NO:44, or SEQ ID NO:45 and SEQ ID NO:46, or SEQ ID NO:47 and SEQ ID NO:48, or SEQ ID NO:49 and SEQ ID NO:50, or SEQ ID NO:51 and SEQ ID NO:52 or SEQ ID NO:53 and SEQ ID NO:54, or SEQ ID NO:55 and SEQ ID NO:56, or SEQ ID NO:57 and SEQ ID NO:58, or SEQ ID NO:59 and SEQ ID NO:60, or SEQ ID NO:61 and SEQ ID NO:62 or SEQ ID NO:63 and SEQ ID NO:64, or SEQ ID NO:65 and SEQ ID NO:66, or SEQ ID NO:67 and SEQ ID NO:68, or SEQ ID NO:69 and SEQ ID NO:70, or SEQ ID NO:11 and SEQ ID NO:72 or SEQ ID NO:73 and SEQ ID NO:74, or SEQ ID NO:75 and SEQ ID NO:76.

An antibody set forth above in accordance with one embodiment of the invention may be a monoclonal antibody. In accordance with any embodiment of the invention, the antibody may be a humanized antibody or a human antibody. In accordance with embodiments of the invention, an antibody can prevent the cytotoxicity of granulysin.

In another aspect, the invention relates to methods for treating an unwanted immune response disease by administering to a subject in need thereof any anti-granulysin antibody set forth above. In accordance with any of the above embodiment, the unwanted immune response disorder is SJS, TEN, or GVHD.

Other aspects and advantages of the invention will be apparent from the following description and the appended claims.

BRIEF DESCRIPTION OF THE DRAWINGS

FIG. 7 shows CDR sequences of various anti-granulysin antibodies.

FIG. 15 shows a schematic diagram of granulysin action, illustrating the involvement of the arginine positive charges in the interactions with negative charged phospholipid layers.

FIG. 16 shows of a three-dimensional structure of granulysin, illustrating the charged residues on one face.

FIG. 18 shows results from the analysis of bindings of various anti-granulysin antibodies to granulysin mutants, illustrating their ability to reverse granulysin's antimicrobial activities and the CDR sequences.

FIG. 19 shows a flowchart outlining a procedure for assessing binding of antibodies to denatured granulysin in accordance with one embodiment of the invention.

DEFINITIONS

Figure 1:
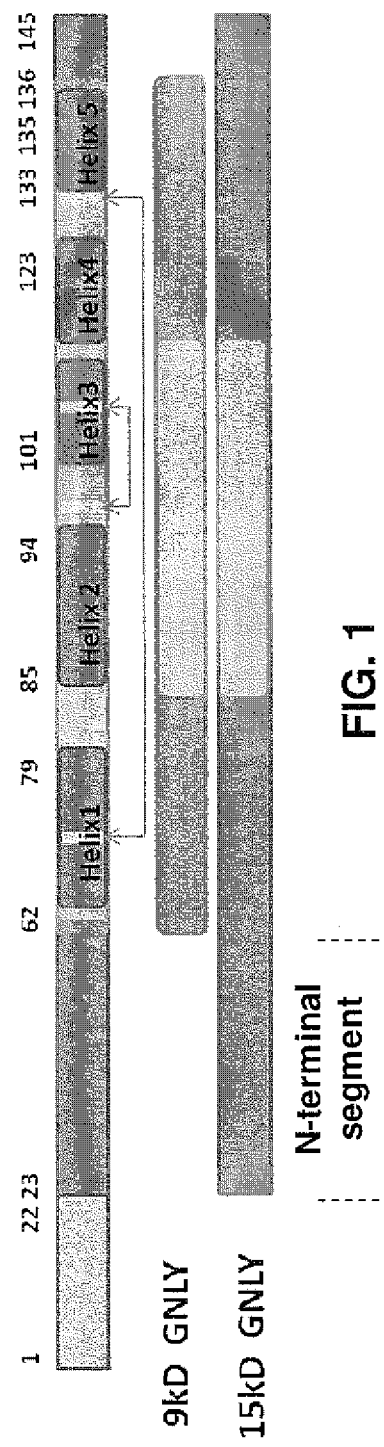
FIG. 1 shows schematics of granulysin structures including 9 kDa granulysin and 15 kDa granulysin.

As used herein, the term "antibody" refers to an immunoglobulin molecule or immunologically active portion thereof, i.e., an antigen-binding portion or a fragment thereof. Thus, an antibody comprises at least one (preferably two) heavy (H) chain variable regions ($V_H$), and at least one (preferably two) light (L) chain variable regions ($V_L$). The $V_H$ and $V_L$ regions can be further subdivided into regions of hypervariability, i.e., the "complementarity determining regions" ("CDR"), interspersed with regions that are more conserved, i.e., "framework regions" ("FR"). Each $V_H$ and $V_L$ is composed of three CDR's and four FR's, arranged from amino-terminus to carboxy-terminus in the following order: FR1, CDR1, FR2, CDR2, FR3, CDR3, FR4. (see, Kabat et al. (1991) Sequences of Proteins of Immunological Interest, Fifth Edition, U.S. Department of Health and Human Services, NIH Publication No. 91-3242; and Chothia et al. (1987) J. Mol. Biol. 196:901-917, which are incorporated herein by reference).

An antibody may include one or more constant regions from a heavy or light chain constant region. The heavy chain constant regions comprise three domains, $C_{H1}$, $C_{H2}$ and $C_{H3}$, and the light chain constant region comprises one domain, $C_L$. The variable region of the heavy and/or light chains contains a binding domain that interacts with an antigen, while the constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. Human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH-terminus. Full-length immunoglobulin "heavy chains" (about 50 KDa or 446 amino acids), are similarly encoded by a variable region gene (about 116 amino acids) and one of the aforementioned constant region genes, e.g., gamma (encoding about 330 amino acids).

The term "antigen-binding fragment" of an antibody (or "antibody portion," or "fragment") refers to one or more fragments of a full-length antibody that retains the ability to specifically bind to an antigen. Examples of antigen-binding fragments of an antibody include, but are not limited to: (i) an Fab fragment, which is a monovalent fragment consisting of the $V_L$, $V_H$, $C_L$ and $C_{H1}$ domains; (ii) an F(ab')$_2$ fragment, which is a bivalent fragment comprising two Fab fragments linked by a disulfide bridge at the hinge region; (iii) an Fd fragment consisting of the $V_H$ and $C_{H1}$ domains; (iv) an Fv fragment consisting of the $V_L$ and $V_H$ domains of a single arm of an antibody, (v) a dAb fragment (Ward et al., (1989) Nature 341:544-546), which consists of $V_H$ domain; and (vi) an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain, in which the $V_L$ and $V_H$ regions pair to form a monovalent molecule (known as single chain Fv (scFv); see e.g., Bird et al. (1988) Science 242:423-426; and Huston et al. (1988) Proc. Natl. Acad. Sci. USA 85:5879-5883). Such single chain antibodies are also encompassed within the term "antigen-binding fragment" of an antibody. These antibody fragments can be obtained using conventional techniques known to those skilled in the art, and the fragments are screened for utility in the same manner as for intact antibodies.

DETAILED DESCRIPTION

Embodiments of the present invention relate to anti-granulysin antibodies and methods of using these antibodies. The uses may include treatments, prevention, or diagnosis of diseases associated with granulysin, such as STS/TEN. Antibodies of the invention may include any suitable antibodies, such as polyclonal antibodies or monoclonal antibodies of all classes, human antibodies, and humanized antibodies made by genetic engineering.

In accordance with embodiments of the invention, anti-granulysin antibodies may be produced using hybridoma or phage display techniques. Monoclonal antibody production using hybridoma is well known in the art. (see, Schwaber, J.; Cohen, E. P. (1973). "Human×mouse somatic cell hybrid clone secreting immunoglobulins of both parental types," Nature 244 (5416): 444-447). Similarly, phage display and combinatorial methods for generating antibodies are known in the art (see e.g., Ladner et al. U.S. Pat. No. 5,223,409; Fuchs et al. (1991) Bio/Technology 9:1370-1372; Hay et al. (1992), Hum. Antibody Hybridomas 3:81-85; Huse et al. (1989), Science 246:1275-1281,).

Figure 4:
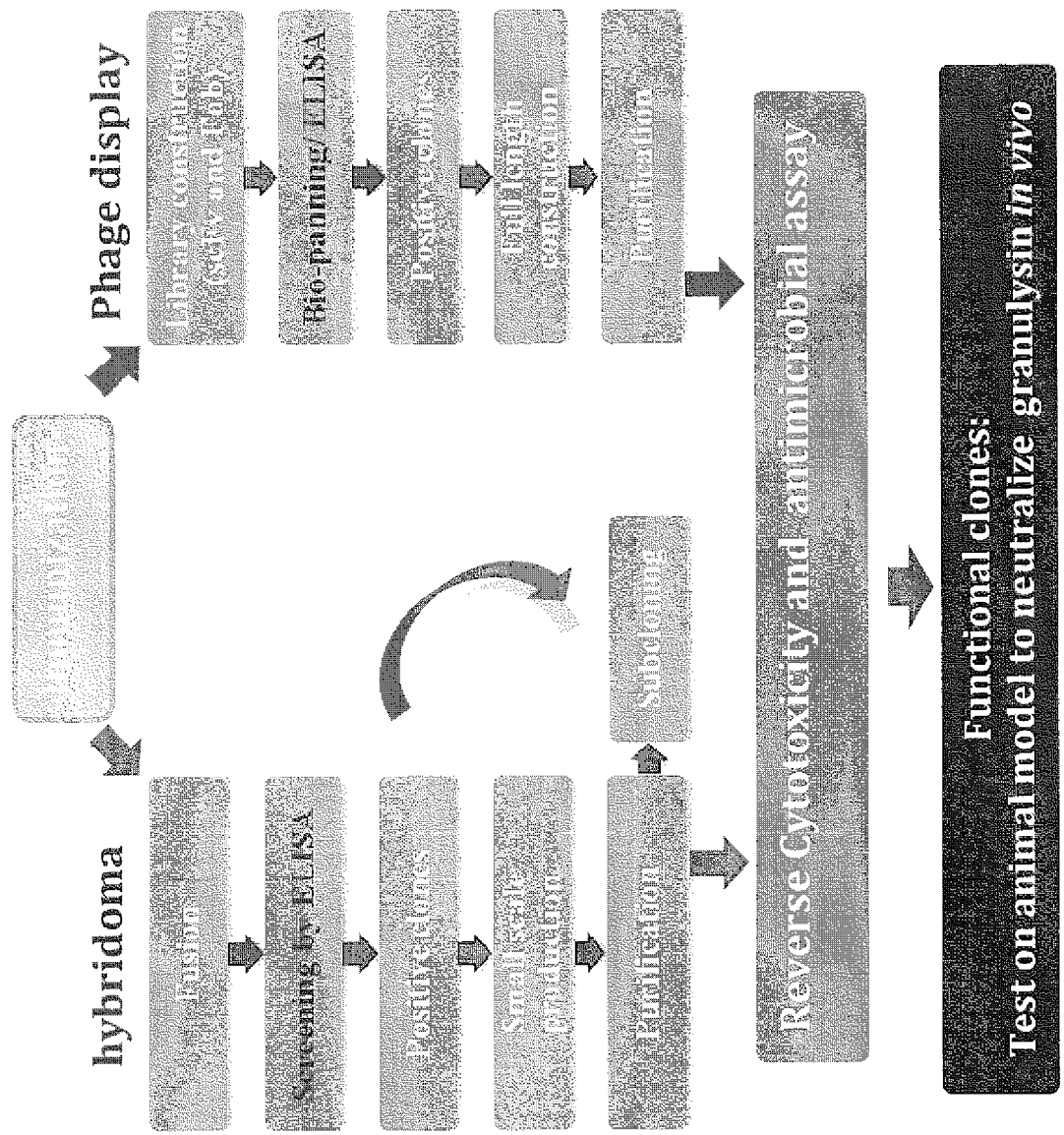
FIG. 4 shows schematics illustrating the approaches for generating anti-granulysin antibodies in accordance with embodiments of the invention.

FIG. 4 outlines general strategies (hybridoma and phage display) for the production of anti-granulysin antibodies. With the hybridoma approach, a mouse is immunized with an antigen (e.g., granulysin or a fragment or derivative thereof). Then, the spleen cells from the immunized animal are fused with myeloma cells. Polyethylene glycol may be used to fuse adjacent plasma membranes of the cells. The fusion efficiency is low, and a selective medium in which only fused cells can grow is used to select the hybridoma cells. The hybridoma cells are then screened for the production of the desired antibodies, and positive clones are isolated. The positive clones may be used for small scale productions and for further purification and subcloning. monoclones producing useful antibodies are isolated.

With the phase display approach, typically Fab or scFv are produced instead of a whole antibody. First, a library may be constructed with DNA fragments from the CDR from an immunized mouse (by RT-PCR and PCR) fused to a coat protein of the phage. The phages having the desired CDR sequences will bind to the target antigen and can be enriched by bio-panning or ELISA, in which the target antigen (e.g., granulysin) is coated on a plate and the phages are allowed to bind to the antigen. Then, the non-binders are washed away. The bound, positive clones are collected and expanded. The panning/enrichment process may be repeated several times to purify the positive clones. The sequences from these positive clones (i.e., the CDR sequences) can then be constructed into an antibody framework to produce a full-length construct. The antibodies may be produced from these full-length constructs and purified for assays.

Both the hybridoma approach and the phage display approach will be described in details using working examples.

EXAMPLE 1

Immunization Procedure

Recombinant human granulysin (15 kDa, expressed in E. coli) was used as an antigen. This antigen was used with Freund's complete adjuvant (FCA) or Freund's incomplete adjuvant (FIA) to immunize mice according a suitable schedule. For example, Table 1 illustrates one exemplary immunization schedule:

TABLE 1

| Immunization Scheme | | | | |
| --- | --- | --- | --- | --- |
| Schedule | Date | Dose | Adjuvant | Administration |
| Immunized | Week 0 | 50 μg | FCA | s.c. |
| Boost 1st | Week 2 | 25 μg | FIA | s.c. |
| Boost 2nd | Week 4 | 25 μg | FIA | s.c. |
| Boost 3rd | Week 6 | 25 μg | FIA | s.c. |
| Bleed | Week 8 | | | Test serum titer |

EXAMPLE 2

Testing Serum Titer by ELISA

ELISA plates (e.g., 96-well plates) were coated with a recombinant human granulysin (15 kDa, E. coli expressed). Test samples were added to the plate and allowed to bind with the coated proteins. After washing to remove unbound antibodies, the bound antibodies were assessed with a second antibody (e.g., goat anti-mouse IgG coupled with horse raddish peroxidase (HRP)). The amounts of bound secondary antibodies can be estimated using a proper substrate for HRP. For example, 3,3',5,5'-Tetramethylbenzidine (TMB), 3,3'-Diaminobenzidine (DAB), or 2,2'-azino-bis(3-ethylbenzothiazoline-6-sulphonic acid) (ABTS) may be used as a calorimetric substrate of HRP. Table 2 shows results of one example.

TABLE 2

Serum Titers by ELISA (HRP reaction, OD readings)

| Dilution | No. 1 | No. 2 | No. 3 | No. 4 | No. 5 | No. 6 | Normal Sera |
|---|---|---|---|---|---|---|---|
| $10^3\times$ | 2.128 | 2.165 | 2.083 | 2.165 | 2.087 | 2.173 | 0.055 |
| $10^4\times$ | 2.158 | 2.084 | 2.082 | 2.080 | 2.131 | 2.116 | 0.044 |
| $10^5\times$ | 1.922 | 1.850 | 1.443 | 1.957 | 1.790 | 2.121 | 0.052 |
| $10^6\times$ | 0.421 | 0.521 | 0.268 | 0.548 | 0.519 | 1.303 | 0.039 |

Blank: 0.042

EXAMPLE 3

Hybridoma Generation

After immunization of the mouse and confirmation of the production of antibodies with the ELISA assays, the mouse was sacrificed. The splenocytes from the mouse were fused with NS-1 myeloma cells with the aid of PEG 1500.

The hybridoma cells were then screened for the production of anti-granulysin antibodies using ELISA assays in a manner similar to that described above. That is, the screening was performed using recombinant human granulysin (15 kDa) expressed from *E. coli* or NS0 cells, and the positive clones were identified using a secondary antibody-HRP conjugate (goat anti-mouse IgG-HRP). The NS0 cells are clonal derivatives of the parent NS1 cell line and are capable of growth in suspension culture.

In this example, using the *E. coli* expressed recombinant human granulysin (15 kDa), 112 clones were found to have OD>1.8 and 22 clones were found to have OD>1.5. Similarly, using NS0 expressed recombinant human granulysin (15 kDa), 111 clones were found to have an OD>1.8, 1 clone had an OD=1.648, and 22 clones had OD>0.4. The OD for the blank was 0.097.

EXAMPLE 4

Cytotoxicity Assay

The positive clones from the above example were isolated to produce anti-granulysin antibodies for cytotoxicity assays. The anti-granulysin antibodies from polyclone hybridoma culture supernatants were purified using protein G beads. These antibodies were assessed for their abilities to reduce or prevent granulysin-induced cytotoxicity.

The granulysin-induced cytotoxicity was assayed using WST-1 as follows:

Day 0: Suitable cells (e.g., keratinocytes) were cultured and trypsinized with 1/10 volume of 0.05% trypsin in EDTA for 5 minutes. The removed cells were counted to determine the cell number. Then, it was centrifuged at 600 rpm for 5 minutes to collect the cells. The cell concentration was then adjusted to $1\times10^5$ cells/ml and seeded in wells of a 96-well plate (200 µl/well; $2\times10^4$ cells/well). The cells were cultured for 24 hours.

Day 1: granulysin and anti-granulysin antibodies were added to the wells. For example, to each well was added 20 µl antibody (1:10 and 1:1 molar ratio), and granulysin 20 µl (from 4 µg/ml to 62.5 µg/ml). After 4 hours, cell death was assessed in the following procedure.

Day 2: add 20 µl WST-1 solution to each well and incubate at 37° C. for 24 hours. WST-1 cell proliferation assay kits are available from many commercial sources (e.g., G-Biosciences, St. Louis, Mo.; Cayman Chemical Co., Ann Arbor, Mich.). The assay is based on the enzymatic cleavage of the tetrazolium salt WST-1 to formazan by cellular mitochondrial dehydrogenases present in viable cells. The products, formazan, can be quantitated by OD 450-655 nm to infer the viable cell numbers.

As noted above, granulysin can cause cytolysis and apoptosis of the target cells. If any neutralizing antibodies are present, the cytolysis activity of granulysin would be reduced or prevented. Therefore, the viable cell numbers will increase.

Figure 5:
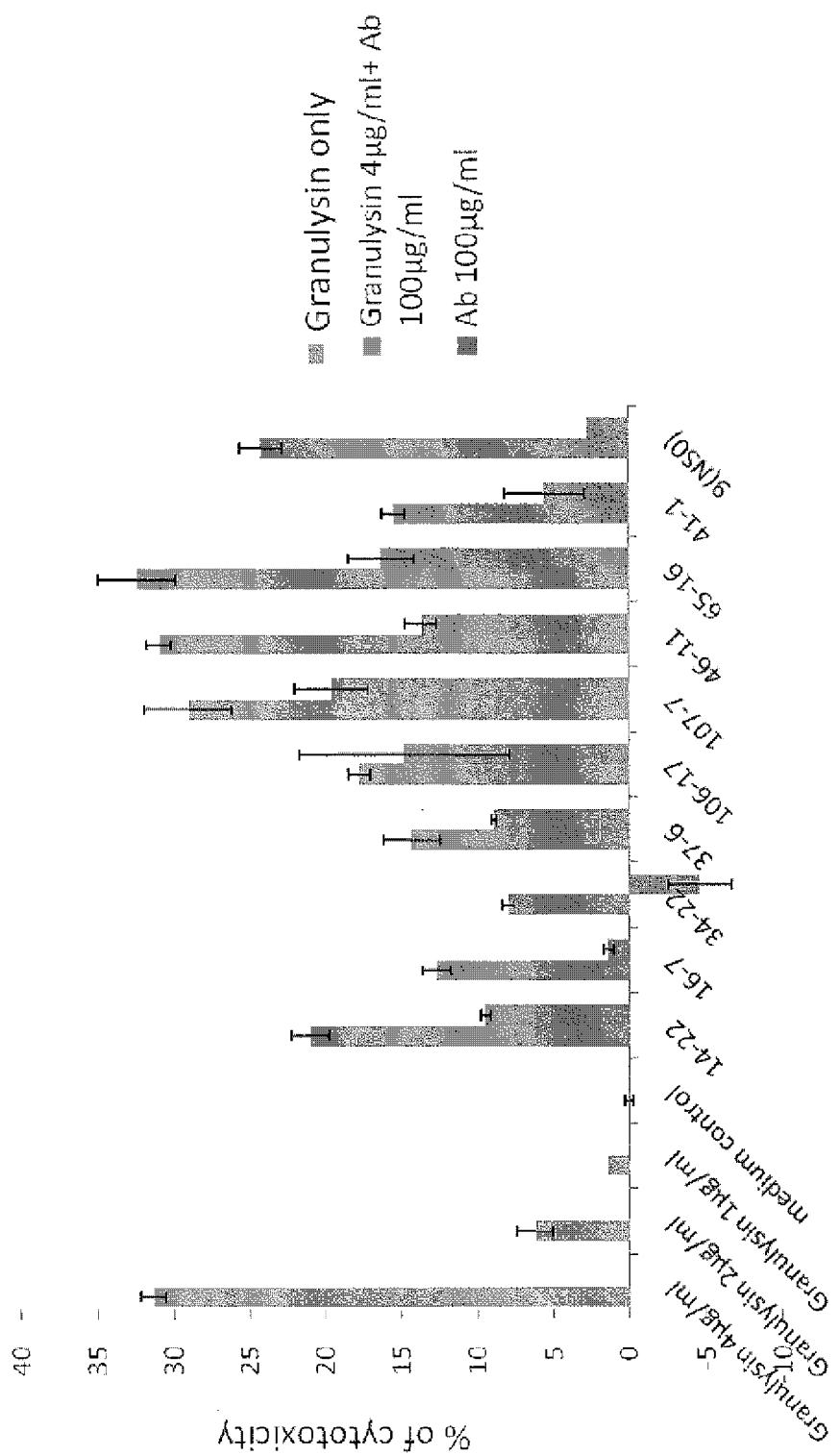
FIG. 5 shows the abilities of various anti-granulysin antibodies to reduce the cytotoxicity of granulysin.

Results from these assays using keratinocytes are shown in FIG. 5. From these assay results, it was found that clones such as 14-22, 16-7, 34-22, 37-6, 106-17, and 41-1 were effective in reducing the cytotoxicity of granulysin. Such clones may be further characterized for potential uses. For example, the following table shows the sequence analysis of the CDR domains of three representative clones.

| Analyte Antibodies | Keratinocyte Cytotoxicity | CDRH1 | CDRH2 | CDRH3 |
|---|---|---|---|---|
| M34.22 | ++ | SGYTFTDYSIH | WIGVISSYYGDARHNQKFKG | DGYYGYAMDY |
| M16.7 | ++ | SGYTFTDYNM | WIGDINPNVGDTIYNQKFKG | DDYSWFAHWG |
| M106.17 | ++(*) | SGYTFTDYNM | WIGDINPNNGDTIYNQNFKD | DNYSWFTYWG |

* M106.17 showed some cytotoxicity.

These neutralizing anti-granulysin antibodies would be useful as therapeutic agents for the treatment and prevention of disorders that are mediated by granulysin, such as SJS, TEN and GVHD.

The positive clones producing neutralizing antibodies can be further purified by subcloning. Subcloning can be performed, for example, by seeding 1 cell/well in 20% FBS-5% Briclone-DMEM. Finally, the positive hybridoma clones may be characterized, for example, using mouse isotyping ELISA kits (e.g., SBA Clonotyping™ System from Southern Biotech, Birmingham, Ala.).

Phage Display Approach

EXAMPLE 5

Construction of Phage Library

Figure 6:
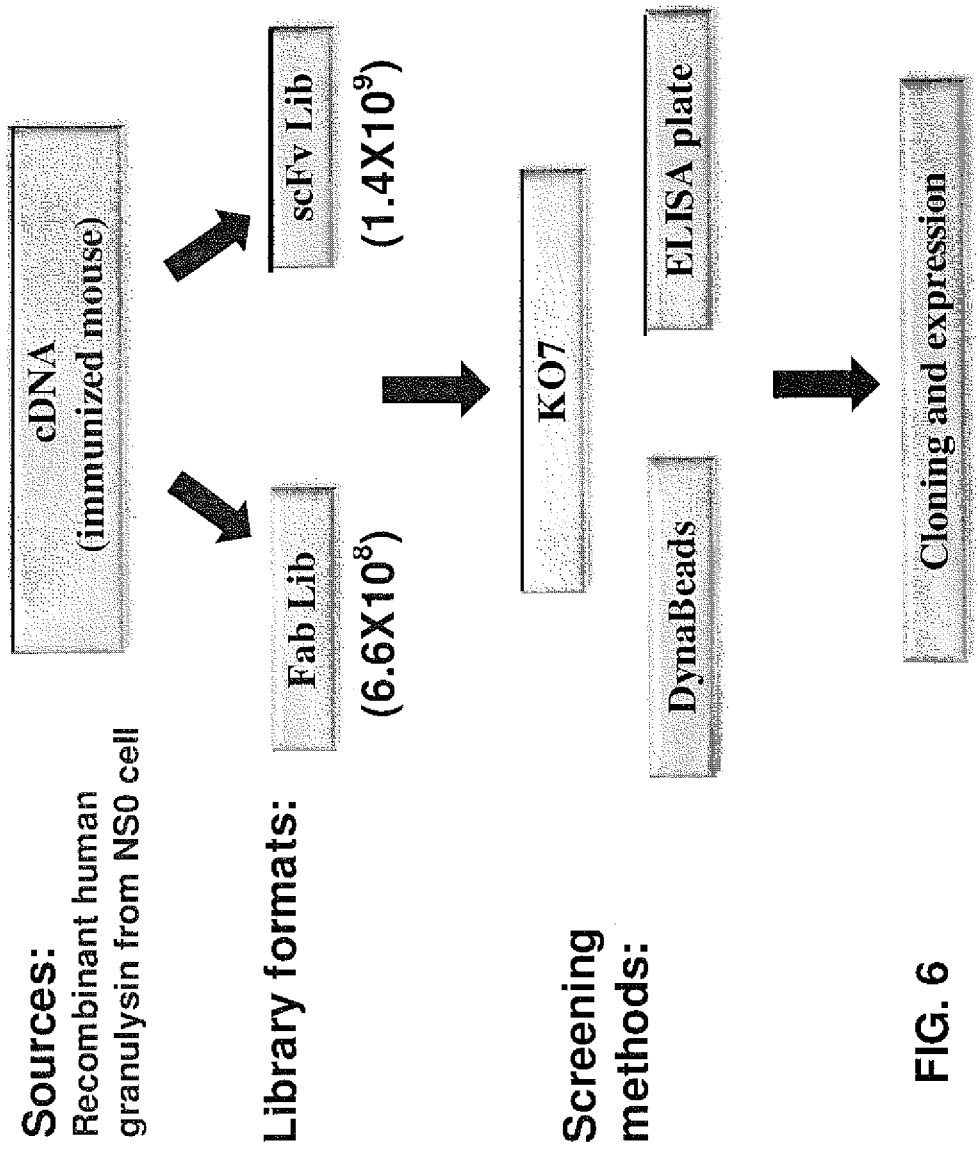
FIG. 6 shows a schematic illustrating a method of using phase display to identify anti-granulysin antibodies.

In accordance with embodiments of the invention, antibodies can also be generated using phage panning. As shown in FIG. 6, a cDNA library may be constructed from an immunized mouse. The mouse may be immunized, for example, with a recombinant human granulysin expressed in NS0 cells. The mouse was sacrificed and the spleen was removed to extract the total RNA. RT-PCR was then used to obtain antibody fragments (e.g., $V_H$, $V_L$, heavy chain ($F_d$) or light chain). These fragments may be used to construct the Fab library. In addition, these fragments were assembled using PCR to generate antibody fragments for scFv, which were then used to construct the scFv library. In one example, the Fab library has 6.6×10$^8$ diversities and the scFv library has 1.4×10$^9$ diversities.

EXAMPLE 6

Preparation of Phages for Screening

The above (scFv or Fab) library stocks each were inoculated into 2×YT medium containing 100 µg/ml ampicillin and 2% glucose (2YTAG) and grown with shaking at 37° C. until the OD (600 nm) reached 0.5. This culture was then infected with M13KO7 helper phage by adding the helper phage in a ratio of 1:20. The resultant culture was incubated in a 37° C. water bath without shaking for 30 minutes.

Then, the infected cells were collected by spinning at 4000 rpm for 15 minutes.

The cells were resuspended gently in 2×YT containing 100 µg/ml ampicillin and 25 µg/ml kanamycin (2YTAK) and incubated with shaking at 30° C. overnight.

The overnight culture was spun at 10,000 rpm for 20 min to collect the cells. PEG/NaCl (20% PEG 8000, 2.5M NaCl; 1/5 volume) was added to the supernatant. The solution was mixed and left for 1 hour or more at 4° C. It was then spun at 10,000 rpm for 20 min. The supernatant was then aspirated off.

The pellet was resuspended in 40 ml sterile water and the spun at 12,000 rpm for 10 min to remove most of the remaining bacterial debris. A 1/5 volume PEG/NaCl was added to the supernatant again. It was mixed well and left for 1 hr or more at 4° C.

It was again spun at 10,000 rpm for 20 min and the supernatant was aspirated off. The pellet was then resuspended in PBS and spun at 12,000 rpm for 10 min to remove most of the remaining bacterial debris.

The above described is one example for the preparation of phages. This example is for illustration only and not intended to limit the scope of protection. One skilled in the art would appreciate that various modifications and variations are possible.

EXAMPLE 7

Selection Using ELISA Plates

ELISA plate (Nuns) was coated with 1 µg/100 µl antigen (e.g., recombinant human granulysin) per well. The antigen coating was performed overnight at 4° C. in PBS, pH 7.4. Then, the well were rinsed 3 times with PBS and blocked with 300 µl PBS-5% skim milk (MPBS) per well for 1.5 hours at 37° C. This was followed by rinsing with PBS 3 times.

Then, 100 µl of 10$^{11}$ to 10$^{12}$ phages in 5% MPBS or 5% MPBS was add, followed by addition of 1-7 10×His tag. The solution was incubated for 90 min at 37° C., and the test solution was discarded and washed 3 times with BS-0.05% Tween20 (PBST).

To each well was added 100 ul PBS. It was incubated for 60 min at 37° C. and washed 3 times with PBST, 1 time with PBS. The excess PBS was shaken out from the plate, and the phages were eluted by adding 100 µl 100 mM triethylamine (TEA) with rotation continuously at 37° C. for 30 min. Tris buffer (50 µl, 1M, pH 7.4) was added to the eluted 100 µl phage, for quick neutralization.

Take 10 ml of an exponentially growing culture of TG1 and add 150 µl of the eluted phage. Also add 100 µl of the TG1 culture to the immunoplate. Incubate both cultures for 30 min at 37° C. without shaking to allow for infection. Pool the 10 ml and 100 µl of the infected TG1 bacteria and spin at 4000 rpm for 15 min. Re-suspend the pelleted bacteria in 2×TY and plate on a large 2YTAG plate. The bacteria were allowed to grow at 30° C. overnight.

EXAMPLE 8

Selection Using Dynabeads®

Dynabeads® were pre-washed with 1 ml PBS three times and resuspended in 2% MPBS. Phage (0.3 ml) was mixed with 0.5 ml 2% PBSM, 1-7-10×His-tag, and the above washed Dynabeads®. The resultant suspension was pre-incubated on a rotator for 30 min.

Remove the Dynabeads® and add granulysin. The resultant mixture was mixed on a rotator for 90 min. Dynabeads® were pre-washed with 1 ml PBS three times and resuspended in 2% PBSM. This was then incubated on a rotator for 90 min.

The phage-granulysin mix was added to the equilibrated Dynabeads® on a rotator for another 30 min. The Dynabeads® were then washed with 1 ml 0.05% PBST, 0.2% PBSM, and PBS. The bound phages were then eluted with 1 ml 100 mM TEA. During the incubation, tubes were prepared with 0.5 ml 1M Tris, pH 7.4 to get ready for the addition of the eluted phages for quick neutralization.

Take 6 ml of an exponentially growing culture of TG1 and add the TEA eluted phage. Also add 4 ml of the TG1 culture to the beads. Incubate both cultures for 30 min at 37° C. (water bath) without shaking.

Pool the infected TG1 bacterial and spin at 4000 rpm for 15 min. Resuspend the pelleted bacterial in 1 ml of 2×YT and plate on a large 2TYAG plate. Grow the bacteria at 30° C. overnight.

EXAMPLE 9

Preparation of Next Round Phage

Add 5-6 ml of 2×YT, 15% glycerol to the bacterial plate that had been grown overnight as described above and loosen the colonies with a glass spreader. Add 50-100 µl of the scraped bacteria to 100 ml of 2×YTAG. Grow the bacteria with shaking at 37° C. until the OD at 600 nm is 0.5. Infect 10 ml of this culture with M13KO7 helper phage by adding helper phage in the ratio of 1:20. Incubate the infected culture without shaking in a 37° C. water bath for 30 min.

Spin the infected cells at 4000 rpm for 15 min to collect he bacteria. Resuspend the pellet gently in 50 ml of 2×YTAK and incubate the culture with shaking at 30° C. overnight.

Take 40 ml of the overnight culture and spin at 10,000 rpm for 20 min to collect the supernatant. Add 1/5 volume (8 ml) PEG/NaCl to the supernatant. Mix well and leave it for 1 hr or more at 4° C. Spin at 10,000 rpm for 20 min and then aspirate off the supernatant. Resuspend the pellet in 2 ml PBS and spin at 12000 rpm for 10 min to remove most of the remaining bacterial debris.

EXAMPLE 10

Screening of Positive Phage by ELISA

Inoculate individual colonies from the plate into 200 µl 2×YTAG 96-well plates and grow with shaking overnight at 37° C. Use a 96-well transfer device to transfer 50 inoculum from this plate to a second 96-well plate containing 200 µl of 2×TYAG per well. Grow with shaking at 37° C. for 2 hr. Add 50 µl 2×YTAG with $10^9$ pfu M13KO7 helper phage to each well of the second plate. Stand for 30 min at 37° C., then shake for 1 hr at 37° C.

Spin at 4000 rpm for 30 min, and then aspirate off the supernatant. Resuspend the pellet in 300 µl 2×YTAK. Grow with shaking overnight at 30° C. Spin at 4000 rpm for 30 min and use 100 µl of the culture supernatant in phage ELISA.

Coat ELISA plates with 1 µg/100 µl per well of protein antigen. Rinse wells 3 times with PBS, block with 300 µl 2% MPBS per well for 2 hr at 37° C. Rinse wells 3 times with PBS. Add 100 µl phage culture supernatant as detailed above. Incubate for 90 min at 37° C. Discard the test solution and wash three times with PBST. Add an appropriate dilution of HRP-anti-M13 antibody in 2% MPBS. Incubate for 90 min at 37° C., and wash three times with PBST.

Develop with substrate solution (TMB). Stop the reaction by adding 50 µl 1 M sulfuric acid. The color should turn yellow. Read the OD at 650 nm and at 450 nm. Subtract OD 650 from OD 450.

The results of the bio-panning from both the Dynabeads® and ELISA plate methods are shown in FIG. 7. Sequences in FIG. 7 (with their corresponding SEQ ID NOs. indicated in parentheses) show that with each heavy or light chain CDR, the sequences are highly conserved. One skilled in the art would appreciate that an antibody (or a fragment thereof) containing one or more of such CDR sequences or homologous sequences can be expected to bind the antigen (e.g., granulysin). Therefore, in accordance with embodiments of the invention, an anti-granulysin antibody may comprise one or more of these CDR sequences or homologous sequences. In accordance with embodiments of the invention, a homologous sequence may comprise 50%, 60%, 70%, 80%, 90% or higher sequence identity, as compared to the target sequence.

In accordance with embodiments of the invention, 19 specific clones have been characterized as examples. The following table shows the SEQ ID NOs. for the DNA and protein the sequences in the variable regions of the heavy chains (VH) and light chains (VL) for these 19 clones. Their specific sequences can be found in the attached sequence listing.

| Antibody | DNA SEQ ID NO | | Protein SEQ ID NO | |
|---|---|---|---|---|
| | VH | VL | VH | VL |
| GP42-15 | 1 | 2 | 39 | 40 |
| GP42-56 | 3 | 4 | 41 | 42 |
| GP42-10 | 5 | 6 | 43 | 44 |
| GP31-52 | 7 | 8 | 45 | 46 |
| GP42-58 | 9 | 10 | 47 | 48 |
| BGF32-42 | 11 | 12 | 49 | 50 |
| BGF32-48 | 13 | 14 | 51 | 52 |
| GP42-27 | 15 | 16 | 53 | 54 |
| GP42-42 | 17 | 18 | 55 | 56 |
| BGF33-19 | 19 | 20 | 57 | 58 |
| BGF31-71 | 21 | 22 | 59 | 60 |
| GP42-79 | 23 | 24 | 61 | 62 |
| GP42-09 | 25 | 26 | 63 | 64 |
| GP31-31 | 27 | 28 | 65 | 66 |
| BGF31-41 | 29 | 30 | 67 | 68 |
| BGF2A2-92 | 31 | 32 | 69 | 70 |
| M34.22 | 33 | 34 | 71 | 72 |
| M16.7 | 35 | 36 | 73 | 74 |
| M106.17 | 37 | 38 | 75 | 76 |

The above examples illustrate cloning and screening of anti-granulysin antibodies an the characterizations of the variable regions, as well as the heavy or light chain CDRs. One skilled in the art would know that the heavy chain and/or light chain sequences and CDRs may be used to generate full antibodies or fragments of the antibodies (such as scFv, Fab, F(ab)$_2$, etc.). In addition, one skilled in the art would know that the specific sequences disclosed here are for illustration only and that variations from these sequences are possible without departing from the scope of the invention. For example, one skilled in the art would know that the CDR regions are important for binding to the antigen, while the framework regions are for structural scaffold. Therefore, one often can modify the framework regions and certain CDR residues without compromising the binding of an antibody.

EXAMPLE 11

Cytotoxicity of Granulysin on Bacteria

The granulysin cytotoxicity test may be performed with any susceptible cells or bacteria. For example, *Pseudomonas aeruginosa* may be used for the assay.

In an exemplary assay, *P. aeruginosa* was grown overnight and collected by spinning at 5000 rpm for 5 min. The cells were washed with 10 mM phosphate buffer and diluted 300× with 10 mM phosphate buffer. Add 45 µl of the bacterial solution to each test mixture containing 5 µl granulysin (e.g., starting from 0.748 µg/5 µl) and 1 µl antibody (e.g., starting from original concentration and with 5× dilution). The granulysin may be *E. coli* expressed and may be 9 kDa or 15 kDa. (see, FIG. 1).

Figure 8:
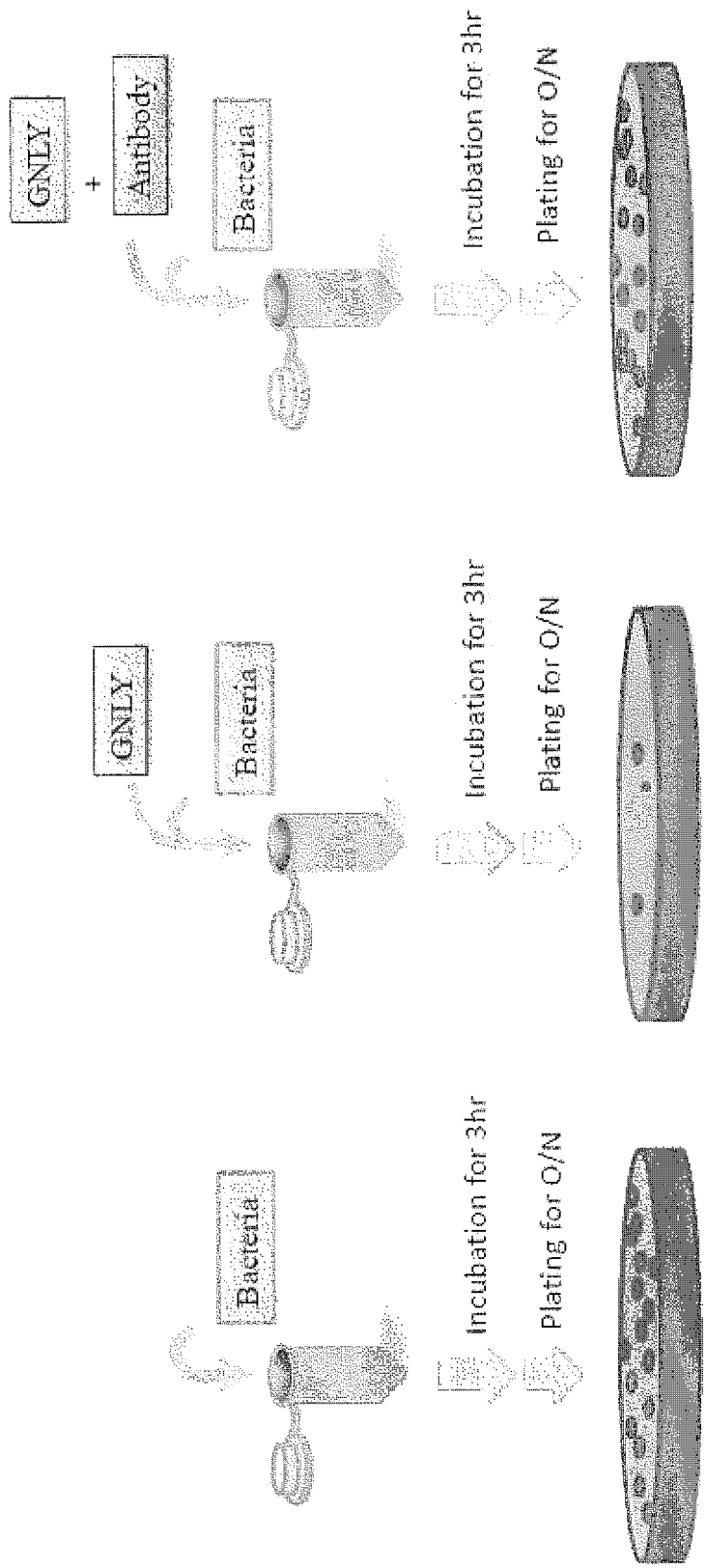
FIG. 8 shows a schematic for the assays of various anti-granulysin antibodies to reduce the antimicrobial activity of granulysin.

The mixture was incubated at 37° C. for 3 hours with rolling. The bacteria were then plated on LB plates, with dilutions if necessary (e.g., 1×, 10×, and 100× dilution), and incubated overnight. The assay procedures are illustrated in the schematics shown in FIG. 8.

Briefly, three sets of plates are incubated overnight: a control set that includes the bacteria only, a lysis set that includes granulysin (0.5 µg) and the same number of bacteria, and an antibody set that includes the same number of bacteria, granulysin (0.5 µg), and a test antibody (which may be tested at different concentrations (e.g., 0.4 µg and 2.0 µg) by adding more sets of plates). As illustrated schematically in FIG. 8, granulysin is expected to lyse the bacteria, resulting in few colonies. With addition of an antibody that can counter the action of granulysin, one would expect that the bacteria would be protected and the colony number may be restored to that similar to the control set.

Figure 9:
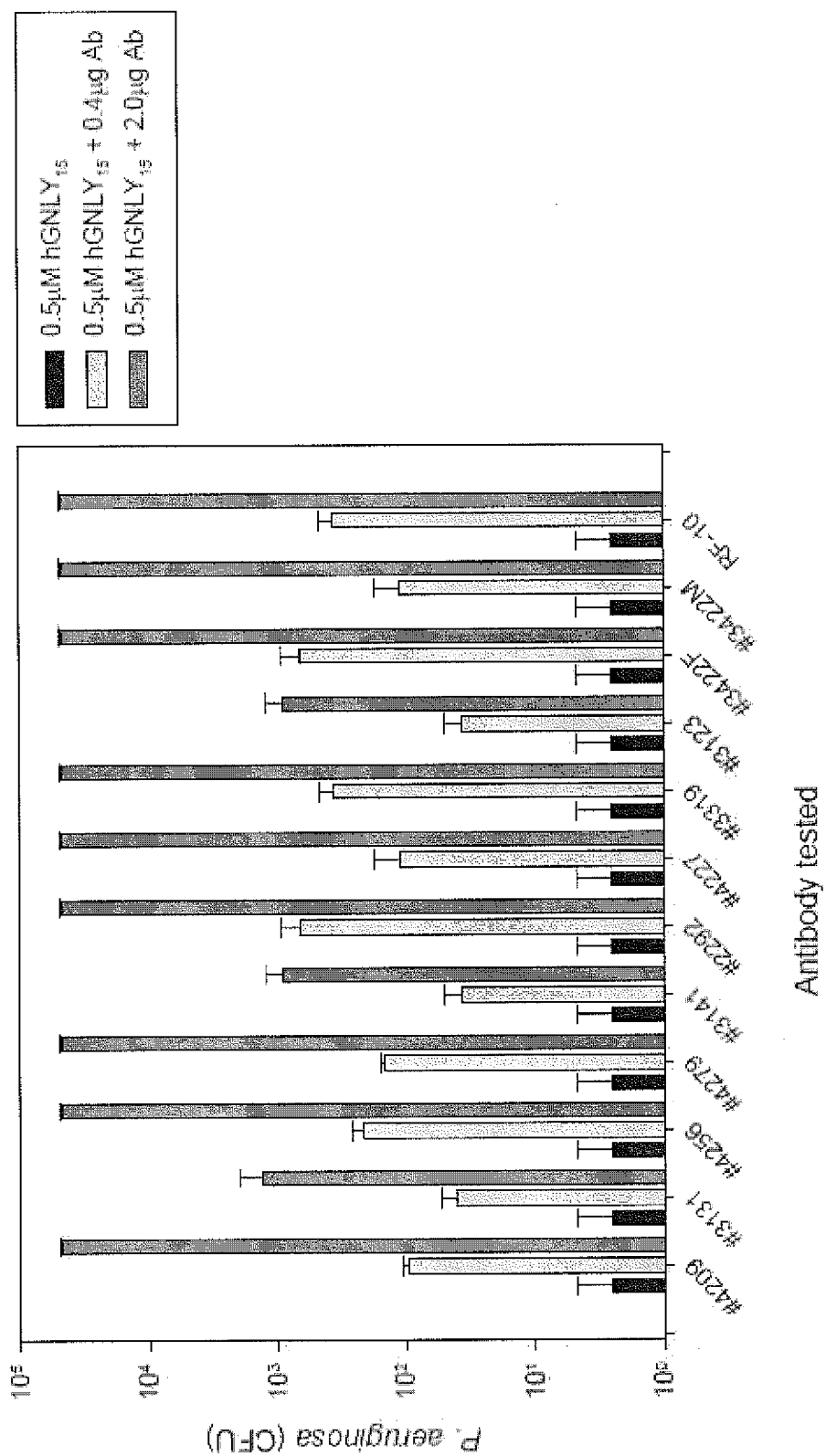
FIG. 9 shows results of various anti-granulysin antibodies to reduce the antimicrobial activity of granulysin.
Figure 10:
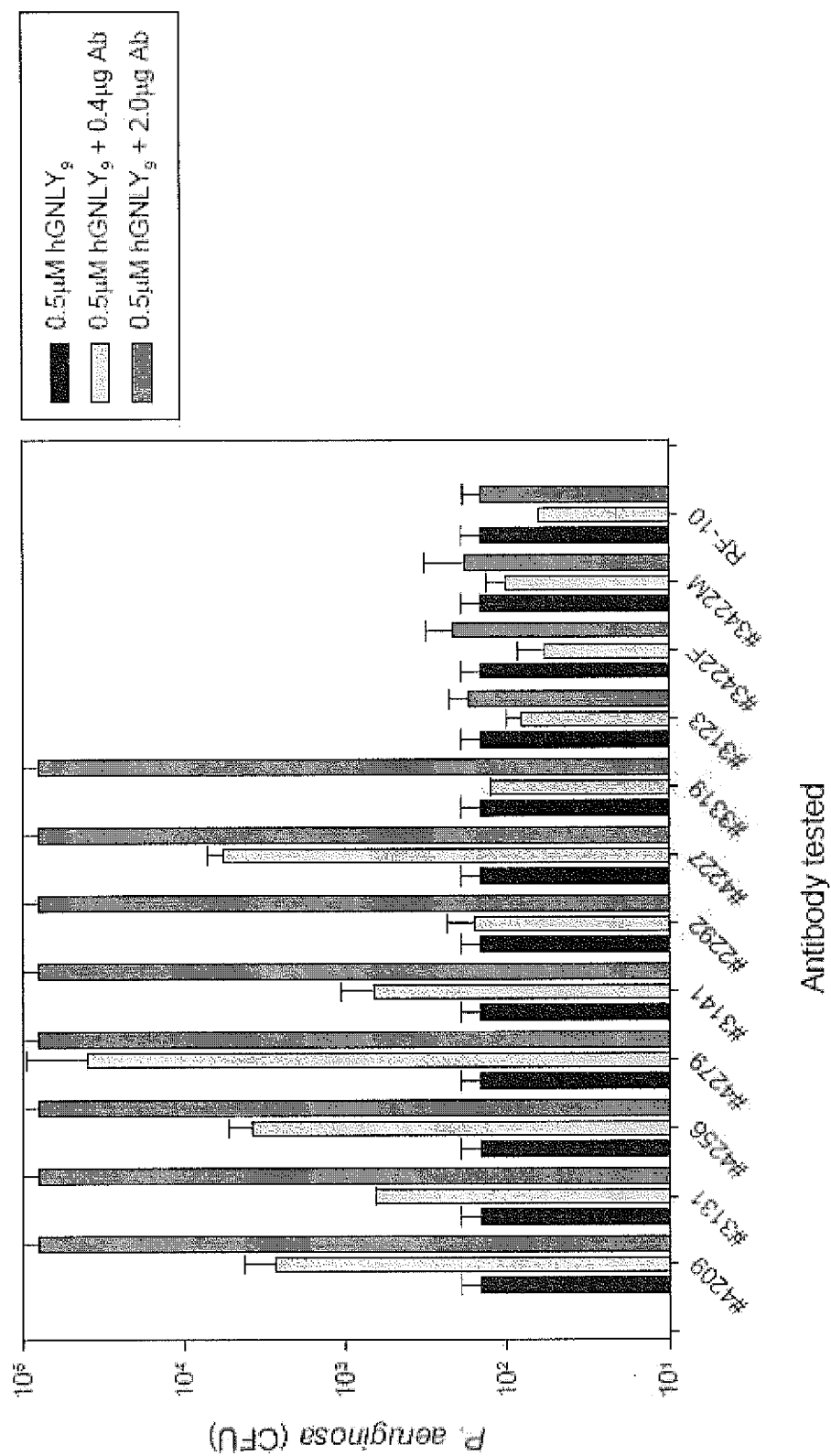
FIG. 10 shows results of various anti-granulysin antibodies to reduce the antimicrobial activity of granulysin.

The results from the assays are shown in FIG. 9 and FIG. 10. As shown in FIG. 9, all test antibodies showed very good effects in protecting the bacteria from lysis caused by the 15 kDa granulysin (0.5 µg). Even at 0.4 µg antibody dose, all are effective. With an increased dose (2.0 µg antibody), most antibodies completely inhibited the lysis caused by granulysin.

FIG. 10 shows results of a similar test using the 9 kDa granulysin instead of a 15 kDa granulysin. The results shown in FIG. 10 are mostly similar to those in FIG. 9, except for four antibodies (#3123, #422F, #422M, and RF-10), which did not show appreciable protective activity. These four antibodies show very good activities against granulysin-induced lysis when the tests were conducted with 15 kDa granulysin. The difference in activities is most likely due to the fact that an N-terminal segment is present in the 15 kDa granulysin, but not in the 9 kDa granulysin (see FIG. 1). Therefore, these tests revealed the epitopes for these four antibodies are located within the N-terminal segment that is missing in the 9 kDa granulysin. By the same token, the epitope locations for the other eight antibodies (#4209, #3131, #4256, #4279, #3141, #2292, #4227, and #3319) are located in the region that is common in both 9 kDa and 15 kDa granulysins.

Results from the lysis assays based on the antimicrobial (lysis) activity of granulysin are consistent with those assayed using keratinocytes described above (FIG. 5), confirming that these antibodies can neutralize granulysin lysis activity. These results indicate that these antibodies can also be used to prevent granulysin-mediated disorders, such as SJS, TEN, and GVHD.

EXAMPLE 12

Affinity Measurements and Kinetic Analysis

For use as therapeutic agents, antibodies should preferably have good affinities to the target molecule (e.g., granulysin). The affinities and kinetics of various antibodies binding to granulysin may be assessed using any suitable instrument, such as an SPR-based assay on BIAcore T100. For example, the binding kinetics were measured and analyzed by multi-cycle kinetics (MCK) method using the associated software.

As an example, granulysin was immobilized on CM5 chips at a density that allowed one to achieve $R_{max}$ in the range of 50-150 Response Units (RU).

In this example, the kinetic assay parameters were as follows: data collection rate 1 Hz; dual detection mode; temperature: 25° C.; concentration unit: nM; and buffer A HBS-EP. The measurements were performed with 5 replicates. The various instrument settings are as follows:

The analyte sample parameters are as follows: Type: multi-cycle kinetics, Contact time: 420 s, Flow rate: 10 μL/min How path: Both, Stabilization period: 90 s.

The Regeneration parameters are as follows: Regeneration solution: 25 mM Glycine pH 1.5, Contact time: 90 s, Flow Rate: 30 μL/min, Flow path: Both.

The Startup cycle parameters are as follows: Type: Low sample consumption, Contact time: 420 s, Dissociation time: 600 s, Flow rate: 30 μL/min, Flow path: Both.

The Sample cycle parameters are as follows: Type: multi-cycle kinetics, Contact time: 420 s, Dissociation time: 600 s, Flow rate: 30 μL/min, Flow path: Both.

The anti-granulysin antibodies were serially diluted with the running buffer. The serial concentrations obtained were 40, 20, 10, 5, 2.5, 1.25, 0.625, 0.3125, 0 and 1.25 nM (repeat).

The results were evaluated with the BIAcoreT100 evaluation software. The binding responses were corrected for buffer effects by subtracting responses from a blank flow cell. A 1:1 Langmuir fitting model was used to estimate the $k_a$ or $k_{on}$ (association rate or on-rate) and $k_d$ or $k_{off}$ (dissociation rate or off-rate). The $K_D$ (or $K_d$) values may be determined from the ratios of $k_{off}$ and $k_{on}$ (i.e., $K_d = k_{off}/k_{on}$). Alternatively, the dissociation constants ($K_d$ values) may be estimated from the steady-state bound form concentration (i.e., the plateau portions of the curve in FIG. 11) as a function of the antibody concentrations based on an equilibrium kinetics similar to the Michaelis-Menton equation, and the on rate ($k_{on}$) can be estimated from the curved portions in FIG. 11 by fitting a first-order reaction kinetics. (The reaction is first order because one of the reagent is held at a constant concentration.) Then, the $k_{off}$ rates may be derived from $K_d$ and $k_{on}$.

Figure 11:
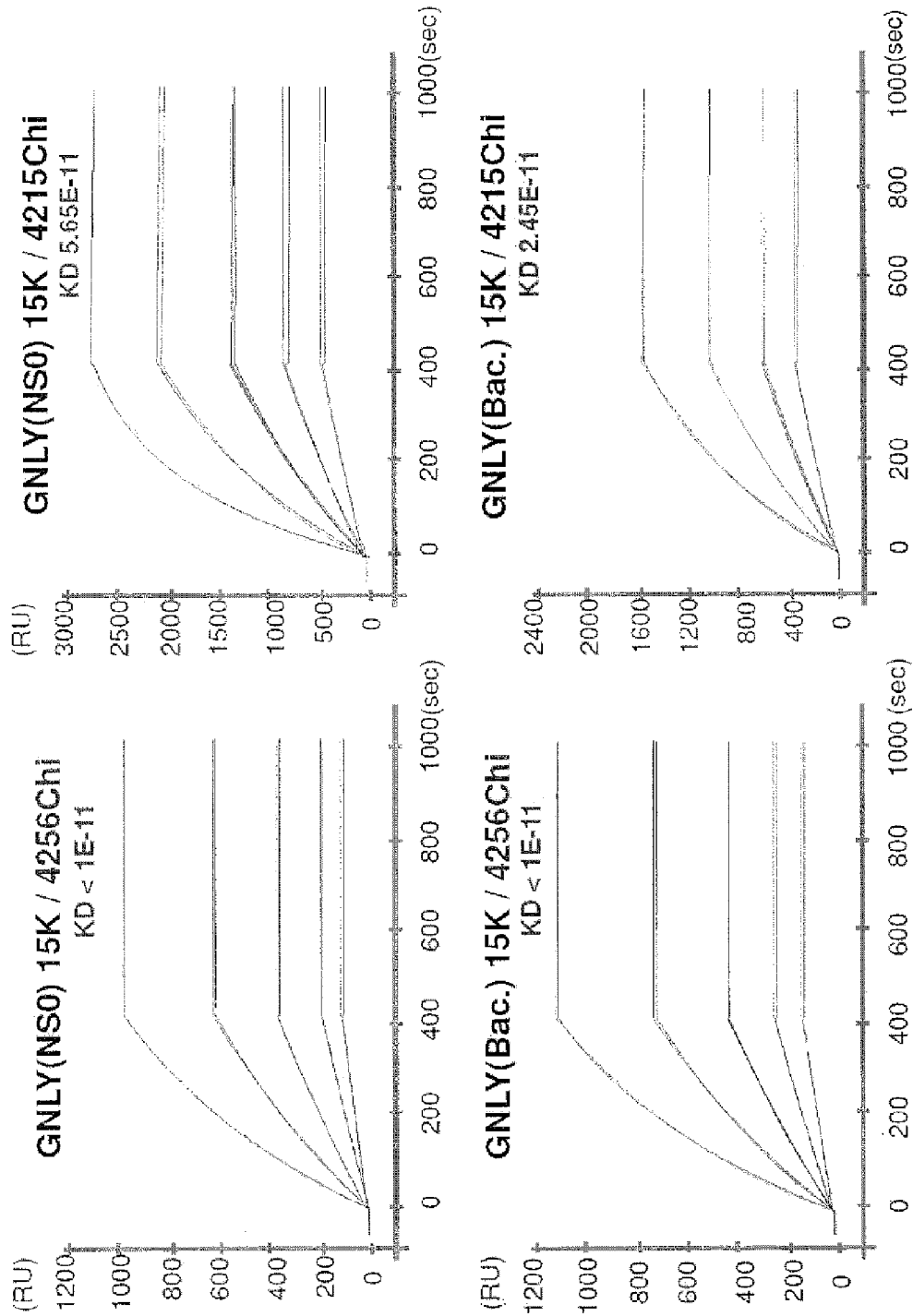
FIG. 11 shows kinetic assays of bindings of various anti-granulysin antibodies to granulysin.

As shown in FIG. 11, the binding affinities (measured as dissociation constant $K_d$) are very good. For all antibodies shown in FIG. 11, the $K_d$ values are sub nM (ranging from low $10^{-10}$ M to less than $10^{-11}$ M). These data indicate that these antibodies can be effective therapeutic agents.

EXAMPLE 13

Epitope Mapping

In order to elucidate the residues involved in the biding of the antibodies to granulysin, epitope mapping experiments were performed. Specifically, alanine-scanning method was used to identify residues on granulysin that are critical for antibody binding. The kinetics and affinities of these granulysin mutants were assessed in the same manners described above. The assays can be performed with various mutants in combination with various antibodies (particularly neutralizing antibodies). Results from these binding studies would allow one to identify not only critical residues on granulysin, but also important residues in the CDR's.

Granulysin may exist in a 9 kD or a 15 kD form. The DNA and protein sequences for these forms are shown below:

SEQ ID NO 77: (granulysin 9 kD)
GRDYRTCLTIVQKLKKMVDKPTQRSVSNAATRVCRTGRSRWRDVCRNFMR

RYQSRVTQGLVAGETAQQICEDLR

SEQ ID NO 78: (granulysin 9 kD)
ggccgtgactacaggacctgtctgacgatagtccaaaaactgaagaagat ggtggataagcccacccagagaagtgtttccaatgctgcgacccgggtgt gtaggacggggaggtcacgatggcgcgacgtctgcagaaatttcatgagg aggtatcagtctagagttacccagggcctcgtggccggagaaactgccca gcagatctgtgaggacctcagg SEQ ID NO 79: (Granulysin 15 kD)
MATWALLLLAAMLLGNPGLVFSRLSPEYYDLARAHLRDEEKSCPCLAQEG

PQGDLLTKTQELGRDYRTCLTIVQKLKKMVDKPTQRSVSNAATRVCRTGR

SRWRDVCRNFMRRYQSRVTQGLVAGETAQQICEDLRLCIPSTGPL

SEQ ID NO 80: (Granulysin 15 kD)
atggctacctgggccctcctgctccttgcagccatgctcctgggcaaccc aggtctggtcttctctcgtctgagccctgagtactacgacctggcaagag cccacctgcgtgatgaggagaaatcctgcccgtgcctggcccaggagggc ccccagggtgacctgttgaccaaaacacaggagctgggccgtgactacag gacctgtctgacgatagtccaaaaactgaagaagatggtggataagccca cccagagaagtgtttccaatgctgcgacccgggtgtgtaggacggggagg tcacgatggcgcgacgtctgcagaaatttcatgaggaggtatcagtctag -continued

```
agttacccagggcctcgtggccggagaaactgcccagcagatctgtgagg acctcaggttgtgtataccttctacaggtcccctctga
```

Figure 2:
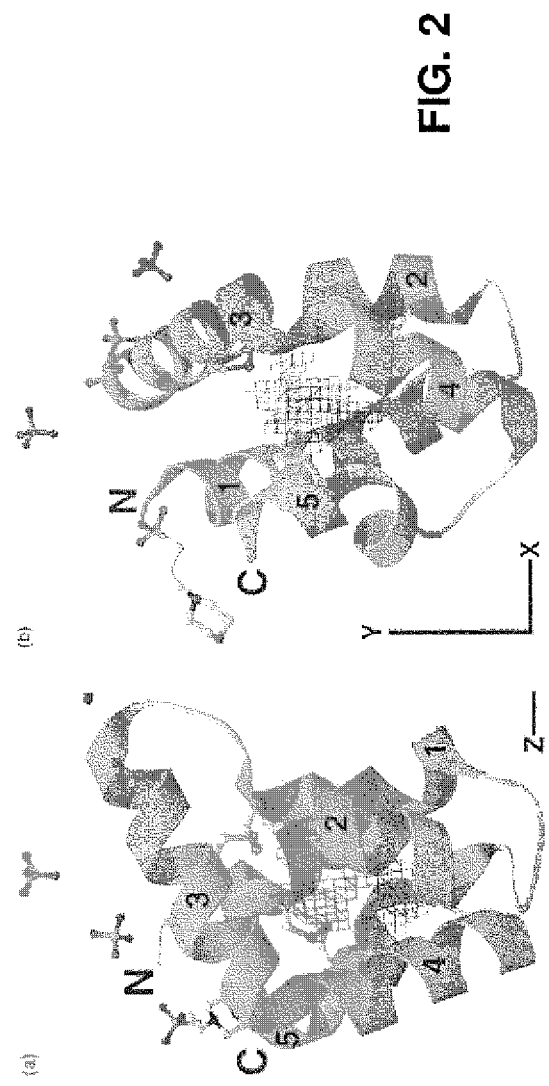
FIG. 2 shows the three-dimensional structure of granulysin illustrating the five-helix bundle.
Figure 3:
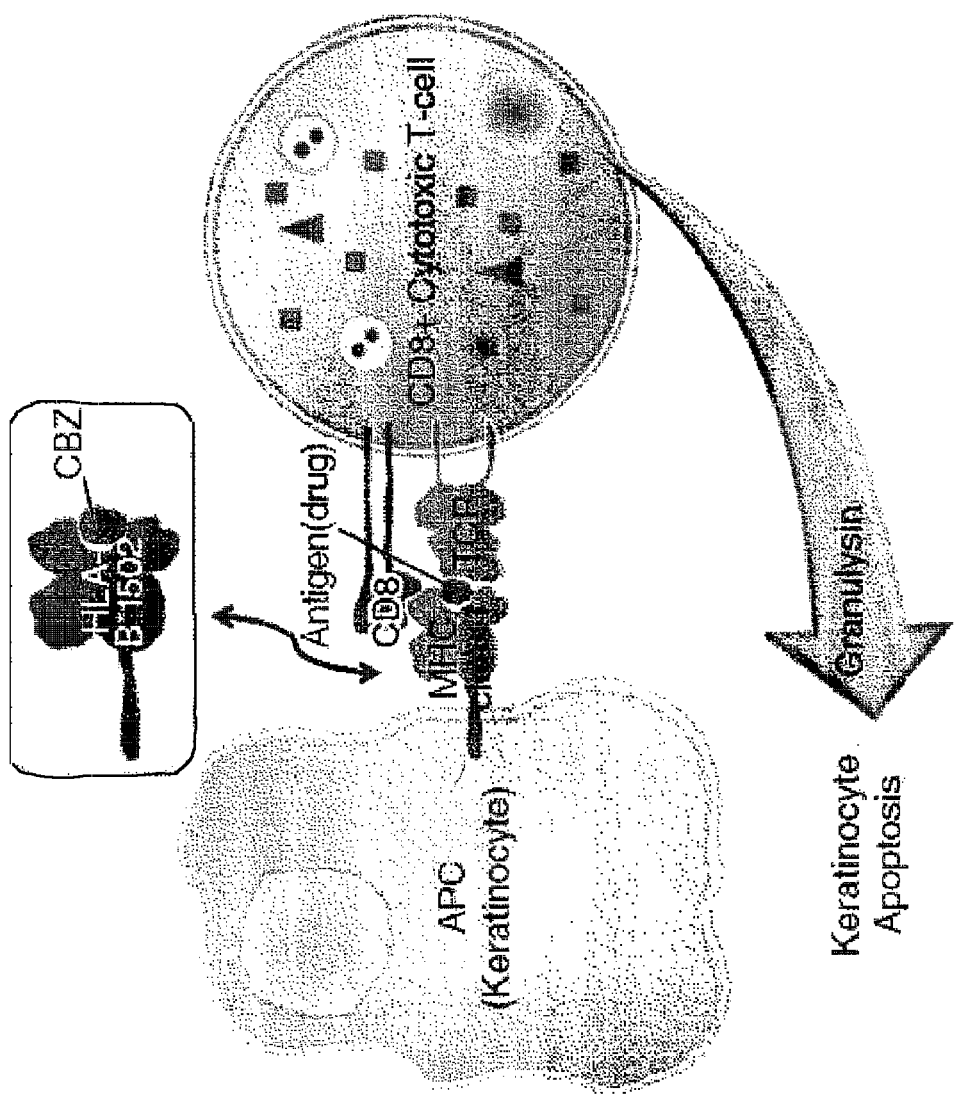
FIG. 3 shows a schematic illustrating a possible mechanism involved in granulysin-mediated cytotoxicity.

As noted above, granulysin forms a five-helix bundle with arginine positioned on one side of the molecule (see FIG. 2). FIG. 16 shows the crystal structure of granulysin. From this structure, it is seen that seven arginine residues (64, 97, 100, 102, 104, 108, and 113) are located on one side of the molecule. These positively charged amino acids are presumably critical for granulysin activities. Therefore, mutations may be made at these locations for evaluation of the importance of the residues on granulysin.

Figure 12:
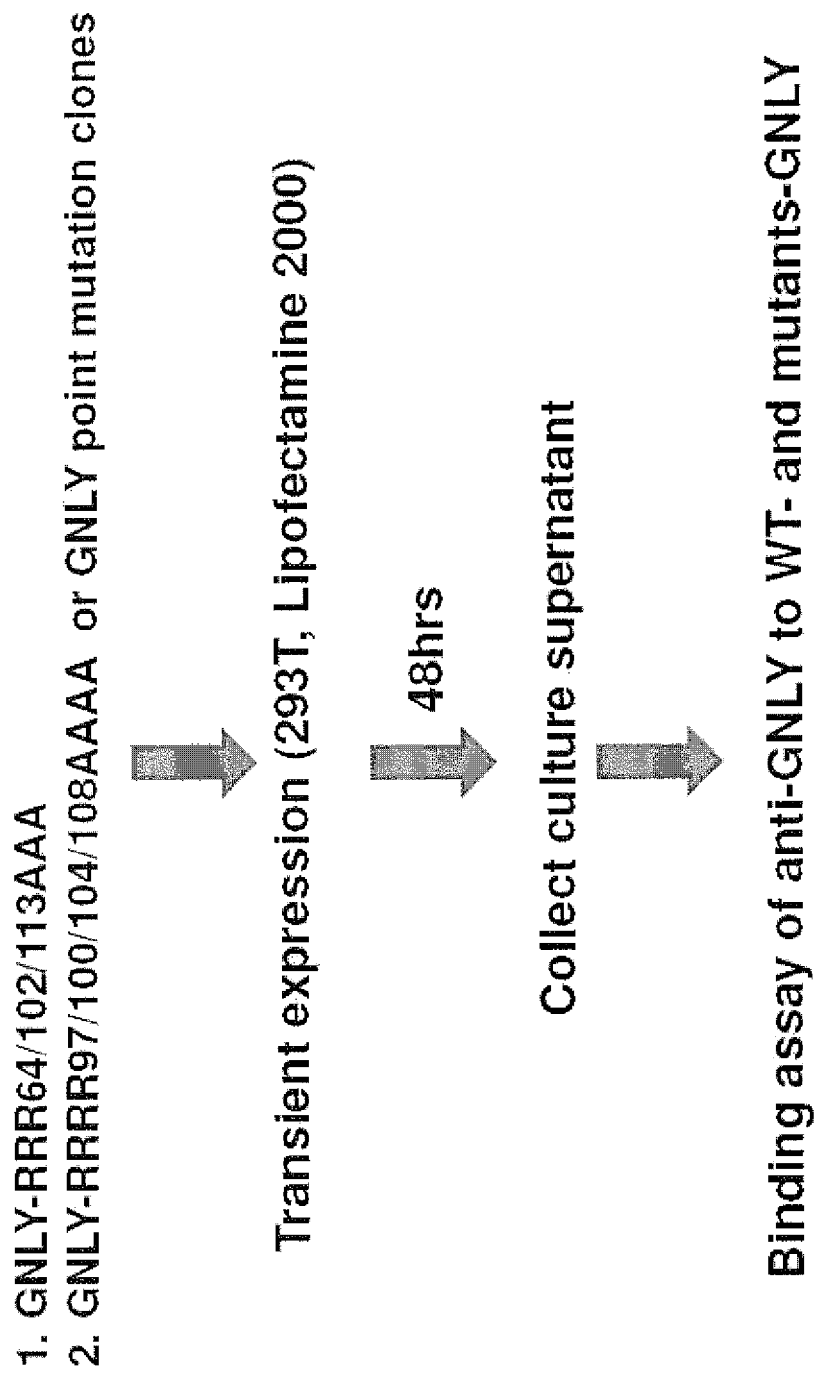
FIG. 12 shows a schematic for the production of mutants of granulysins.

For example, FIG. 12 illustrates a scheme for producing granulysin mutants for the studies. In this example, a few mutants were generated, for example, by substituting arginines at 64, 102, and 113 with alanines, while the other mutant has substitutions at arginines. 97, 100, 104, and 108. In addition to these two examples, several single mutations and/or mutations at non-arginine locations were also generated. Furthermore, to facilitate the purification and detection of the expressed proteins, one or more tag sequences (e.g., His tag) may be attached to either the N-terminus or the C-terminus of the protein.

As shown in FIG. 12, the mutants may be expressed in a suitable cell using any method known in the art, for example, transient transfection using lipofectamine 2000 into 293T cells. The transfected cells were cultured for a suitable duration (e.g., 48 hours) for the transfected cells to produce the mutant granulysins. The produced mutant granulysins can be collected from culture supernatant and used to assay for their bindings with anti-granulysin antibodies.

Binding Assays of Anti-Granulysin Antibodies to Wild-Type and Mutant Granulysins The binding assays can be performed in a manner similar to those described above using Dynabeads® or ELISA plates.

As an example, using ELISA plates, each well may be coated with an anti-granulysin antibody at a suitable concentration (e.g., 5 µg/ml) in a suitable buffer (e.g., 50 mM phosphate buffer, pH 9.6) at 4° C. overnight.

To the antibody-coated plates, 200 µl of serially diluted samples (wild-type or mutant granulysin) were added to each well. The solutions were then incubated at 37° C. for 2 hours.

After washing to remove the unbound proteins, the bound proteins that were produced with His-tag (or any other tag or a fusion protein), can be detected with an anti-H is antibody coupled with HRP (for example, Sigma, A7058) at an appropriate dilution (e.g., 1:2000). The secondary antibodies were allowed to bind to the bound proteins by incubation at 37° C. for 2 hours (or any suitable duration and temperatures).

After the incubation, excess secondary antibodies were washed away and the bound secondary antibodies were quantified using 100 µl TMB. The enzymatic reaction may be stopped with addition of 100 µl of $H_2SO_4$. The reaction products were quantified by OD 450-655 nm.

FIGS. 13A-13O show exemplary results from the kinetic studies for various granulysin mutants binding with various antibodies. As shown in FIGS. 13A-13O, most antibodies lost all or most bindings to the granulysin mutants that contain alanine substitutions for arginines (e.g., RRR64/102/113AAA and RRRR97/100/104/108AAAA), indicating that these antibodies do bind to (or near) the positively-charged face of the native granulysin molecule. A few exceptions are shown in FIGS. 13I, 13J, 13M, 13N, and 13O.

As shown in FIG. 13I, antibody BGF33-19 actually binds tighter to the mutant granulysins, as evidenced by the left shifts of the binding curves, as compare to the binding to the wild-type granulysin. The tighter binding was observed for both the RR64/67AA mutant and the RRR64/102/113AAA mutant. The tighter binding may result from a conformational change in the mutant protein, from the generation of a favorable interaction (alanine is more hydrophobic than arginine), or from the loss of unfavorable interactions in the wild-type molecule (for example, R64 positive charge may interfere with the antibody binding).

Figure 13:
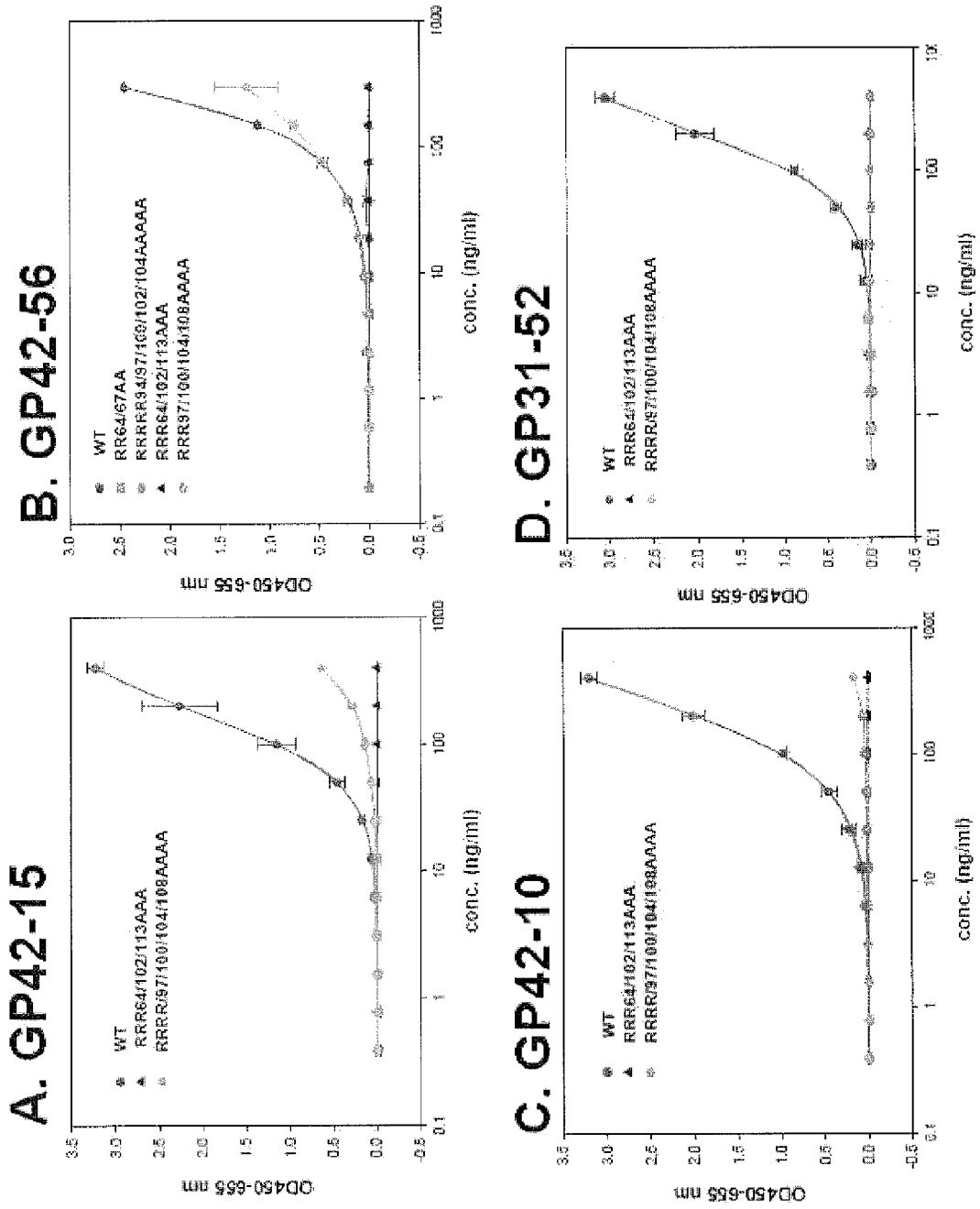
FIGS. 13A-13O show various assays of bindings of various anti-granulysin antibodies to granulysin and mutant granulysins.
Figure 14:
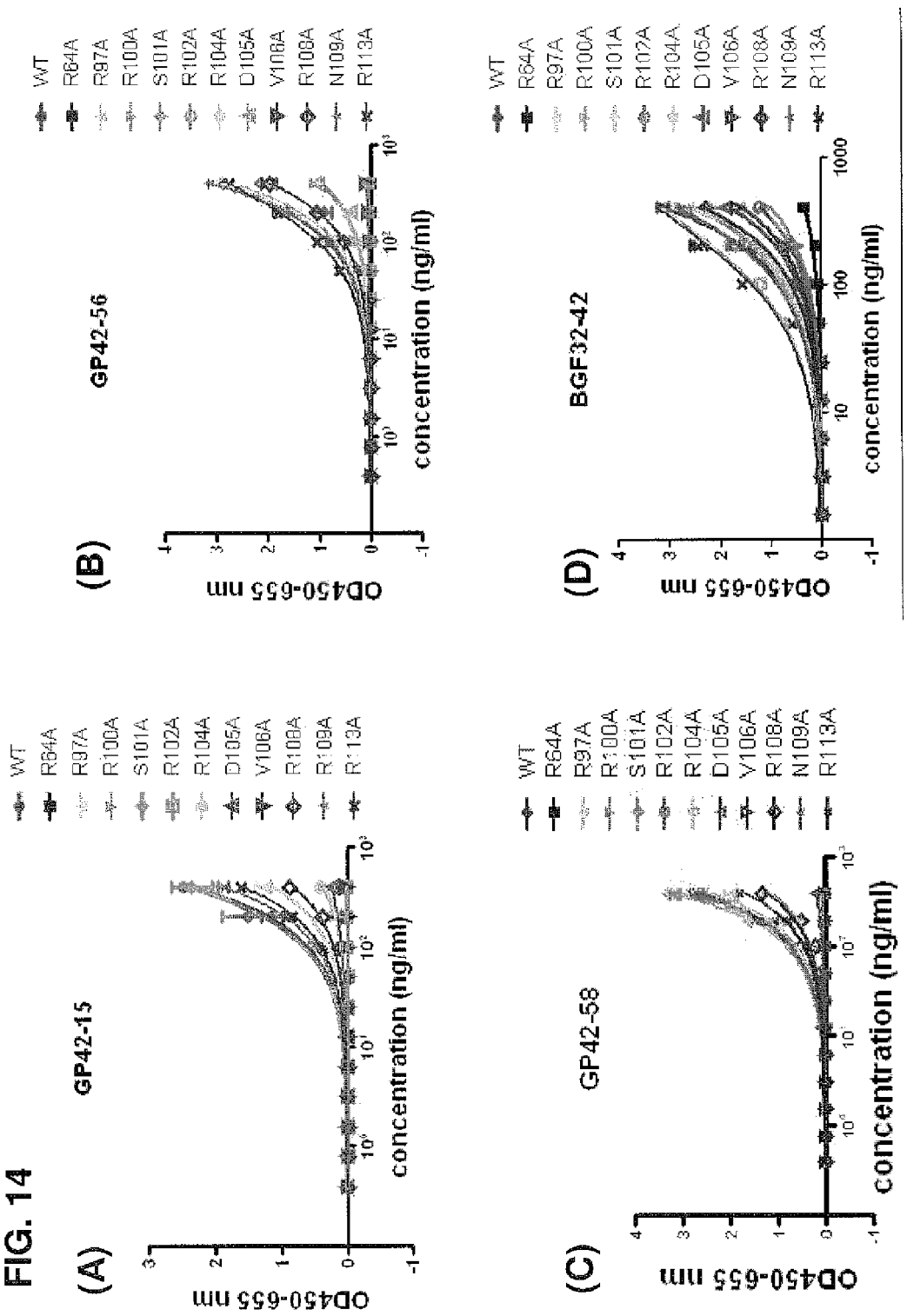
FIGS. 14A-14J show various assays of bindings of various anti-granulysin antibodies to granulysins with point mutations (single amino acid alanine scanning).
Figure 14:
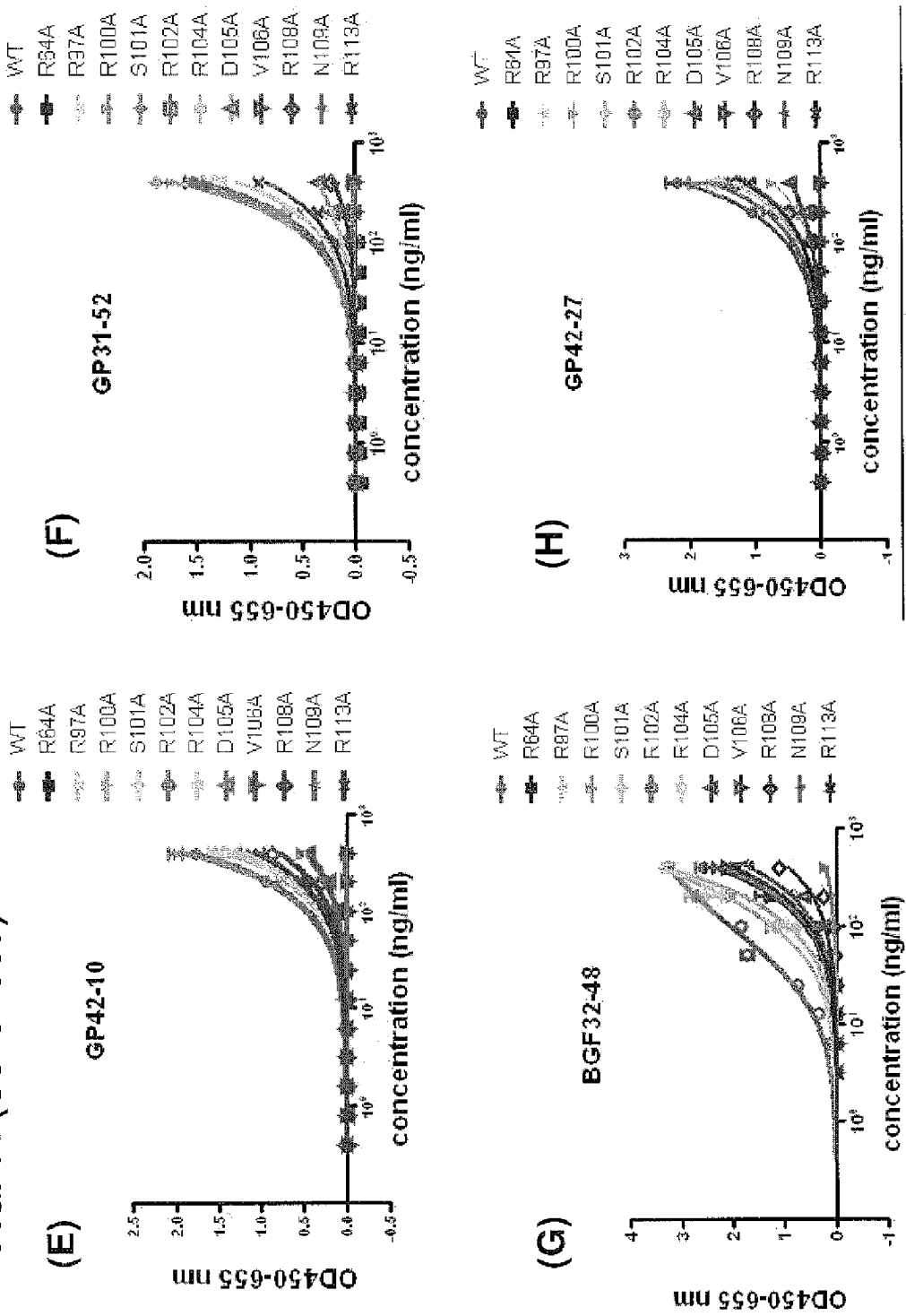
Figure 14:
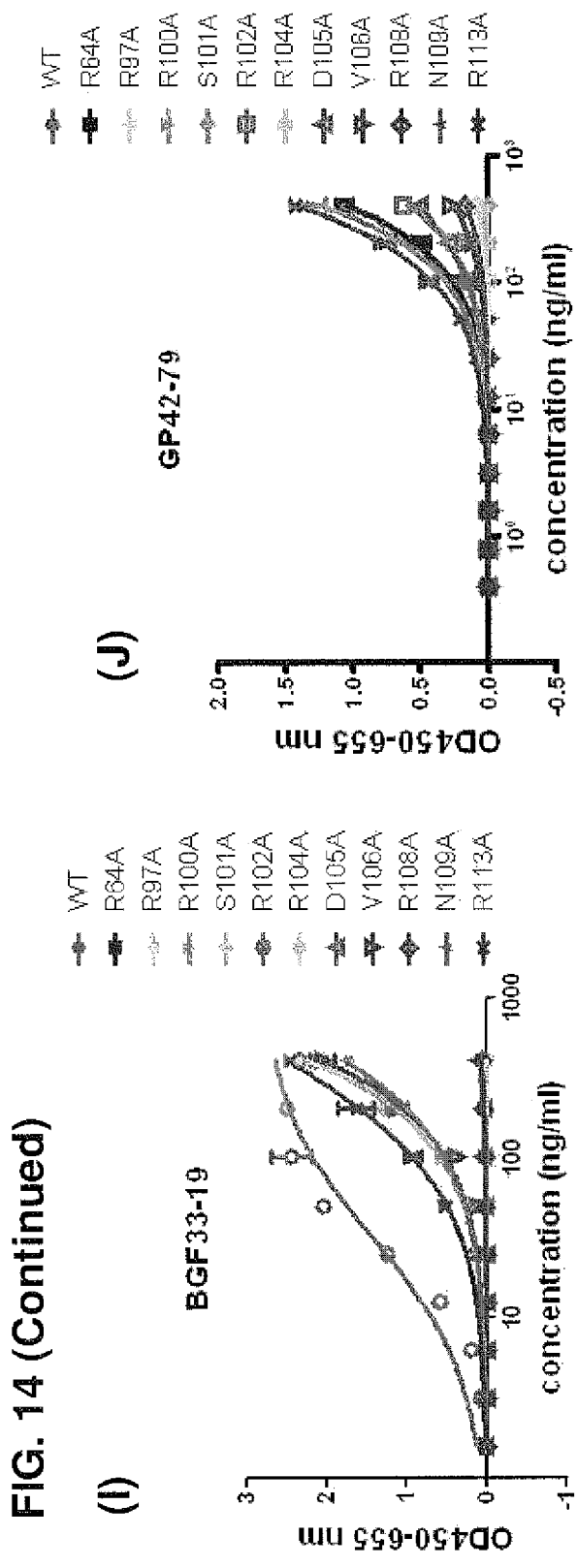

However, for the RRRRR94/97/100/102/104AAAAA mutant and the RRRR97/100/104/108AAAA mutant, the bindings between the BGF33-19 antibody and the mutant proteins are essentially wiped out. This result indicates that the positive charges located in the lower half on the face of the molecule as shown in FIG. 13 may be important for antigen-antibody bindings.

Referring to FIG. 13J, the binding of antibody BGF31-71 to the RRR64/102/113 mutant is enhanced, while the binding to the RRRR97/100/104/108AAA mutant is significantly weakened. These results also suggest that the positive charges in the lower half on the face shown in FIG. 16 may be important for the antibody binding, while the positive charges on the top half on the face shown in FIG. 16 may interfere with antibody binding. These results are consistent with that observed with antibody BGF33-19 shown in FIG. 13I.

Referring to FIG. 13M, the binding of antibody GP31-31 to the RRR64/102/113 mutant and the RRRR97/100/104/108AAA mutant are not changed. These results indicate that this antibody probably binds to other surfaces on the granulysin molecule.

Referring to FIG. 13N, the binding of antibody BGF31-41 to the RRR64/102/113 mutant and the RRRR97/100/104/108AAA mutant are both enhanced. These results indicate that this antibody probably binds to another part on the granulysin molecule and that removal of the arginine positive charges produced more favorable bindings (perhaps due to conformational changes).

Referring to FIG. 13O, the binding of antibody BGF2A2-92 to the RRR64/102/113 mutant is enhanced, while the binding to the RRRR97/100/104/108AAA mutant is completely wiped out. These results indicate that this antibody probably bind to the lower half on the face shown in FIG. 16 and the positive charges in that region are important for the binding.

In sum, the results shown in FIGS. 13A-13O indicate that many antibodies probably bind to the lower half on the face shown in FIG. 16 and that the positive charges in this region do contribute to the bindings with these antibodies. In other words, this region is probably more antigenic (or containing more epitopes) than other parts of the granulysin molecule.

To bind epitopes containing positive charged arginine residues, the antibody binding sites (i.e., CDRs) probably contain negatively charged residues. Indeed, the CDR sequences all contain one or more negatively charged residues (e.g., aspartic acid or glutamic acid; FIG. 7). Particularly, CDRH2 and CDRH3 all contain multiple negatively charged residues.

While the assays shown in FIGS. 13A-13O were performed with alanine scanning of arginine residues, one may also perform alanine scanning at other locations on the granulysin protein. FIGS. 14A-14J, for example, show some examples in which various residues on granulysin had been replaced with alanines. The various binding curves between these mutant granulysins and different antibodies are shown. Using these single alanine scannings, one can pinpoint the residues that are important for antibody bindings. This allows one to map the epitope of any particular antibody on the granulysin protein.

The fact that most neutralizing antibodies of the invention bind to the arginine rich region suggests that the arginines are involved in its function. FIG. 15 shows a schematic illustrating a model of the interactions between the granulysin molecule (via its positively charge side) and the negatively charged phospholipid layers.

Figure 17:
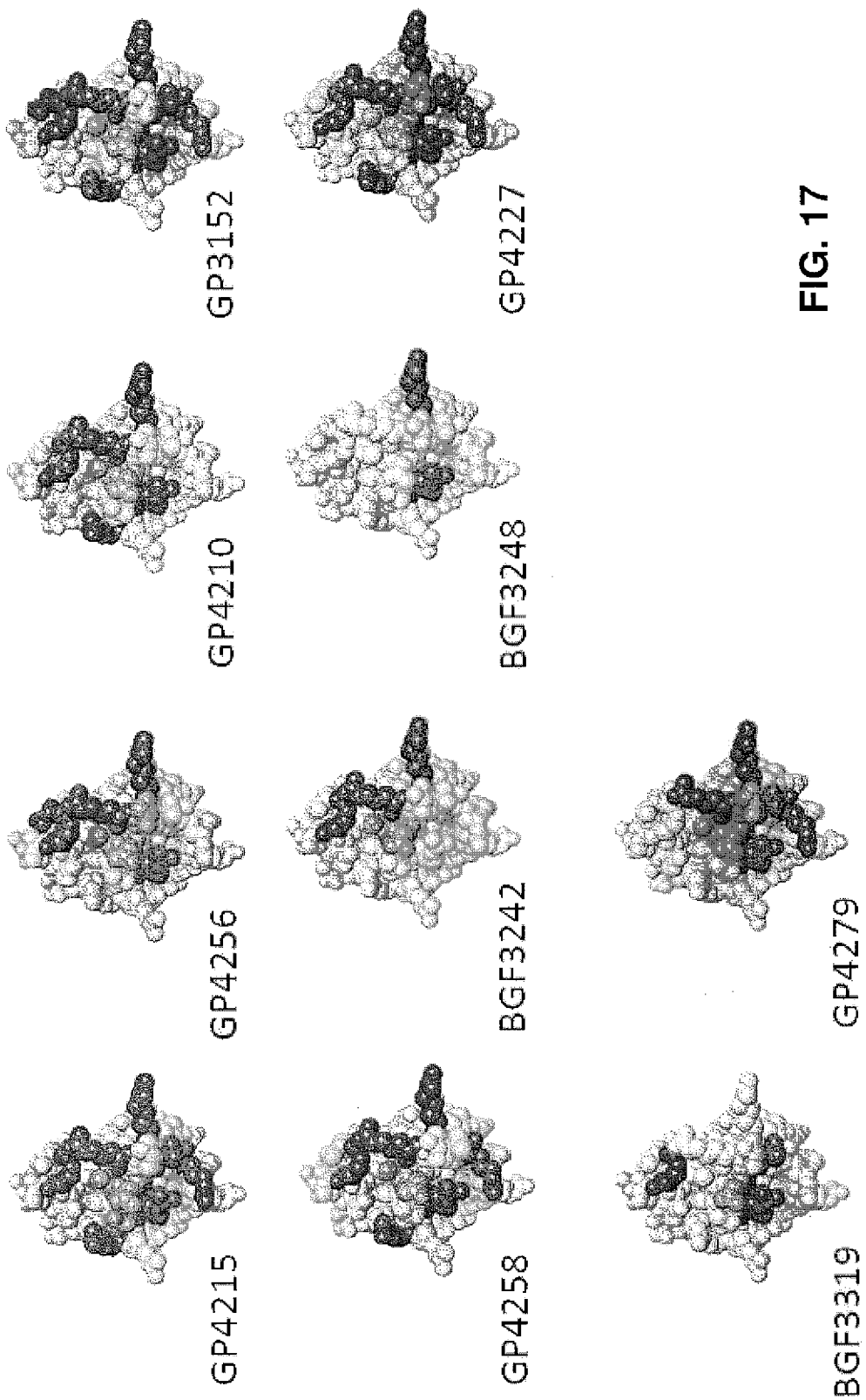
FIG. 17 shows various epitopes on granulysin proteins for different monoclonal antibodies.

In addition to arginines, the "binding face" of the granulysin also contains other residues that may be involved in antibody binding (see FIG. 16). Such residues may include S101, V106, D108, and N109. FIG. 17 shows a few examples of epitopes on the granulysin for several antibodies. From these results, one can conclude that the epitopes on the granulysin is located in the sequence from residues R64 to R113 (SEQ ID NO: 81).

```
                                                SEQ ID NO: 81
(Granulysin epitope region)
RDYRTCLTIVQKLKKMVDKPTQRSVSNAATRVCRTGR SRWRDVCRNFMR
R
```

FIG. 18 summarizes the results of various antibodies, showing their affinities (shown as dissociation constants, $K_D$) to the 9 kDa and 15 kDa granulysins, their abilities to neutralize the antimicrobial activities of granulysin, and whether they bind to denatured granulysin. Analysis of these sequences and their binding constants would allow one to elucidate the important residues in the various CDR's, i.e., to deduce consensus sequences, as noted above.

Furthermore, by comparing the binding to the native and denatured granulysins, one can conclude whether the antibodies bind to conformational epitopes. For example, FIG. 19 outlines an exemplary procedure for assessing antibody bindings to the denatured granulysin. Briefly, granulysin may be transiently expressed with a 10His tag to facilitate the purification. The transient expression may be performed according to any method known in the art (for example, using lipofectamine 2000 and 293T cells). After a suitable incubation period (e.g., 48 hours), the culture supernatant may be collected for the assay. The amount of expression may be quantified using any known methods, such as using ELISA.

The expressed granulysin may be run on a denatured SDS-PAGE and then probed with the test antibodies. Whether the test antibodies bind to the denatured granulysin can be detected using a secondary antibody (containing a reporter group; e.g., anti-human-HRP). Based on this assay, the abilities of the antibodies to bind to the denatured granulysin are shown in FIG. 18.

As shown in FIG. 18, antibodies GP42-10, GP31-52, GP42-58, GP42-27, BGF33-19, BGF31-71, GP42-09, GP31-31, BGF2A2-92, 34.22Chi, 16.7Chi, and 106.17Chi (a chimeric antibody of the variable region of M34.22, M16.7, or M106.17 fused with the constant region of human IgG1, respectively) did not bind to denatured granulysin, suggesting that these antibodies may recognize conformational epitopes.

The nucleotide and amino acid sequences of various antibodies are shown in the sequence listing attached hereto.

Human Antibodies and Humanized Antibodies

In accordance with some embodiments of the invention, an antibody may be a fully human antibody (e.g., an antibody produced in a mouse engineered to produce an antibody from a human immunoglobulin sequence). Human monoclonal antibodies can be generated using transgenic mice carrying the human immunoglobulin genes rather than the mouse genes. Splenocytes from these transgenic mice immunized with an antigen of interest (e.g., granulysin) may be used to produce hybridomas that secrete human mAbs with specific affinities for epitopes from a human protein (see, e.g., Wood et al. WO 91/00906, Kucherlapati et al. WO 91/10741; Lonberg et al. WO92/03918; Kay et al. 92/03917; Lonberg, N, et al. 1994 Nature 368:856-859; Green, L. L. et al. 1994 Nature Genet. 7:13-21; Morrison et al. 1994 Proc. Natl. Acad. Sci. USA 81:6851-6855; Bruggeman et al. 1993 Immunol 7:33-40; Tuaillon et al. 1993 PNAS 90:3720-3724; Bruggeman et al. 1991 Eur J Immunol 21:1323-1326).

In addition, antibodies may be generated in a non-human organism, e.g., a rat or mouse, and then modified, e.g., in the variable framework or constant region, to decrease antigenicity in a human. These antibodies may be referred to as "humanized antibodies." Techniques for humanizing antibodies are known in the art (see below).

As a variation of a humanized antibody, chimeric antibodies can be produced by recombinant DNA techniques known in the art. For example, a gene encoding the Fc constant region of a murine (or other species) monoclonal antibody molecule may be digested with restriction enzymes to remove the region encoding the murine Fc, and the equivalent portion of a gene encoding a human Fc constant region is substituted (see Akira, et al., EP Application No. 184,187; Cabilly et al. U.S. Pat. No. 4,816,567; Cabilly et al., Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. et al (1985) Nature 314:446-449; and Shaw et al., 1988, J. Natl Cancer Inst. 80:1553-1559).

A humanized or CDR-grafted antibody will have at least one or two but generally all three recipient CDR's (of heavy and/or light chains) replaced with a donor CDR. The antibody may be replaced with at least a portion of a non-human CDR or only some of the CDR's may be replaced with non-human CDR's. It is only necessary to replace the number of CDR's required for binding of the humanized antibody or a fragment thereof. Preferably, the donor may be a rodent antibody, e.g., a rat or mouse antibody, and the recipient is a human framework or a human consensus framework. A consensus framework may have a sequence about 85% or higher, preferably 90%, 95%, 99% or higher identical to the human framework.

As used herein, the term "consensus sequence" refers to the sequence formed from the most frequently occurring amino acids (or nucleotides) in a family of related sequences (See e.g., Winnaker, From Genes to clones (Verlagsgesellschaft, Weinheim, Germany 1987). In a family of proteins, each position in the consensus sequence is occupied by the amino acid occurring most frequently at the position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable regions, which are not directly involved in antigen binding with equivalent sequences from human Fv variable regions. General methods for generating humanized antibodies are provided by Morrison, S. L., 1985, Science 229:1202-1207; by Oi et al., 1986, BioTechniques 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a polypeptide of interest or fragment thereof. The recombinant DNA encoding the humanized antibody, or fragment thereof, can then be cloned into an appropriate expression vector.

In addition, humanized antibodies, in which specific amino acids have been substituted, deleted or added, may be fused with a scaffold. Preferred humanized antibodies have amino acid substitutions in the framework region, such as to improve binding to an antigen. For example, a humanized antibody may have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR. Criteria for selecting amino acids from the donor are described in U.S. Pat. No. 5,585,089, the contents of which are hereby incorporated by reference. Other techniques for humanizing antibodies are described in Padlan et al. EP519596 A1.

Treatment Methods

The invention also relates to methods for treating or preventing one or more of the above described disorders, such as SJS, TEN, or GVHD using anti-granulysin antibodies. In accordance with embodiments of the invention, the antibodies may be monoclonal antibodies. Such antibodies may be humanized antibodies or human antibodies. In accordance with embodiments of the invention, a subject in need of such treatment or prevention will be given an effective amount of the antibody.

A subject to be treated can be identified by standard diagnosing techniques for such a disorder. Alternatively, the subject can be examined for the gene expression or activity level of the granulysin polypeptide. If the gene expression or activity level is higher in a sample from the subject than that in a sample from a normal person, then the subject is a candidate for treatment with an effective amount of a granulysin inhibitor.

"Treating" refers to administration of an antibody or composition thereof to a subject, who has one or more of the above-descried disorders, with the purpose to cure, alleviate, relieve, remedy, prevent, or ameliorate the disorder, the symptom of the disorder, the disease state secondary to the disorder, or the predisposition toward the disorder. "Preventing" refers to eliminating or reducing the occurrence of the above described disorders. As understood in the art, "prevent" or "prevention" does not require complete (100%) avoidance of the occurrence of such disorders. Instead, reduction in the probability or extents of the disorders would be considered successful prevention.

An "effective amount" refers to an amount that is capable of producing a medially desirable result in a treated subject. The treatment method can be performed alone or in conjunction with other drugs or therapy. For treatment of a skin disorder, such as SJS and TEN, the therapeutic agent may be delivered topically or internally (e.g., by injection).

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in these dosage levels can be adjusted using standard empirical routines for optimization as is well understood in the art. Encapsulation of the therapeutic agent in a suitable delivery vehicle (e.g., polymeric microparticles or implantable devices) may increase the efficiency of delivery.

The above examples demonstrate various aspect and utility of embodiments of the invention. While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An anti-granulysin antibody, or an scFv or Fab fragment thereof, wherein the antibody has the ability to neutralize an activity of granulysin, wherein the antibody binds to epitope regions located at residues 64-67 and at residues 97-108 in the sequence of granulysin (SEQ ID NO:79).

2. The anti-granulysin antibody, or the Fab fragment thereof, according to claim 1, wherein the antibody comprises the sequences of SEQ ID NO:82 through SEQ ID NO:87, or
SEQ ID NO:88 through SEQ ID NO:93 or
SEQ ID NO:94 through SEQ ID NO:99, or
SEQ ID NO:100 through SEQ ID NO:105, or
SEQ ID NO:106 through SEQ ID NO:111, or
SEQ ID NO:112 through SEQ ID NO:117, or
SEQ ID NO:118 through SEQ ID NO:123 or
SEQ ID NO:124 through SEQ ID NO:129, or
SEQ ID NO:130 through SEQ ID NO:135, or SEQ ID NO:136 through SEQ ID NO:141, or
SEQ ID NO:142 through SEQ ID NO:147, or
SEQ ID NO:148 through SEQ ID NO:153 or
SEQ ID NO:154 through SEQ ID NO:159, or
SEQ ID NO:160 through SEQ ID NO:165, or
SEQ ID NO:166 through SEQ ID NO:171, or
SEQ ID NO:172 through SEQ ID NO:177, or
SEQ ID NO:178 through SEQ ID NO:183 or
SEQ ID NO:184 through SEQ ID NO:189, or
SEQ ID NO:190 through SEQ ID NO:195.

3. The anti-granulysin antibody, or the scFv or Fab fragment thereof, according to claim 1, wherein the antibody comprises a sequence selected from the sequences of SEQ ID NO:39 to SEQ ID NO:76.

4. The anti-granulysin antibody, or the Fab fragment thereof, according to claim 1, wherein the antibody comprises the sequences of
SEQ ID NO:39 and SEQ ID NO:40, or
SEQ ID NO:41 and SEQ ID NO:42 or
SEQ ID NO:43 and SEQ ID NO:44, or
SEQ ID NO:45 and SEQ ID NO:46, or
SEQ ID NO:47 and SEQ ID NO:48, or
SEQ ID NO:49 and SEQ ID NO:50, or
SEQ ID NO:51 and SEQ ID NO:52 or
SEQ ID NO:53 and SEQ ID NO:54, or
SEQ ID NO:55 and SEQ ID NO:56, or
SEQ ID NO:57 and SEQ ID NO:58, or
SEQ ID NO:59 and SEQ ID NO:60, or
SEQ ID NO:61 and SEQ ID NO:62 or
SEQ ID NO:63 and SEQ ID NO:64, or
SEQ ID NO:65 and SEQ ID NO:66, or
SEQ ID NO:67 and SEQ ID NO:68, or
SEQ ID NO:69 and SEQ ID NO:70, or
SEQ ID NO:71 and SEQ ID NO:72 or
SEQ ID NO:73 and SEQ ID NO:74, or
SEQ ID NO:75 and SEQ ID NO:76.

5. The anti-granulysin antibody, or the scFv or Fab fragment thereof, according to claim 1, wherein the antibody is a monoclonal antibody.

6. The anti-granulysin antibody, or the scFv or Fab fragment thereof, according to claim 5, wherein the antibody is a humanized antibody or a human antibody.

7. A method for treating or reducing the occurrence of an unwanted immune response disorder, comprising:
administering to a subject in need thereof the antibody or the scFv or Fab fragment thereof, according to claim 1, wherein the unwanted immune response disorder is Steven-Johnson syndrome (SJS), toxic epidermal necrolysis (TEN), or graft versus host disease (GVHD).

8. The method according to claim 7, wherein the antibody comprises the sequences of
SEQ ID NO:82 through SEQ ID NO:87, or
SEQ ID NO:88 through SEQ ID NO:93 or
SEQ ID NO:94 through SEQ ID NO:99, or
SEQ ID NO:100 through SEQ ID NO:105, or
SEQ ID NO:106 through SEQ ID NO:111, or
SEQ ID NO:112 through SEQ ID NO:117, or
SEQ ID NO:118 through SEQ ID NO:123 or
SEQ ID NO:124 through SEQ ID NO:129, or
SEQ ID NO:130 through SEQ ID NO:135, or
SEQ ID NO:136 through SEQ ID NO:141, or
SEQ ID NO:142 through SEQ ID NO:147, or
SEQ ID NO:148 through SEQ ID NO:153 or
SEQ ID NO:154 through SEQ ID NO:159, or
SEQ ID NO:160 through SEQ ID NO:165, or
SEQ ID NO:166 through SEQ ID NO:171, or
SEQ ID NO:172 through SEQ ID NO:177, or
SEQ ID NO:178 through SEQ ID NO:183 or
SEQ ID NO:184 through SEQ ID NO:189, or
SEQ ID NO:190 through SEQ ID NO:195.

9. The method according to claim 7, wherein the antibody comprises a sequence selected from the sequences of SEQ ID NO:39 to SEQ ID NO:76.

10. The method according to claim 7, wherein the antibody comprises the sequences of
SEQ ID NO:39 and SEQ ID NO:40, or
SEQ ID NO:41 and SEQ ID NO:42 or
SEQ ID NO:43 and SEQ ID NO:44, or
SEQ ID NO:45 and SEQ ID NO:46, or
SEQ ID NO:47 and SEQ ID NO:48, or
SEQ ID NO:49 and SEQ ID NO:50, or
SEQ ID NO:51 and SEQ ID NO:52 or
SEQ ID NO:53 and SEQ ID NO:54, or
SEQ ID NO:55 and SEQ ID NO:56, or
SEQ ID NO:57 and SEQ ID NO:58, or
SEQ ID NO:59 and SEQ ID NO:60, or
SEQ ID NO:61 and SEQ ID NO:62 or
SEQ ID NO:63 and SEQ ID NO:64, or
SEQ ID NO:65 and SEQ ID NO:66, or
SEQ ID NO:67 and SEQ ID NO:68, or
SEQ ID NO:69 and SEQ ID NO:70, or
SEQ ID NO:71 and SEQ ID NO:72 or
SEQ ID NO:73 and SEQ ID NO:74, or
SEQ ID NO:75 and SEQ ID NO:76.

11. The method according to claim 7, wherein the unwanted immune response disorder is GVHD.

12. The method according to claim 7, wherein the antibody is a monoclonal antibody.

13. The method of claim 12, wherein the antibody is a humanized antibody or a human antibody.

* * * * *